(12) United States Patent
Hellesoy et al.

(10) Patent No.: US 11,035,008 B2
(45) Date of Patent: Jun. 15, 2021

(54) BIOMARKERS FOR CANCER

(71) Applicant: BERGENBIO ASA, Bergen (NO)

(72) Inventors: Monica Hellesoy, Bergen (NO); Linn Hodneland Nilsson, Bergen (NO); David Robert Micklem, Bergen (NO)

(73) Assignee: BerGenBio ASA, Bergen (NO)

( * ) Notice: Subject to any disclaimer, the term of this patent is extended or adjusted under 35 U.S.C. 154(b) by 0 days.

(21) Appl. No.: 15/742,702

(22) PCT Filed: Jul. 8, 2016

(86) PCT No.: PCT/EP2016/066357
§ 371 (c)(1),
(2) Date: Jan. 8, 2018

(87) PCT Pub. No.: WO2017/009261
PCT Pub. Date: Jan. 19, 2017

(65) Prior Publication Data
US 2018/0208989 A1    Jul. 26, 2018

(30) Foreign Application Priority Data

Jul. 10, 2015 (GB) .................................... 1512133

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01); *G01N 2800/52* (2013.01); *G01N 2800/60* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 2012/0322073 A1* | 12/2012 | Lopez-Girona | C07K 16/18 435/6.12 |
| 2014/0121126 A1* | 5/2014 | Bivona | G01N 33/57423 506/9 |
| 2014/0294818 A1* | 10/2014 | Chen | C09B 1/06 424/133.1 |

FOREIGN PATENT DOCUMENTS

| | | |
|---|---|---|
| WO | 2010103388 A2 | 9/2010 |
| WO | 2011150256 A2 | 12/2011 |
| WO | 2012135714 A2 | 10/2012 |
| WO | 2012135841 A2 | 10/2012 |
| WO | 2012149014 A1 | 11/2012 |
| WO | 2013164788 A2 | 11/2013 |

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Cheung et al (Nature Genetics 2003 vol. 33 p. 422) (Year: 2003).*
Wu (Journal of pathology 2001 vol. 195 p. 53) (Year: 2001).*
Newton etal (Journal of Computational Biology 2001 vol. 8 p. 37) (Year: 2001).*
Wu, Xiaoliang, et al., "AXL kinase as a novel target for cancer therapy," Oncotarget, Oct. 16, 2014, vol. 5, No. 20, pp. 9546-9563.
Gjerdrum et al., "Axl is an essential epithelial-to-mesenchymal transition-induced regulator of breast cancer metastasis and patient survival," PNAS, vol. 107, No. 3, Jan. 19, 2010, pp. 1124-1129.
Holland et al., "R428, a Selective Small Molecule Inhibitor of Axl Kinase, Blocks Tumor Spread and Prolongs Survival in Models of Metastatic Breast Cancer," Cancer Res; 70(4), Feb. 15, 2010, pp. 1544-1554.
Luo, Ji, "Cancer's sweet tooth for serine," Breast Cancer Research 2011, 13:317, pp. 1-3.
Zogg, Cheryl K., "Phosphoglycerate Dehydrogenase: Potential Therapeutic Target and Putative Metabolic Oncogene," Journal of Oncology, vol. 214, Article ID 524101, 13 pages.
International Search Report and Written Opinion issued in corresponding Application No. PCT/EP2016/066357, dated Oct. 4, 2016, 19 pages.

* cited by examiner

*Primary Examiner* — Katherine D Salmon
(74) *Attorney, Agent, or Firm* — McNeill Baur PLLC

(57) ABSTRACT

The use of PHGDH as a biomarker for detecting the occurrence of epithelial-to-mesenchymal transition (EMT) in a subject, and the use of PHGDH modulators to treat cancer is disclosed herein. Also disclosed are various methods for detecting the occurrence of epithelial-to-mesenchymal transition (EMT) in a subject by measuring PHGDH expression and/or activity.

10 Claims, 27 Drawing Sheets
Specification includes a Sequence Listing.

SEQUENCE LISTING

<160> NUMBER OF SEQ ID NOS: 12

<210> SEQ ID NO 1
<211> LENGTH: 533
<212> TYPE: PRT
<213> ORGANISM: Homo sapiens

<400> SEQUENCE: 1

```
Met Ala Phe Ala Asn Leu Arg Lys Val Leu Ile Ser Asp Ser Leu Asp
1               5                   10                  15

Pro Cys Cys Arg Lys Ile Leu Gln Asp Gly Gly Leu Gln Val Val Glu
            20                  25                  30

Lys Gln Asn Leu Ser Lys Glu Glu Leu Ile Ala Glu Leu Gln Asp Cys
        35                  40                  45

Glu Gly Leu Ile Val Arg Ser Ala Thr Lys Val Thr Ala Asp Val Ile
    50                  55                  60

Asn Ala Ala Glu Lys Leu Gln Val Val Gly Arg Ala Gly Thr Gly Val
65                  70                  75                  80

Asp Asn Val Asp Leu Glu Ala Ala Thr Arg Lys Gly Ile Leu Val Met
                85                  90                  95

Asn Thr Pro Asn Gly Asn Ser Leu Ser Ala Ala Glu Leu Thr Cys Gly
            100                 105                 110

Met Ile Met Cys Leu Ala Arg Gln Ile Pro Gln Ala Thr Ala Ser Met
        115                 120                 125

Lys Asp Gly Lys Trp Glu Arg Lys Lys Phe Met Gly Thr Glu Leu Asn
    130                 135                 140

Gly Lys Thr Leu Gly Ile Leu Gly Leu Gly Arg Ile Gly Arg Glu Val
145                 150                 155                 160

Ala Thr Arg Met Gln Ser Phe Gly Met Lys Thr Ile Gly Tyr Asp Pro
                165                 170                 175

Ile Ile Ser Pro Glu Val Ser Ala Ser Phe Gly Val Gln Gln Leu Pro
            180                 185                 190

Leu Glu Glu Ile Trp Pro Leu Cys Asp Phe Ile Thr Val His Thr Pro
        195                 200                 205
```

Leu Leu Pro Ser Thr Thr Gly Leu Leu Asn Asp Asn Thr Phe Ala Gln
        210                 215                 220

Cys Lys Lys Gly Val Arg Val Val Asn Cys Ala Arg Gly Gly Ile Val
225                 230                 235                 240

Asp Glu Gly Ala Leu Leu Arg Ala Leu Gln Ser Gly Gln Cys Ala Gly
                245                 250                 255

Ala Ala Leu Asp Val Phe Thr Glu Glu Pro Pro Arg Asp Arg Ala Leu
                260                 265                 270

Val Asp His Glu Asn Val Ile Ser Cys Pro His Leu Gly Ala Ser Thr
            275                 280                 285

Lys Glu Ala Gln Ser Arg Cys Gly Glu Glu Ile Ala Val Gln Phe Val
        290                 295                 300

Asp Met Val Lys Gly Lys Ser Leu Thr Gly Val Val Asn Ala Gln Ala
305                 310                 315                 320

Leu Thr Ser Ala Phe Ser Pro His Thr Lys Pro Trp Ile Gly Leu Ala
                325                 330                 335

Glu Ala Leu Gly Thr Leu Met Arg Ala Trp Ala Gly Ser Pro Lys Gly
                340                 345                 350

Thr Ile Gln Val Ile Thr Gln Gly Thr Ser Leu Lys Asn Ala Gly Asn
            355                 360                 365

Cys Leu Ser Pro Ala Val Ile Val Gly Leu Leu Lys Glu Ala Ser Lys
        370                 375                 380

Gln Ala Asp Val Asn Leu Val Asn Ala Lys Leu Leu Val Lys Glu Ala
385                 390                 395                 400

Gly Leu Asn Val Thr Thr Ser His Ser Pro Ala Ala Pro Gly Glu Gln
                405                 410                 415

Gly Phe Gly Glu Cys Leu Leu Ala Val Ala Leu Ala Gly Ala Pro Tyr
                420                 425                 430

Gln Ala Val Gly Leu Val Gln Gly Thr Thr Pro Val Leu Gln Gly Leu
            435                 440                 445

Asn Gly Ala Val Phe Arg Pro Glu Val Pro Leu Arg Arg Asp Leu Pro
450                 455                 460

Leu Leu Leu Phe Arg Thr Gln Thr Ser Asp Pro Ala Met Leu Pro Thr
465                 470                 475                 480

Met Ile Gly Leu Leu Ala Glu Ala Gly Val Arg Leu Leu Ser Tyr Gln
                485                 490                 495

Thr Ser Leu Val Ser Asp Gly Glu Thr Trp His Val Met Gly Ile Ser
            500                 505                 510

Ser Leu Leu Pro Ser Leu Glu Ala Trp Lys Gln His Val Thr Glu Ala
        515                 520                 525

Phe Gln Phe His Phe
    530

<210> SEQ ID NO 2
<211> LENGTH: 2478
<212> TYPE: DNA
<213> ORGANISM: Homo sapiens

<400> SEQUENCE: 2
cacctttccg cgggccgcgg ggatggcggc gcagggcgta gggcctgggc cggggtcggc        60 ggcgccccg gggctggagg cggcccggca gaagctggcg ctgcggcgga agaaggtgct       120
gagcaccgaa ggagatggag ctgtacgagc tggcgcaggc ggcggcggc gctatcgacc       180 ccgacgtgtt caagatcctg gtggacctgc tgaagctgaa cgtggccccc ctcgccgtct       240

-continued

```
tccagatgct caagtccatg tgtgccgggc agaggctagc gagcgagccc caggaccctg      300
cggccgtgtc tctgcccacg tcgagcgtgc ccgagacccg agggagaaac aaaggcagcg      360
ctgccctcgg gggagcattg gccctggcgg aacgcagcag ccgcgaagga tccagccaga      420
ggatgccacg ccagcccagc gctaccaggc tgcccaaggg gggcgggcct gggaagagcc      480
ctacacgggg cagcacctag gatggggcag agacttgttg catctttgtc cccagcaaag      540
gctacatgtt acctccttca attgataata aacctttctg agatgcaaac tcgagaatac      600
tgcccagtta ctctagcgcg ccaggccgaa ccgcagcttc ttggcttagg tacttctact      660
cacagcggcc gattccgagg ccaactccag caatggcttt tgcaaatctg cggaaagtgc      720
tcatcagtga cagcctggac ccttgctgcc ggaagatctt gcaagaggga gggctgcagg      780
tggtggaaaa gcagaacctt agcaaagagg agctgatagc ggagctgcag gactgtgaag      840
gccttattgt tcgctctgcc accaaggtga ccgctgatgt catcaacgca gctgagaaac      900
tccaggtggt gggcagggct ggcacaggtg tggacaatgt ggatctggag ccgcaacaa      960 ggaagggcat cttggttatg aacaccccca atgggaacag cctcagtgcc gcagaactca     1020
cttgtggaat gatcatgtgc ctggccaggc agattcccca ggcgacggct tcgatgaagg     1080
acggcaaatg ggagcggaag aagttcatgg gaacagagct gaatggaaag accctgggaa     1140
ttcttggcct gggcaggatt gggagagagg tagctacccg gatgcagtcc tttgggatga     1200
agactatagg gtatgacccc atcatttccc cagaggtctc ggcctccttt ggtgttcagc     1260
agctgccccT ggaggagatc tggcctctct gtgatttcat cactgtgcac actcctctcc     1320
tgccctccac gacaggcttg ctgaatgaca acacctttgc ccagtgcaag aagggggtgc     1380
gtgtggtgaa ctgtgcccgt ggagggatcg tggacgaagg cgccctgctc cgggccctgc     1440
agtctggcca gtgtgccggg gctgcactgg acgtgtttac ggaagagccg ccacgggacc     1500
gggccttggt ggaccatgag aatgtcatca gctgtcccca cctgggtgcc agcaccaagg     1560
aggctcagag ccgctgtggg gaggaaattg ctgttcagtt cgtggacatg gtgaagggga     1620
aatctctcac gggggttgtg aatgcccagg cccttaccag tgccttctct ccacacacca     1680
agccttggat tggtctggca gaagctctgg ggacactgat gcgagcctgg gctgggtccc     1740
ccaaagggac catccaggtg ataacacagg gaacatccct gaagaatgct gggaactgcc     1800
taagccccgc agtcattgtc ggcctcctga aagaggcttc caagcaggcg gatgtgaact     1860
tggtgaacgc taagctgctg gtgaaagagg ctggcctcaa tgtcaccacc tcccacagcc     1920
ctgctgcacc aggggagcaa ggcttcgggg aatgcctcct ggccgtggcc ctggcaggcg     1980
ccccttacca ggctgtgggc ttggtccaag gcactacacc tgtactgcag gggctcaatg     2040
gagctgtctt caggccagaa gtgcctctcc gcagggacct gccctgctc ctattccgga     2100 ctcagacctc tgaccctgca atgctgccta ccatgattgg cctcctggca gaggcaggcg     2160
tgcggctgct gtcctaccag acttcactgg tgtcagatgg ggagacctgg cacgtcatgg     2220
gcatctcctc cttgctgccc agcctggaag cgtggaagca gcatgtgact gaagccttcc     2280
agttccactt ctaaccttgg agctcactgg tccctgcctc tggggctttt ctgaagaaac     2340
ccacccactg tgatcaatag ggagagaaaa tccacattct tgggctgaac gcgggcctct     2400
gacactgctt acactgcact ctgaccctgt agtacagcaa taaccgtcta ataaagagcc     2460
tacccccaaa aaaaaaaa                                                   2478
```

<210> SEQ ID NO 3

```
<211> LENGTH: 894
<212> TYPE: PRT
<213> ORGANISM: Homo sapiens

<400> SEQUENCE: 3

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Gln Asp Asp Trp
                85                  90                  95

Ile Val Val Ser Gln Leu Arg Ile Thr Ser Leu Gln Leu Ser Asp Thr
                100                 105                 110

Gly Gln Tyr Gln Cys Leu Val Phe Leu Gly His Gln Thr Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
                180                 185                 190

His Val Pro Gly Leu Asn Lys Thr Ser Ser Phe Ser Cys Glu Ala His
            195                 200                 205

Asn Ala Lys Gly Val Thr Thr Ser Arg Thr Ala Thr Ile Thr Val Leu
        210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asn Asp Gly Met Gly Ile Gln
                260                 265                 270

Ala Gly Glu Pro Asp Pro Pro Glu Glu Pro Leu Thr Ser Gln Ala Ser
            275                 280                 285

Val Pro Pro His Gln Leu Arg Leu Gly Ser Leu His Pro His Thr Pro
        290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
            355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
```

```
              385                 390                 395                 400
         Asn Leu Thr Val Cys Val Ala Ala Tyr Thr Ala Ala Gly Asp Gly Pro
                         405                 410                 415

Trp Ser Leu Pro Val Pro Leu Glu Ala Trp Arg Pro Gly Gln Ala Gln
                         420                 425                 430

Pro Val His Gln Leu Val Lys Glu Pro Ser Thr Pro Ala Phe Ser Trp
                         435                 440                 445

Pro Trp Trp Tyr Val Leu Leu Gly Ala Val Ala Ala Ala Cys Val
                 450                 455                 460

Leu Ile Leu Ala Leu Phe Leu His Arg Arg Lys Lys Glu Thr Arg
         465                 470                 475                 480

Tyr Gly Glu Val Phe Glu Pro Thr Val Glu Arg Gly Glu Leu Val Val
                         485                 490                 495

Arg Tyr Arg Val Arg Lys Ser Tyr Ser Arg Arg Thr Thr Glu Ala Thr
                         500                 505                 510

Leu Asn Ser Leu Gly Ile Ser Glu Glu Leu Lys Glu Lys Leu Arg Asp
                         515                 520                 525

Val Met Val Asp Arg His Lys Val Ala Leu Gly Lys Thr Leu Gly Glu
                 530                 535                 540

Gly Glu Phe Gly Ala Val Met Glu Gly Gln Leu Asn Gln Asp Asp Ser
         545                 550                 555                 560

Ile Leu Lys Val Ala Val Lys Thr Met Lys Ile Ala Ile Cys Thr Arg
                         565                 570                 575

Ser Glu Leu Glu Asp Phe Leu Ser Glu Ala Val Cys Met Lys Glu Phe
                         580                 585                 590

Asp His Pro Asn Val Met Arg Leu Ile Gly Val Cys Phe Gln Gly Ser
                 595                 600                 605

Glu Arg Glu Ser Phe Pro Ala Pro Val Val Ile Leu Pro Phe Met Lys
                 610                 615                 620

His Gly Asp Leu His Ser Phe Leu Leu Tyr Ser Arg Leu Gly Asp Gln
         625                 630                 635                 640

Pro Val Tyr Leu Pro Thr Gln Met Leu Val Lys Phe Met Ala Asp Ile
                         645                 650                 655

Ala Ser Gly Met Glu Tyr Leu Ser Thr Lys Arg Phe Ile His Arg Asp
                         660                 665                 670

Leu Ala Ala Arg Asn Cys Met Leu Asn Glu Asn Met Ser Val Cys Val
                         675                 680                 685

Ala Asp Phe Gly Leu Ser Lys Lys Ile Tyr Asn Gly Asp Tyr Tyr Arg
                 690                 695                 700

Gln Gly Arg Ile Ala Lys Met Pro Val Lys Trp Ile Ala Ile Glu Ser
         705                 710                 715                 720

Leu Ala Asp Arg Val Tyr Thr Ser Lys Ser Asp Val Trp Ser Phe Gly
                         725                 730                 735

Val Thr Met Trp Glu Ile Ala Thr Arg Gly Gln Thr Pro Tyr Pro Gly
                         740                 745                 750

Val Glu Asn Ser Glu Ile Tyr Asp Tyr Leu Arg Gln Gly Asn Arg Leu
                         755                 760                 765

Lys Gln Pro Ala Asp Cys Leu Asp Gly Leu Tyr Ala Leu Met Ser Arg
                 770                 775                 780

Cys Trp Glu Leu Asn Pro Gln Asp Arg Pro Ser Phe Thr Glu Leu Arg
         785                 790                 795                 800

Glu Asp Leu Glu Asn Thr Leu Lys Ala Leu Pro Pro Ala Gln Glu Pro
                         805                 810                 815
```

Asp Ile Leu Tyr Val Asn Met Asp Glu Gly Gly Tyr Pro Glu
820                     825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 4
<211> LENGTH: 3227
<212> TYPE: DNA
<213> ORGANISM: Homo sapiens
<400> SEQUENCE: 4

| | | | | | |
|---|---|---|---|---|---|
| gctgggcaaa | gccggtggca | agggcctccc | ctgccgctgt | gccaggcagg | cagtgccaaa | 60
| tccggggagc | ctggagctgg | ggggagggcc | ggggacagcc | cggccctgcc | cctcccccg | 120
| ctgggagccc | agcaacttct | gaggaaagtt | tggcacccat | ggcgtggcgg | tgccccagga | 180
| tgggcagggt | cccgctggcc | tggtgcttgg | cgctgtgcgg | ctgggcgtgc | atggccccca | 240
| ggggcacgca | ggctgaagaa | agtcccttcg | tgggcaaccc | agggaatatc | acaggtgccc | 300
| ggggactcac | gggcacccct | cggtgtcagc | tccaggttca | gggagagccc | ccgaggtac | 360
| attggcttcg | ggatggacag | atcctggagc | tcgcggacag | cacccagacc | caggtgcccc | 420
| tgggtgagga | tgaacaggat | gactggatag | tggtcagcca | gctcagaatc | acctccctgc | 480
| agctttccga | cacgggacag | taccagtgtt | tggtgtttct | gggacatcag | accttcgtgt | 540
| cccagcctgg | ctatgttggg | ctggagggct | tgccttactt | cctggaggag | cccgaagaca | 600
| ggactgtggc | cgccaacacc | cccttcaacc | tgagctgcca | agctcaggga | ccccagagc | 660
| ccgtggacct | actctggctc | caggatgctg | tcccctggc | acggctccca | ggtcacggcc | 720
| cccagcgcag | cctgcatgtt | ccagggctga | caagacatc | ctctttctcc | tgcgaagccc | 780
| ataacgccaa | gggggtcacc | acatcccgca | cagccaccat | cacagtgctc | cccagcagc | 840
| cccgtaacct | ccacctggtc | tcccgccaac | ccacggagct | ggaggtggct | tggactccag | 900
| gcctgagcgg | catctacccc | ctgacccact | gcaccctgca | ggctgtgctg | tcagacgatg | 960
| ggatgggcat | ccaggcggga | gaaccagacc | ccccagagga | gccctcacc | tcgcaagcat | 1020
| ccgtgccccc | ccatcagctt | cggctaggca | gcctccatcc | tcacacccct | tatcacatcc | 1080
| gcgtggcatg | caccagcagc | cagggcccct | catcctggac | ccactggctt | cctgtggaga | 1140
| cgccggaggg | agtgccctg | gccccccta | agaacattag | tgctacgcgg | aatgggagcc | 1200
| aggccttcgt | gcattggcaa | gagccccggg | cgccctgca | gggtaccctg | ttagggtacc | 1260
| ggctggcgta | tcaaggccag | gacaccccag | aggtgctaat | ggacataggg | ctaaggcaag | 1320
| aggtgaccct | ggagctgcag | ggggacgggt | ctgtgtccaa | tctgacagtg | tgtgtggcag | 1380
| cctacactgc | tgctggggat | ggaccctgga | gcctccagt | accctggag | gcctggcgcc | 1440
| cagtgaagga | accttcaact | cctgccttct | cgtggccctg | gtggtatgta | ctgctaggag | 1500
| cagtcgtggc | cgctgcctgt | gtcctcatct | tggctctctt | ccttgtccac | cggcgaaaga | 1560
| aggagacccg | ttatgcagaa | gtgtttgaac | caacagtgga | aagaggtgaa | ctggtagtca | 1620
| ggtaccgcgt | gcgcaagtcc | tacagtcgtc | ggaccactga | agctaccttg | aacagcctgg | 1680

```
gcatcagtga agagctgaag gagaagctgc gggatgtgat ggtggaccgg cacaaggtgg    1740
ccctggggaa gactctggga gagggagagt ttggagctgt gatggaaggc cagctcaacc    1800
aggacgactc catcctcaag gtggctgtga agacgatgaa gattgccatc tgcacgaggt    1860
cagagctgga ggatttcctg agtgaagcgg tctgcatgaa ggaatttgac catcccaacg    1920
tcatgaggct catcggtgtc tgtttccagg ttctgaacg agagagcttc ccagcacctg    1980
tggtcatctt acctttcatg aaacatggag acctacacag cttcctcctc tattcccggc    2040
tcggggacca gccagtgtac ctgcccactc agatgctagt gaagttcatg cagacatcg    2100 ccagtggcat ggagtatctg agtaccaaga gattcataca ccgggacctg gcggccagga    2160
actgcatgct gaatgagaac atgtccgtgt gtgtggcgga cttcgggctc tccaagaaga    2220
tctacaatgg ggactactac cgccagggac gtatcgccaa gatgccagtc aagtggattg    2280
ccattgagag tctagctgac cgtgtctaca ccagcaagag cgatgtgtgg tccttcgggg    2340
tgacaatgtg ggagattgcc acaagaggcc aaacccccata tccgggcgtg gagaacagcg    2400
agatttatga ctatctgcgc cagggaaatc gcctgaagca gcctgcggac tgtctggatg    2460
gactgtatgc cttgatgtcg cggtgctggg agctaaatcc ccaggaccgg ccaagttta    2520 cagagctgcg ggaagatttg gagaacacac tgaaggcctt gcctcctgcc caggagcctg    2580
acgaaatcct ctatgtcaac atggatgagg gtggaggtta tcctgaaccc cctggagctg    2640
caggaggagc tgaccccca acccagccag accctaagga ttcctgtagc tgcctcactg    2700
cggctgaggt ccatcctgct ggacgctatg tcctctgccc ttccacaacc cctagccccg    2760
ctcagcctgc tgataggggc tccccagcag ccccagggca ggaggatggt gcctgagaca    2820
accctccacc tggtactccc tctcaggatc caagctaagc actgccactg gggaaaactc    2880
caccttccca cttttccacc ccacgcctta tccccacttg cagccctgtc ttcctaccta    2940
tcccacctcc atcccagaca ggtccctccc cttctctgtg cagtagcatc accttgaaag    3000
cagtagcatc accatctgta aaggaaggg ttggattgc aatatctgaa gccctcccag    3060
gtgttaacat tccaagactc tagagtccaa ggtttaaaga gtctagattc aaaggttcta    3120
ggtttcaaag atgctgtgag tctttggttc taaggacctg aaattccaaa gtctctaatt    3180
ctattaaagt gctaaggttc taaggcaaaa aaaaaaaaaa aaaaaaa              3227
```

<210> SEQ ID NO 5
<211> LENGTH: 479
<212> TYPE: PRT
<213> ORGANISM: Homo sapiens

<400> SEQUENCE: 5

```
Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95
```

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Met Asp Ala Ser Thr Thr His His Lys Arg Lys Thr
    130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
    290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
    370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
    450                 455                 460

Arg Pro His Phe Pro Gln Phe Ser Tyr Ser Ala Ser Gly Arg Glu
465                 470                 475

<210> SEQ ID NO 6
<211> LENGTH: 1708
<212> TYPE: DNA
<213> ORGANISM: Homo sapiens

<400> SEQUENCE: 6

-continued

```
agggggagtca tcatgagcga tgttaccatt gtgaaggaag gttgggttca gaagagggga      60
gaatatataa aaaactggag gccaagatac ttccttttga agacagatgg ctcattcata     120
ggatataaag agaaacctca agatgtggat ttaccttatc ccctcaacaa ctttttcagtg    180
gcaaaatgcc agttaatgaa aacagaacga ccaaagccaa acacatttat aatcagatgt    240
ctccagtgga ctactgttat agagagaaca tttcatgtag atactccaga ggaaagggaa    300
gaatggacag aagctatcca ggctgtagca gacagactgc agaggcaaga agaggagaga    360
atgaattgta gtccaacttc acaaattgat aatataggag aggaagagat ggatgcctct    420
acaacccatc ataaaagaaa gacaatgaat gattttgact attttgaaact actaggtaaa    480
ggcacttttg ggaaagttat tttggttcga gagaaggcaa gtggaaaata ctatgctatg    540
aagattctga gaaagaagt cattattgca aaggatgaag tggcacacac tctaactgaa    600
agcagagtat aaagaacac tagacatccc ttttaacat ccttgaaata ttccttccag      660
acaaaagacc gtttgtgttt tgtgatgaa tatgttaatg ggggcgagct gttttttccat    720
ttgtcgagag agcgggtgtt ctctgaggac cgcacacgtt tctatggtgc agaaattgtc    780
tctgccttgg actatctaca ttccggaaag attgtgtacc gtgatctcaa gttggagaat    840
ctaatgctgg acaaagatgg ccacataaaa attacagatt ttggactttg caaagaaggg    900
atcacagatg cagccaccat gaagacattc tgtggcactc cagaatatct ggcaccagag    960
gtgttagaag ataatgacta tggccgagca gtagactggt ggggcctagg ggttgtcatg   1020
tatgaaatga tgtgtgggag gttacctttc tacaaccagg accatgagaa acttttttgaa   1080
ttaatattaa tggaagacat taaatttcct cgaacactct cttcagatgc aaaatcattg   1140
ctttcagggc tcttgataaa ggatccaaat aaacgccttg gtggaggacc agatgatgca   1200
aaagaaatta tgagacacag tttcttctct ggagtaaact ggcaagatgt atatgataaa   1260
aagcttgtac ctccttttaa acctcaagta acatctgaga cagatactag atattttgat   1320
gaagaattta cagctcagac tattacaata acaccacctg aaaaatatga tgaggatggt   1380
atggactgca tggacaatga gaggcggccg catttccctc aatttttccta ctctgcaagt   1440
ggacgagaat aagtctcttt cattctgcta cttcactgtc atcttcaatt tattactgaa   1500
aatgattcct ggacatcacc agtcctagct cttacacata gcaggggcac cttccgacat   1560
cccagaccag ccaagggtcc tcaccctcg ccacctttca ccctcatgaa acacacata      1620
cacgcaaata cactccagtt tttgttttg catgaaattg tatctcagtc taaggtctca    1680
tgctgttgct gctactgtct tactatta                                        1708
```

<210> SEQ ID NO 7
<211> LENGTH: 901
<212> TYPE: PRT
<213> ORGANISM: Homo sapiens

<400> SEQUENCE: 7

```
Met Glu Ala Asn Gln Cys Pro Leu Val Val Glu Pro Ser Tyr Pro Asp
1               5                   10                  15

Leu Val Ile Asn Val Gly Glu Val Thr Leu Gly Glu Glu Asn Arg Lys
            20                  25                  30

Lys Leu Gln Lys Ile Gln Arg Asp Gln Glu Lys Glu Arg Val Met Arg
        35                  40                  45

Ala Ala Cys Ala Leu Leu Asn Ser Gly Gly Gly Val Ile Arg Met Ala
    50                  55                  60
```

Lys Lys Val Glu His Pro Val Glu Met Gly Leu Asp Leu Glu Gln Ser
65                  70                  75                  80

Leu Arg Glu Leu Ile Gln Ser Ser Asp Leu Gln Ala Phe Phe Glu Thr
                85                  90                  95

Lys Gln Gln Gly Arg Cys Phe Tyr Ile Phe Val Lys Ser Trp Ser Ser
            100                 105                 110

Gly Pro Phe Pro Glu Asp Arg Ser Val Lys Pro Arg Leu Cys Ser Leu
        115                 120                 125

Ser Ser Ser Leu Tyr Arg Arg Ser Glu Thr Ser Val Arg Ser Met Asp
    130                 135                 140

Ser Arg Glu Ala Phe Cys Phe Leu Lys Thr Lys Arg Lys Pro Lys Ile
145                 150                 155                 160

Leu Glu Glu Gly Pro Phe His Lys Ile His Lys Gly Val Tyr Gln Glu
                165                 170                 175

Leu Pro Asn Ser Asp Pro Ala Asp Pro Asn Ser Asp Pro Ala Asp Leu
            180                 185                 190

Ile Phe Gln Lys Asp Tyr Leu Glu Tyr Gly Glu Ile Leu Pro Phe Pro
        195                 200                 205

Glu Ser Gln Leu Val Glu Phe Lys Gln Phe Ser Thr Lys His Phe Gln
    210                 215                 220

Glu Tyr Val Lys Arg Thr Ile Pro Glu Tyr Val Pro Ala Phe Ala Asn
225                 230                 235                 240

Thr Gly Gly Gly Tyr Leu Phe Ile Gly Val Asp Asp Lys Ser Arg Glu
                245                 250                 255

Val Leu Gly Cys Ala Lys Glu Asn Val Asp Pro Asp Ser Leu Arg Arg
            260                 265                 270

Lys Ile Glu Gln Ala Ile Tyr Lys Leu Pro Cys Val His Phe Cys Gln
        275                 280                 285

Pro Gln Arg Pro Ile Thr Phe Thr Leu Lys Ile Val Asn Val Leu Lys
    290                 295                 300

Arg Gly Glu Leu Tyr Gly Tyr Ala Cys Met Ile Arg Val Asn Pro Phe
305                 310                 315                 320

Cys Cys Ala Val Phe Ser Glu Ala Pro Asn Ser Trp Ile Val Glu Asp
                325                 330                 335

Lys Tyr Val Cys Ser Leu Thr Thr Glu Lys Trp Val Gly Met Met Thr
            340                 345                 350

Asp Thr Asp Pro Asp Leu Leu Gln Leu Ser Glu Asp Phe Glu Cys Gln
        355                 360                 365

Leu Ser Leu Ser Ser Gly Pro Pro Leu Ser Arg Pro Val Tyr Ser Lys
    370                 375                 380

Lys Gly Leu Glu His Lys Lys Glu Leu Gln Gln Leu Leu Phe Ser Val
385                 390                 395                 400

Pro Pro Gly Tyr Leu Arg Tyr Thr Pro Glu Ser Leu Trp Arg Asp Leu
                405                 410                 415

Ile Ser Glu His Arg Gly Leu Glu Glu Leu Ile Asn Lys Gln Met Gln
            420                 425                 430

Pro Phe Phe Arg Gly Ile Leu Ile Phe Ser Arg Ser Trp Ala Val Asp
        435                 440                 445

Leu Asn Leu Gln Glu Lys Pro Gly Val Ile Cys Asp Ala Leu Leu Ile
    450                 455                 460

Ala Gln Asn Ser Thr Pro Ile Leu Tyr Thr Ile Leu Arg Glu Gln Asp
465                 470                 475                 480

Ala Glu Gly Gln Asp Tyr Cys Thr Arg Thr Ala Phe Thr Leu Lys Gln

```
                485                 490                 495
Lys Leu Val Asn Met Gly Gly Tyr Thr Gly Lys Val Cys Val Arg Ala
                500                 505                 510
Lys Val Leu Cys Leu Ser Pro Glu Ser Ser Ala Glu Ala Leu Glu Ala
                515                 520                 525
Ala Val Ser Pro Met Asp Tyr Pro Ala Ser Tyr Ser Leu Ala Gly Thr
                530                 535                 540
Gln His Met Glu Ala Leu Leu Gln Ser Leu Val Ile Val Leu Leu Gly
545                 550                 555                 560
Phe Arg Ser Leu Leu Ser Asp Gln Leu Gly Cys Glu Val Leu Asn Leu
                565                 570                 575
Leu Thr Ala Gln Gln Tyr Glu Ile Phe Ser Arg Ser Leu Arg Lys Asn
                580                 585                 590
Arg Glu Leu Phe Val His Gly Leu Pro Gly Ser Gly Lys Thr Ile Met
                595                 600                 605
Ala Met Lys Ile Met Glu Lys Ile Arg Asn Val Phe His Cys Glu Ala
                610                 615                 620
His Arg Ile Leu Tyr Val Cys Glu Asn Gln Pro Leu Arg Asn Phe Ile
625                 630                 635                 640
Ser Asp Arg Asn Ile Cys Arg Ala Glu Thr Arg Lys Thr Phe Leu Arg
                645                 650                 655
Glu Asn Phe Glu His Ile Gln His Ile Val Ile Asp Glu Ala Gln Asn
                660                 665                 670
Phe Arg Thr Glu Asp Gly Asp Trp Tyr Gly Lys Ala Lys Ser Ile Thr
                675                 680                 685
Arg Arg Ala Lys Gly Gly Pro Gly Ile Leu Trp Ile Phe Leu Asp Tyr
                690                 695                 700
Phe Gln Thr Ser His Leu Asp Cys Ser Gly Leu Pro Pro Leu Ser Asp
705                 710                 715                 720
Gln Tyr Pro Arg Glu Glu Leu Thr Arg Ile Val Arg Asn Ala Asp Pro
                725                 730                 735
Ile Ala Lys Tyr Leu Gln Lys Glu Met Gln Val Ile Arg Ser Asn Pro
                740                 745                 750
Ser Phe Asn Ile Pro Thr Gly Cys Leu Glu Val Phe Pro Glu Ala Glu
                755                 760                 765
Trp Ser Gln Gly Val Gln Gly Thr Leu Arg Ile Lys Lys Tyr Leu Thr
                770                 775                 780
Val Glu Gln Ile Met Thr Cys Val Ala Asp Thr Cys Arg Arg Phe Phe
785                 790                 795                 800
Asp Arg Gly Tyr Ser Pro Lys Asp Val Ala Val Leu Val Ser Thr Ala
                805                 810                 815
Lys Glu Val Glu His Tyr Lys Tyr Glu Leu Leu Lys Ala Met Arg Lys
                820                 825                 830
Lys Arg Val Val Gln Leu Ser Asp Ala Cys Asp Met Leu Gly Asp His
                835                 840                 845
Ile Val Leu Asp Ser Val Arg Arg Phe Ser Gly Leu Glu Arg Ser Ile
850                 855                 860
Val Phe Gly Ile His Pro Arg Thr Ala Asp Pro Ala Ile Leu Pro Asn
865                 870                 875                 880
Val Leu Ile Cys Leu Ala Ser Arg Ala Lys Gln His Leu Tyr Ile Phe
                885                 890                 895
Pro Trp Gly Gly His
                900
```

<210> SEQ ID NO 8
<211> LENGTH: 4620
<212> TYPE: DNA
<213> ORGANISM: Homo sapiens

<400> SEQUENCE: 8

| | | | | | | |
|---|---|---|---|---|---|---|
| gtgcagtggc | acgatcttgg | ttcaccacaa | tctcgtctcg | aaggctcagg | tgattctctc | 60 |
| acctcagccg | cctgagtagc | tgggaccaca | gtttcagctg | tgagttcaac | atggaggcaa | 120 |
| atcagtgccc | cctggttgtg | aaccatctt | acccagacct | ggtcatcaat | gtaggagaag | 180 |
| tgactcttgg | agaagaaaac | agaaaaaagc | tgcagaaaat | tcagagagac | caagagaagg | 240 |
| agagagttat | gcgggctgca | tgtgctttat | aaaactcagg | aggaggagtg | attcgaatgg | 300 |
| ccaagaaggt | tgagcatccc | gtggagatgg | gactggattt | agaacagtct | ttgagagagc | 360 |
| ttattcagtc | ttcagatctg | caggctttct | ttgagaccaa | gcaacaagga | aggtgttttt | 420 |
| acattttgt | taaatcttgg | agcagtggcc | ctttccctga | agatcgctct | ttcaagcccc | 480 |
| gcctttgcag | cctcagttct | tcattatacc | tgtagatctg | agacctctgt | gcgttccatg | 540 |
| gactcaagag | aggcattctg | tttcctgaag | accaaaagga | agccaaaaat | cttggaagaa | 600 |
| ggacctttc | acaaaattca | caagggtgta | taccaagagc | tccctaactc | ggatcctgct | 660 |
| gacccaaact | cggatcctgc | tgacctaatt | ttccaaaaag | actatcttga | atatggtgaa | 720 |
| atcctgcctt | ttcctgagtc | tcagttagta | gagtttaaac | agttctctac | aaaacacttc | 780 |
| caagaatatg | taaaaaggac | aattccagaa | tacgtccctg | catttgcaaa | cactggagga | 840 |
| ggctatcttt | ttattggagt | ggatgataag | agtagggaag | tcctgggatg | tgcaaaagaa | 900 |
| aatgttgacc | ctgactcttt | gagaaggaaa | atagaacaag | ccatatacaa | actaccttgt | 960 |
| gttcattttt | gccaaccca | acgcccgata | accttcacac | tcaaaattgt | ggatgtgtta | 1020 |
| aaaaggggag | agctctatgg | ctatgcttgc | atgatcagag | taaatccctt | ctgctgtgca | 1080 |
| gtgttctcag | aagctcccaa | ttcatggata | gtggaggaca | agtacgtctg | cagcctgaca | 1140 |
| accgagaaat | gggtaggcat | gatgacagac | acagatccag | atcttctaca | gttgtctgaa | 1200 |
| gattttgaat | gtcagctgag | tctatctagt | gggcctcccc | ttagcagacc | agtgtactcc | 1260 |
| aagaaaggcc | tggaacataa | aaaggaactc | cagcaacttt | tattttcagt | cccaccagga | 1320 |
| tatttgcgat | atactccaga | gtcactctgg | agggacctga | tctcagagca | cagaggacta | 1380 |
| gaggagttaa | taaataagca | aatgcaacct | ttctttcggg | gaattttgat | cttctctaga | 1440 |
| agtttgggctg | tggacctgaa | cttgcaggag | aagccaggag | tcatctgtga | tgctctgctg | 1500 |
| atagcacaga | acagcacccc | cattctctac | accattctca | gggagcagga | tgcagagggc | 1560 |
| caggactact | gcactcgcac | tgcctttact | ttgaagcaga | agctagtgaa | catgggggggc | 1620 |
| tacaccggga | aggtgtgtgt | cagggccaag | gtcctctgcc | tgagtcctga | gagcagcgca | 1680 |
| gaggccttgg | aggctgcagt | gtctccgatg | gattaccctg | cgtcctatag | ccttgcaggc | 1740 |
| acccagcaca | tggaagccct | gctgcagtcc | ctcgtgattg | tcttactcgg | cttcaggtct | 1800 |
| ctcttgagtg | accagctcgg | ctgtgaggtt | ttaaatctgc | tcacagccca | gcagtatgag | 1860 |
| atattctcca | gaagcctccg | caagaacaga | gagttgtttg | tccacggctt | acctggctca | 1920 |
| gggaagacca | tcatggccat | gaagatcatg | gagaagatca | ggaatgtgtt | tcactgtgag | 1980 |
| gcacacagaa | ttctctacgt | ttgtgaaaac | cagcctctga | ggaactttat | cagtgataga | 2040 |
| aatatctgcc | gagcagagac | ccggaaaact | ttcctaagag | aaaactttga | acacattcaa | 2100 |

```
cacatcgtca ttgacgaagc tcagaatttc cgtactgaag atggggactg gtatgggaag    2160
gcaaaaagca tcactcggag agcaaagggt ggcccaggaa ttctctggat ctttctggat    2220
tactttcaga ccagccactt ggattgcagt ggcctccctc ctctctcaga ccaatatcca    2280
agagaagagc tcaccagaat agttcgcaat gcagatccaa tagccaagta cttacaaaaa    2340
gaaatgcaag taattagaag taatccttca tttaacatcc ccactgggtg cctcgaggta    2400
tttcctgaag ccgaatggtc ccagggtgtt cagggaacct tacgaattaa gaaatacttg    2460
actgtggagc aaataatgac ctgtgtggca gacacgtgca ggcgcttctt tgatagggc    2520 tattctccaa aggatgttgc tgtgcttgtc agcaccgcaa agaagtgga gcactataag    2580 tatgagctct tgaaagcaat gaggaagaaa agggtggtgc agctcagtga tgcatgtgat    2640
atgttgggtg atcacattgt gttggacagt gttcggcgat tctcaggcct ggaaaggagc    2700
atagtgtttg ggatccatcc aaggacagct gacccagcta tcttacccaa tgttctgatc    2760
tgtctggctt ccagggcaaa acaacacctg tatatttttc cgtggggtgg ccattaggaa    2820
gaactccaaa tcaaaatgct atgtaaatgt ctatgggtga cagtctgctg atggtagaaa    2880
cctttctttt tagttcacaa gtcagagatt tggacggagc tgacacaaag agtttggagc    2940
tcccccattt ctggctctcc tttcagggt tccttcccca acccttttca gcagcggtgg    3000 ctgccccca ttctgacccc tgactcttcc agccagaaag atggtggttt tctaaaggaa    3060
ctttagctgt cctgcacaat gccgatctgt gtcttgcatt tgggtaaaa gccataaaaa    3120 taagaaactc agcctgtggc ctttcttct ccaaggctg ggcttctttt tttaagtgac    3180
ttcatgcagt ttgttgcttt taaaaatttg tccagaatcg ttttctgcag aagcatggtc    3240
tgttaggagc ttactggccg tagcagaagc aattgttcc tgaattcttg acatttatct    3300
ttgctgtatt catttagggc ttgggagagt ccgaagataa ttcagtcact gtcagattaa    3360
taattctgtc aggacaaaga ataccgttat gattatttaa tccttttaaaa ttgtggtctc    3420 cagagcttgt tctcagaatg gcccagacca agccttaatt gtgatagtga atattaatgg    3480
tcactttaag gagaaattat aggccaagat gaaatgaaca taaacctgtt tgccctggct    3540
ttcagtggaa gatgatatta gagaccaaaa tctggttctg aaggtgtgta tcagccctaa    3600
ggtgaaccag acttgggaaa gattgtcttt aaaaatcaat gagtttatgt tttaacttct    3660
cagcttagtt ctatgcattg ctctataaca cacctagtta agtttatgt tattcttgaa    3720 ctgtgatttt ttttctattt actttcatgg tttggtgggc cattgttatg gactgaatgt    3780
ttgtgtccca cccttcaccc ccaaattccc gtgttgaagc cccaacctgc actgtggagc    3840
tggggctgct aaggaagtaa ttaaggttac atgaagtcat ggtggggctc tgatctgcta    3900
aggttggtgt ccttataggg agagaccca gagagcttgt tccctccctc cctgtgcatg    3960
caaacaagag ggcatgggag cacacagaga gatggcagcc acctacaagc caagaggaga    4020
agcctcacaa tcaaactctc gctgctggcg agagtcttgg actctgtctt ggacttccag    4080
cctccagact gtgagaaaca aatttctgtt gtttcagctt tcagtctct ggtgttttgt    4140 tattgcagcc tgagaacaca gctgtacgat tatttgtcaa acagaaaaca ctgatactta    4200
acaatgctaa tgcaattatt tatttgcttt tcagtctcta caaacgttc taaaacacta    4260 atctaaatat taacagtaaa atatttgcat aactaatgga aactaagaaa tcatatgacc    4320
aatatttcac ttattggtaa tcttactcta ctgatttccc cccagactgt gattttgaa    4380 cttccttgcc tttctcctgt ctttctgtgt ttattcatgg aattccagtt atctgggctt    4440
gaaattgcag gctctcctaa cttaagcaaa atctgacaga tcagcaaaat gagataaatg    4500
```

```
tttcttttttt ctttctgact gcattaaatc agatacaact cagcattaaa aagctatctt    4560
tgtaaatgtt gttactaata aattagtctt ataagatccc tggactttgg agttgttgca    4620
```

<210> SEQ ID NO 9
<211> LENGTH: 379
<212> TYPE: PRT
<213> ORGANISM: Homo sapiens

<400> SEQUENCE: 9

Met Ala Ala Ala Ala Gln Gly Gly Gly Glu Pro Arg Arg
1               5                   10                  15

Thr Glu Gly Val Gly Pro Gly Val Pro Gly Glu Val Glu Met Val Lys
            20                  25                  30

Gly Gln Pro Phe Asp Val Gly Pro Arg Tyr Thr Gln Leu Gln Tyr Ile
        35                  40                  45

Gly Glu Gly Ala Tyr Gly Met Val Ser Ser Ala Tyr Asp His Val Arg
    50                  55                  60

Lys Thr Arg Val Ala Ile Lys Lys Ile Ser Pro Phe Glu His Gln Thr
65                  70                  75                  80

Tyr Cys Gln Arg Thr Leu Arg Glu Ile Gln Ile Leu Leu Arg Phe Arg
                85                  90                  95

His Glu Asn Val Ile Gly Ile Arg Asp Ile Leu Arg Ala Ser Thr Leu
            100                 105                 110

Glu Ala Met Arg Asp Val Tyr Ile Val Gln Asp Leu Met Glu Thr Asp
        115                 120                 125

Leu Tyr Lys Leu Leu Lys Ser Gln Gln Leu Ser Asn Asp His Ile Cys
    130                 135                 140

Tyr Phe Leu Tyr Gln Ile Leu Arg Gly Leu Lys Tyr Ile His Ser Ala
145                 150                 155                 160

Asn Val Leu His Arg Asp Leu Lys Pro Ser Asn Leu Leu Ile Asn Thr
                165                 170                 175

Thr Cys Asp Leu Lys Ile Cys Asp Phe Gly Leu Ala Arg Ile Ala Asp
            180                 185                 190

Pro Glu His Asp His Thr Gly Phe Leu Thr Glu Tyr Val Ala Thr Arg
        195                 200                 205

Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Glu Pro Phe Thr Phe Ala Met Glu Leu
            340                 345                 350

Asp Asp Leu Pro Lys Glu Arg Leu Lys Glu Leu Ile Phe Gln Glu Thr
    355                 360                 365

Ala Arg Phe Gln Pro Gly Val Leu Glu Ala Pro
    370                 375

<210> SEQ ID NO 10
<211> LENGTH: 1866
<212> TYPE: DNA
<213> ORGANISM: Homo sapiens

<400> SEQUENCE: 10

| | | | | | |
|---|---|---|---|---|---|
| cgttcctcgg | cgccgccggg | gccccagagg | gcagcggcag | caacagcagc | agcagcagca | 60 |
| gcgggagtgg | agatggcggc | ggcggcggct | caggggggcg | ggggcgggga | gccccgtaga | 120 |
| accgaggggg | tcggcccggg | ggtcccgggg | gaggtggaga | tggtgaaggg | gcagccgttc | 180 |
| gacgtgggcc | cgcgctacac | gcagttgcag | tacatcggcg | agggcgcgta | cggcatggtc | 240 |
| agctcggcct | atgaccacgt | gcgcaagact | cgcgtggcca | tcaagaagat | cagccccttc | 300 |
| gaacatcaga | cctactgcca | gcgcacgctc | cgggagatcc | agatcctgct | gcgcttccgc | 360 |
| catgagaatg | tcatcggcat | ccgagacatt | ctgcgggcgt | ccaccctgga | agccatgaga | 420 |
| gatgtctaca | ttgtgcagga | cctgatggag | actgacctgt | acaagttgct | gaaaagccag | 480 |
| cagctgagca | atgaccatat | ctgctacttc | ctctaccaga | tcctgcgggg | cctcaagtac | 540 |
| atccactccg | ccaacgtgct | ccaccgagat | ctaaagccct | ccaacctgct | cagcaacacc | 600 |
| acctgcgacc | ttaagatttg | tgatttcggc | ctggcccgga | ttgccgatcc | tgagcatgac | 660 |
| cacaccggct | tcctgacgga | gtatgtggct | acgcgctggt | accgggcccc | agagatcatg | 720 |
| ctgaactcca | agggctatac | caagtccatc | gacatctggt | ctgtgggctg | cattctggct | 780 |
| gagatgctct | ctaaccggcc | catcttccct | ggcaagcact | acctggatca | gctcaaccac | 840 |
| attctgggca | tcctgggctc | cccatcccag | gaggacctga | attgtatcat | caacatgaag | 900 |
| gcccgaaact | acctacagtc | tctgccctcc | aagaccaagg | tggcttgggc | caagcttttc | 960 |
| cccaagtcag | actccaaagc | ccttgacctg | ctggaccgga | tgttaacctt | taaccccaat | 1020 |
| aaacggatca | cagtggagga | agcgctggct | caccccctacc | tggagcagta | ctatgacccg | 1080 |
| acggatgagc | cagtggccga | ggagcccttc | accttcgcca | tggagctgga | tgacctacct | 1140 |
| aaggagcggc | tgaaggagct | catcttccag | gagacagcac | gcttccagcc | cggagtgctg | 1200 |
| gaggccccct | agcccagaca | gacatctctg | caccctgggg | cctggacctg | cctcctgcct | 1260 |
| gcccctctcc | cgccagactg | ttagaaaatg | gacactgtgc | ccagcccgga | ccttggcagc | 1320 |
| ccaggccggg | gtggagcatg | ggcctggcca | cctctctcct | ttgctgaggc | ctccagcttc | 1380 |
| aggcaggcca | aggccttctc | ctccccaccc | gccctcccca | cggggcctcg | ggagctcagg | 1440 |
| tggcccccagt | tcaatctccc | gctgctgctg | ctgctgcgcc | cttaccttcc | ccagcgtccc | 1500 |
| agtctctggc | agttctggaa | tggaagggtt | ctggctgccc | caacctgctg | aagggcagag | 1560 |
| gtggagggtg | gggggcgctg | agtagggact | cagggccatg | cctgcccccc | tcatctcatt | 1620 |
| caaaccccac | cctagtttcc | ctgaaggaac | attccttagt | ctcaagggct | agcatccctg | 1680 |
| aggagccagg | ccgggccgaa | tccccctcccct | gtcaaagctg | tcacttcgcg | tgccctcgct | 1740 |
| gcttctgtgt | gtggtgagca | gaagtggagc | tgggggggcgt | ggagagcccg | gcgcccctgc | 1800 |
| cacctcccctg | acccgtctaa | tatataaata | tagagatgtg | tctatggctg | aaaaaaaaaa | 1860 |
| aaaaaa | | | | | | 1866 |

```
<210> SEQ ID NO 11
<211> LENGTH: 1290
<212> TYPE: PRT
<213> ORGANISM: Homo sapiens

<400> SEQUENCE: 11
```

| | | | | | | | | | | | | | | |
|---|---|---|---|---|---|---|---|---|---|---|---|---|---|---|
| Met | Ala | Gly | Ala | Ala | Ser | Pro | Cys | Ala | Asn | Gly | Cys | Gly | Pro | Gly |Ala |
| 1 | | | | 5 | | | | | 10 | | | | | 15 |

Met Ala Gly Ala Ala Ser Pro Cys Ala Asn Gly Cys Gly Pro Gly Ala
1               5                   10                  15

Pro Ser Asp Ala Glu Val Leu His Leu Cys Arg Ser Leu Glu Val Gly
                20                  25                  30

Thr Val Met Thr Leu Phe Tyr Ser Lys Lys Ser Gln Arg Pro Glu Arg
            35                  40                  45

Lys Thr Phe Gln Val Lys Leu Glu Thr Arg Gln Ile Thr Trp Ser Arg
50                  55                  60

Gly Ala Asp Lys Ile Glu Gly Ala Ile Asp Ile Arg Glu Ile Lys Glu
65                  70                  75                  80

Ile Arg Pro Gly Lys Thr Ser Arg Asp Phe Asp Arg Tyr Gln Glu Asp
                85                  90                  95

Pro Ala Phe Arg Pro Asp Gln Ser His Cys Phe Val Ile Leu Tyr Gly
                100                 105                 110

Met Glu Phe Arg Leu Lys Thr Leu Ser Leu Gln Ala Thr Ser Glu Asp
            115                 120                 125

Glu Val Asn Met Trp Ile Lys Gly Leu Thr Trp Leu Met Glu Asp Thr
130                 135                 140

Leu Gln Ala Pro Thr Pro Leu Gln Ile Glu Arg Trp Leu Arg Lys Gln
145                 150                 155                 160

Phe Tyr Ser Val Asp Arg Asn Arg Glu Asp Arg Ile Ser Ala Lys Asp
                165                 170                 175

Leu Lys Asn Met Leu Ser Gln Val Asn Tyr Arg Val Pro Asn Met Arg
            180                 185                 190

Phe Leu Arg Glu Arg Leu Thr Asp Leu Glu Gln Arg Ser Gly Asp Ile
        195                 200                 205

Thr Tyr Gly Gln Phe Ala Gln Leu Tyr Arg Ser Leu Met Tyr Ser Ala
210                 215                 220

Gln Lys Thr Met Asp Leu Pro Phe Leu Glu Ala Ser Thr Leu Arg Ala
225                 230                 235                 240

Gly Glu Arg Pro Glu Leu Cys Arg Val Ser Leu Pro Glu Phe Gln Gln
                245                 250                 255

Phe Leu Leu Asp Tyr Gln Gly Glu Leu Trp Ala Val Asp Arg Leu Gln
            260                 265                 270

Val Gln Glu Phe Met Leu Ser Phe Leu Arg Asp Pro Leu Arg Glu Ile
        275                 280                 285

Glu Glu Pro Tyr Phe Phe Leu Asp Glu Phe Val Thr Phe Leu Phe Ser
290                 295                 300

Lys Glu Asn Ser Val Trp Asn Ser Gln Leu Asp Ala Val Cys Pro Asp
305                 310                 315                 320

Thr Met Asn Asn Pro Leu Ser His Tyr Trp Ile Ser Ser Ser His Asn
                325                 330                 335

Thr Tyr Leu Thr Gly Asp Gln Phe Ser Ser Glu Ser Ser Leu Glu Ala
            340                 345                 350

Tyr Ala Arg Cys Leu Arg Met Gly Cys Arg Cys Ile Glu Leu Asp Cys
        355                 360                 365

Trp Asp Gly Pro Asp Gly Met Pro Val Ile Tyr His Gly His Thr Leu
370                 375                 380

-continued

```
Thr Thr Lys Ile Lys Phe Ser Asp Val Leu His Thr Ile Lys Glu His
385                 390                 395                 400

Ala Phe Val Ala Ser Glu Tyr Pro Val Ile Leu Ser Ile Glu Asp His
            405                 410                 415

Cys Ser Ile Ala Gln Gln Arg Asn Met Ala Gln Tyr Phe Lys Lys Val
        420                 425                 430

Leu Gly Asp Thr Leu Leu Thr Lys Pro Val Glu Ile Ser Ala Asp Gly
            435                 440                 445

Leu Pro Ser Pro Asn Gln Leu Lys Arg Lys Ile Leu Ile Lys His Lys
    450                 455                 460

Lys Leu Ala Glu Gly Ser Ala Tyr Glu Val Pro Thr Ser Met Met
465                 470                 475                 480

Tyr Ser Glu Asn Asp Ile Ser Asn Ser Ile Lys Asn Gly Ile Leu Tyr
                485                 490                 495

Leu Glu Asp Pro Val Asn His Glu Trp Tyr Pro His Tyr Phe Val Leu
            500                 505                 510

Thr Ser Ser Lys Ile Tyr Tyr Ser Glu Thr Ser Ser Asp Gln Gly
        515                 520                 525

Asn Glu Asp Glu Glu Pro Lys Val Ser Ser Thr Glu Leu
530                 535                 540

His Ser Asn Glu Lys Trp Phe His Gly Lys Leu Gly Ala Gly Arg Asp
545                 550                 555                 560

Gly Arg His Ile Ala Glu Arg Leu Leu Thr Glu Tyr Cys Ile Glu Thr
            565                 570                 575

Gly Ala Pro Asp Gly Ser Phe Leu Val Arg Glu Ser Glu Thr Phe Val
            580                 585                 590

Gly Asp Tyr Thr Leu Ser Phe Trp Arg Asn Gly Lys Val Gln His Cys
            595                 600                 605

Arg Ile His Ser Arg Gln Asp Ala Gly Thr Pro Lys Phe Phe Leu Thr
            610                 615                 620

Asp Asn Leu Val Phe Asp Ser Leu Tyr Asp Leu Ile Thr His Tyr Gln
625                 630                 635                 640

Gln Val Pro Leu Arg Cys Asn Glu Phe Glu Met Arg Leu Ser Glu Pro
            645                 650                 655

Val Pro Gln Thr Asn Ala His Glu Ser Lys Glu Trp Tyr His Ala Ser
            660                 665                 670

Leu Thr Arg Ala Gln Ala Glu His Met Leu Met Arg Val Pro Arg Asp
            675                 680                 685

Gly Ala Phe Leu Val Arg Lys Arg Asn Glu Pro Asn Ser Tyr Ala Ile
    690                 695                 700

Ser Phe Arg Ala Glu Gly Lys Ile Lys His Cys Arg Val Gln Gln Glu
705                 710                 715                 720

Gly Gln Thr Val Met Leu Gly Asn Ser Glu Phe Asp Ser Leu Val Asp
            725                 730                 735

Leu Ile Ser Tyr Tyr Glu Lys His Pro Leu Tyr Arg Lys Met Lys Leu
            740                 745                 750

Arg Tyr Pro Ile Asn Glu Glu Ala Leu Glu Lys Ile Gly Thr Ala Glu
            755                 760                 765

Pro Asp Tyr Gly Ala Leu Tyr Glu Gly Arg Asn Pro Gly Phe Tyr Val
    770                 775                 780

Glu Ala Asn Pro Met Pro Thr Phe Lys Cys Ala Val Lys Ala Leu Phe
785                 790                 795                 800

Asp Tyr Lys Ala Gln Arg Glu Asp Glu Leu Thr Phe Ile Lys Ser Ala
```

```
                805                 810                 815
Ile Ile Gln Asn Val Glu Lys Gln Glu Gly Gly Trp Trp Arg Gly Asp
            820                 825                 830

Tyr Gly Gly Lys Lys Gln Leu Trp Phe Pro Ser Asn Tyr Val Glu Glu
            835                 840                 845

Met Val Asn Pro Val Ala Leu Glu Pro Glu Arg Glu His Leu Asp Glu
            850                 855                 860

Asn Ser Pro Leu Gly Asp Leu Leu Arg Gly Val Leu Asp Val Pro Ala
865                 870                 875                 880

Cys Gln Ile Ala Ile Arg Pro Glu Gly Lys Asn Asn Arg Leu Phe Val
                885                 890                 895

Phe Ser Ile Ser Met Ala Ser Val Ala His Trp Ser Leu Asp Val Ala
            900                 905                 910

Ala Asp Ser Gln Glu Glu Leu Gln Asp Trp Val Lys Lys Ile Arg Glu
            915                 920                 925

Val Ala Gln Thr Ala Asp Ala Arg Leu Thr Glu Gly Lys Ile Met Glu
            930                 935                 940

Arg Arg Lys Lys Ile Ala Leu Glu Leu Ser Glu Leu Val Val Tyr Cys
945                 950                 955                 960

Arg Pro Val Pro Phe Asp Glu Glu Lys Ile Gly Thr Glu Arg Ala Cys
                965                 970                 975

Tyr Arg Asp Met Ser Ser Phe Pro Glu Thr Lys Ala Gly Lys Tyr Val
            980                 985                 990

Asn Lys Ala Lys Gly Lys Lys Phe Leu Gln Tyr Asn Arg Leu Gln Leu
            995                 1000                1005

Ser Arg Ile Tyr Pro Lys Gly Gln Arg Leu Asp Ser Ser Asn Tyr
    1010                1015                1020

Asp Pro Leu Pro Met Trp Ile Cys Gly Ser Gln Leu Val Ala Leu
    1025                1030                1035

Asn Phe Gln Thr Pro Asp Lys Pro Met Gln Met Asn Gln Ala Leu
    1040                1045                1050

Phe Met Thr Gly Arg His Cys Gly Tyr Val Leu Gln Pro Ser Thr
    1055                1060                1065

Met Arg Asp Glu Ala Phe Asp Pro Phe Asp Lys Ser Ser Leu Arg
    1070                1075                1080

Gly Leu Glu Pro Cys Ala Ile Ser Ile Glu Val Leu Gly Ala Arg
    1085                1090                1095

His Leu Pro Lys Asn Gly Arg Gly Ile Val Cys Pro Phe Val Glu
    1100                1105                1110

Ile Glu Val Ala Gly Ala Glu Tyr Asp Ser Thr Lys Gln Lys Thr
    1115                1120                1125

Glu Phe Val Val Asp Asn Gly Leu Asn Pro Val Trp Pro Ala Lys
    1130                1135                1140

Pro Phe His Phe Gln Ile Ser Asn Pro Glu Phe Ala Phe Leu Arg
    1145                1150                1155

Phe Val Val Tyr Glu Glu Met Phe Ser Asp Gln Asn Phe Leu
    1160                1165                1170

Ala Gln Ala Thr Phe Pro Val Lys Gly Leu Lys Thr Gly Tyr Arg
    1175                1180                1185

Ala Val Pro Leu Lys Asn Asn Tyr Ser Glu Asp Leu Glu Leu Ala
    1190                1195                1200

Ser Leu Leu Ile Lys Ile Asp Ile Phe Pro Ala Lys Glu Asn Gly
    1205                1210                1215
```

```
Asp Leu Ser Pro Phe Ser Gly Thr Ser Leu Arg Glu Arg Gly Ser
    1220            1225                1230

Asp Ala Ser Gly Gln Leu Phe His Gly Arg Ala Arg Glu Gly Ser
    1235            1240                1245

Phe Glu Ser Arg Tyr Gln Gln Pro Phe Glu Asp Phe Arg Ile Ser
    1250            1255                1260

Gln Glu His Leu Ala Asp His Phe Asp Ser Arg Glu Arg Arg Ala
    1265            1270                1275

Pro Arg Arg Thr Arg Val Asn Gly Asp Asn Arg Leu
    1280            1285                1290

<210> SEQ ID NO 12
<211> LENGTH: 4408
<212> TYPE: DNA
<213> ORGANISM: Homo sapiens

<400> SEQUENCE: 12
```

| | | | | | |
|---|---|---|---|---|---|
| ggggtgccgc | cgccgccgtt | gcgcttgctc | ccgggcggtc | ctggcctgtg | ccgccgccgc | 60 |
| ccccagcgtc | ggagccatgg | cgggcgccgc | gtccccttgc | gccaacggct | gcgggcccgg | 120 |
| cgcgccctcg | gacgccgagg | tgctgcacct | ctgccgcagc | ctcgaggtgg | gcaccgtcat | 180 |
| gactttgttc | tactccaaga | agtcgcagcg | acccgagcgg | aagaccttcc | aggtcaagct | 240 |
| ggagacgcgc | cagatcacgt | ggagccgggg | cgccgacaag | atcgaggggg | ccattgacat | 300 |
| tcgtgaaatt | aaggagatcc | gcccagggaa | gacctcacgg | gactttgatc | gctatcaaga | 360 |
| ggacccagct | ttccggccgg | accagtcaca | ttgctttgtc | attctctatg | aatggaattt | 420 |
| tcgcctgaaa | acgctgagcc | tgcaagccac | atctgaggat | gaagtgaaca | tgtggatcaa | 480 |
| gggcttaact | tggctgatgg | aggatacatt | gcaggcaccc | acacccctgc | agattgagag | 540 |
| gtggctccgg | aagcagtttt | actcagtgga | tcggaatcgt | gaggatcgta | tatcagccaa | 600 |
| ggacctgaag | aacatgctgt | cccaggtcaa | ctaccgggtc | cccaacatgc | gcttcctccg | 660 |
| agagcggctg | acggacctgg | agcagcgcag | cggggacatc | acctacgggc | agtttgctca | 720 |
| gctgtaccgc | agcctcatgt | acagcgccca | gaagacgatg | gacctcccct | tcttggaagc | 780 |
| cagtactctg | agggctgggg | agcggccgga | gctttgccga | gtgtcccttc | ctgagttcca | 840 |
| gcagttcctt | cttgactacc | aggggagct | gtgggctgtt | gatcgcctcc | aggtgcagga | 900 |
| gttcatgctc | agcttcctcc | gagacccctt | acgagagatc | gaggagccat | acttcttcct | 960 |
| ggatgagttt | gtcaccttcc | tgttctccaa | agagaacagt | gtgtggaact | cgcagctgga | 1020 |
| tgcagtatgc | ccggacacca | tgaacaaccc | tcttccccac | tactggatct | cctcctcgca | 1080 |
| caacacgtac | ctgaccgggg | accagttctc | cagtgagtcc | tccttggaag | cctatgctcg | 1140 |
| ctgcctgcgg | atgggctgtc | gctgcattga | gttggactgc | tgggacggcc | cggatgggat | 1200 |
| gccagttatt | taccatgggc | acacccttac | caccaagatc | aagttctcag | atgtcctgca | 1260 |
| caccatcaag | gagcatgcct | tgtggcctc | agagtaccca | gtcatcctgt | ccattgagga | 1320 |
| ccactgcagc | attgcccagc | agagaaacat | ggcccaatac | ttcaagaagg | tgctggggga | 1380 |
| cacactcctc | accaagcccg | tggagatctc | tgccgacggg | ctcccctcac | ccaaccagct | 1440 |
| taagaggaag | atcctcatca | agcacaagaa | gctggctgag | ggcagtgcct | acgaggaggt | 1500 |
| gcctacatcc | atgatgtact | ctgagaacga | catcagcaac | tctatcaaga | atggcatcct | 1560 |
| ctacctggag | gaccctgtga | ccacgaatgt | gtatccccac | tactttgttc | tgaccagcag | 1620 |
| caagatctac | tactctgagg | agaccagcag | tgaccagggc | aacgaggatg | aggaggagcc | 1680 |

```
caaggaggtc agcagcagca cagagctgca ctccaatgag aagtggttcc atgggaagct    1740
aggggcaggg cgtgacgggc gtcacatcgc tgagcgcctg cttactgagt actgcatcga    1800
gaccggagcc cctgacggct ccttcctcgt gcgagagagt gagaccttcg tgggcgacta    1860
cacgctctct ttctggcgga acgggaaagt ccagcactgc cgtatccact cccggcaaga    1920
tgctgggacc cccaagttct tcttgacaga caacctcgtc tttgactccc tctatgacct    1980
catcacgcac taccagcagg tgcccctgcg ctgtaatgag tttgagatgc gactttcaga    2040
gcctgtccca cagaccaacg cccacgagag caaagagtgg taccacgcga gcctgaccag    2100
agcacaggct gagcacatgc taatgcgcgt ccctcgtgat ggggccttcc tggtgcggaa    2160
gcggaatgaa cccaactcat atgccatctc tttccgggct gagggcaaga tcaagcattg    2220
ccgtgtccag caagagggcc agacagtgat gctagggaac tcggagttcg acagccttgt    2280
tgacctcatc agctactatg agaaacaccc gctataccgc aagatgaagc tgcgctatcc    2340
catcaacgag gaggcactgg agaagattgg cacagctgag cctgactacg ggccctgta    2400 tgagggacgc aaccctggct tctatgtaga ggcaaaccct atgccaactt tcaagtgtgc    2460
agtcaaagcc ctctttgact acaaggccca gagggaggac gagctgacct tcatcaagag    2520
cgccatcatc cagaatgtgg agaagcaaga gggaggctgg tggcgagggg actacggagg    2580
gaagaagcag ctgtggttcc catcaaacta cgtggaagag atggtcaacc ccgtggccct    2640
ggagccggag agggagcact ggacgagaa cagcccccta ggggacttgc tgcgggggt    2700 cttggatgtg ccggcttgtc agattgccat ccgtcctgag ggcaagaaca accggctctt    2760
cgtcttctcc atcagcatgg cgtcggtggc ccactggtcc ctggatgttg ctgccgactc    2820
acaggaggag ctgcaggact gggtgaaaaa gatccgtgaa gtggcccaga cagcagacgc    2880
caggctcact gaagggaaga taatggaacg gaggaagaag attgccctgg agctctctga    2940
acttgtcgtc tactgccggc ctgttccctt tgatgaagag aagattggca cagaacgtgc    3000
ttgctaccgg gacatgtcat ccttcccgga aaccaaggct gagaaatacg tgaacaaggc    3060
caaaggcaag aagttccttc agtacaatcg actgcagctc tcccgcatct accccaaggg    3120
ccagcgactg gattcctcca actacgatcc tttgcccatg tggatctgtg gcagtcagct    3180
tgtggccctc aacttccaga cccctgacaa gcctatgcag atgaaccagg ccctcttcat    3240
gacgggcagg cactgtggct acgtgctgca gccaagcacc atgcgggatg aggccttcga    3300 ccccctttgac aagagcagcc tccgcgggct ggagccatgt gccatctcta ttgaggtgct    3360
gggggcccga catctgccaa agaatggccg aggcattgtg tgtccttttg tggagattga    3420
ggtggctgga gctgagtatg acagcaccaa gcagaagaca gagtttgtgg tggacaatgg    3480
actcaaccct gtatggccag ccaagccctt ccacttccag atcagtaacc ctgaatttgc    3540
ctttctgcgc ttcgtggtgt atgaggaaga catgtttagt gaccagaatt cctggctcaa    3600
ggctactttc ccagtaaaag gcctgaagac aggatacaga gcagtgcctt tgaagaacaa    3660
ctacagtgag gacctggagt tggcctccct gctgatcaag attgacattt tccctgccaa    3720
ggagaatggt gacctcagtc ccttcagtgg tacgtccctg cgggagcggg gctcagatgc    3780
ctcaggccag ctgtttcatg gccgagcccg ggaaggctcc tttgaatccc gctaccagca    3840
gccgtttgag gacttccgca tctcccagga gcatctcgca gaccattttg acagtcgaga    3900
acgaagggcc ccaagaagga ctcgggtcaa tggagacaac cgcctctagt tgtaccccag    3960
cctcgttgga gagcagcagg tgctgtgcgc cttgtagaat gccgcgaact gggttctttg    4020
```

```
gaagcagccc cctgtggcgg ccttccgggt ctcgcagcct gaagcctgga ttccagcagt     4080
gaatgctaga cagaaaccaa gccattaatg agatgttatt actgttttgg gcctccatgc     4140
cccagctctg gatgaaggca aaaactgtac tgtgtttcgc attaagcaca cacatctggc     4200
cctgacttct ggagatggat ccttccatct tgtggggcca ggaccatggc cgaagcccct     4260
tggagagaga ggctgcctca gccagtggca caggagactc caaggagcta ctgacattcc     4320
taagagtgga ggaggaggag gagccttgct gggccaggga aacaaagttt acattgtcct     4380
gtagctttaa aaccacagct gggcaggg                                        4408
```

BIOMARKERS FOR CANCER

CROSS REFERENCE TO RELATED APPLICATIONS

This application is a national phase entry pursuant to 35 U.S.C. § 371 of International Application No. PCT/EP2016/066357, filed Jul. 8, 2016, which claims the benefit of priority of Application No. GB 1512133.8, filed Jul. 10, 2015, each of which is incorporated by reference herein in its entirety for any purpose.

FIELD OF INVENTION

This invention relates to the fields of drug development and cancer treatment. In particular this invention relates to the field of cancer biomarkers and more particularly to methods of prognosing and treating cancer.

BACKGROUND TO THE INVENTION

The Epithelial-Mesenchymal Transition (EMT)

Epithelial tissues make up one of the four basic tissue types of the body, along with connective tissue, muscle and nervous tissue. Epithelial cells are characterised by a tendency to form into sheets of polarised cells held together by strong intercellular junctions. As a consequence of this, epithelial cells are not able to move freely and show little migration compared to other cell types. In contrast, mesenchymal-like cells (e.g. fibroblasts) lack strong intercellular junctions and can move as individual cells. They can be highly motile and able to migrate through the extracellular matrix.

The Epithelial-Mesenchymal Transition (EMT) is a natural cellular program in which individual epithelial cells lose the gene expression patterns and behaviours characteristic of epithelial cells and instead begin to look, behave and express genes typical of mesenchymal cells. In so doing they lose adhesion and apical-basal polarity and gain the ability to migrate and invade the extracellular matrix. EMT is not irreversible. A mirror process called Mesenchymal-Epithelial Transition (MET) results in the loss of mesenchymal characteristics and re-establishment of cell-cell adhesion and apical-basal polarity.

EMT is especially important during embryonic development. It plays a fundamental role in gastrulation, where an embryo consisting of a single epithelial cell layer develops into one with the three classical germ layers, ectoderm, mesoderm and endoderm. Slightly later in vertebrate development, EMT gives rise to the neural crest cells. These cells migrate throughout the embryo and give rise to many different structures including ganglia of the peripheral nervous system, bone and cartilage of the face and head, pigment cells and glial cells. Further rounds of MET and EMT are essential for the formation of internal organs from both the mesoderm and endoderm.

EMT and Disease

In contrast to its importance during embryonic development, the EMT program is seldom activated in healthy adults. It is, however, induced in response to inflammation following injury or disease: EMT plays a role in wound healing and tissue repair, and occurs during organ degenerative disease (e.g. fibrotic diseases such as renal, pulmonary or hepatic fibrosis).

EMT is also increasingly understood to play a key role in cancer metastasis. Carcinomas are epithelial cancers, and, in order for metastasis to occur, individual cells must escape the primary tumour and undergo a series of migrations. These include migration from the primary tumour into the local circulatory or lymphatic system, and extravasation from the vasculature and establishment at the site of metastasis. There is now good and growing evidence that interactions between tumour cells and their microenvironment can lead to induction of EMT in some of the tumour cells. The resulting increased cell migration and invasion potential of these cells then enhances the likelihood of a metastasis becoming established. The receptor tyrosine kinase Axl, which is a chronic myelogenous leukemia-associated oncogene, has recently been shown to be an essential EMT-induced effector in the invasion-metastasis cascade (WO2010/103388).

As well as this role in increasing metastatic potential, the EMT program has recently been linked with Cancer Stem Cells (CSCs). These cells were first identified in acute myelocytic leukemia (AML), and have been postulated to represent a subset of tumour cells with stem cell characteristics—i.e. the ability to give rise to all the cell types found in a particular cancer, and thus the ability to form a new tumour. Although they may represent only a tiny fraction of the cells in a tumour, CSCs are thought to be particularly resistant to existing anti-cancer drugs. Even though drug treatment may kill the vast majority of cells in the tumour, a single surviving CSC can therefore lead to a relapse of the disease. Recent evidence suggests an overlap between EMT and CSC phenotypes, suggesting that EMT may also play a role in recurrence of cancer after chemotherapy and the development of drug-resistant tumours in cancer, including AML.

Acute Myeloid Leukemia (AML)

Acute myeloid leukemia (AML) is a clonal disease of hematopoietic progenitors that is characterized by numerous heterogeneous genetic changes that alter the cells' normal mechanisms of proliferation, differentiation and cell death (Burnett et al., 2011). Currently, most AML patients are treated with chemotherapy such as Cytarabine. Apart from the BCR-Abl targeting drug Gleevec for treatment of chronic myelogenous leukemia (CML) and the differentiation-inducing drug ATRA for treatment of acute promyelocytic leukemia (APL), targeted therapy has so far been extensively lacking in the field of leukemia. This despite AML being a well characterized disease with several mutated oncogenes that could potentially be therapeutic targets (Haferlach, 2008).

Accordingly, robust biomarkers for the EMT phenotype would be useful in identifying patients at particular risk of developing metastatic or drug-resistant cancer, including AML, while novel drugs that target cells that have undergone EMT will reduce metastasis and relapse following conventional therapy.

SUMMARY OF THE INVENTION

The present inventors have identified and evaluated markers whose expression is regulated by Axl receptor tyrosine kinase signalling. More specifically, it has been found that levels of biomarker expression are altered in several acute myeloid leukemia (AML) cell lines and in vivo models upon exposure to the Axl inhibitor BGB324/R428. Accordingly, expression of one or more of these biomarkers can be used as an indicator of Axl receptor tyrosine kinase signalling in the applications described herein. Also contemplated are panels comprising two or more of the biomarkers disclosed herein, offering increased sensitivity and reliability in assessing Axl receptor tyrosine kinase signalling.

The demonstration of the link between Axl receptor tyrosine kinase signalling and biomarker expression identifies the biomarker as part of the Axl signalling cascade. Thus, the current studies have identified the biomarkers as potential new targets for intervention and treatment of conditions in which the Axl pathway plays a role.

Furthermore, the relationship between the biomarkers and Axl expression allows for the use of the biomarkers in the diagnosis or prognosis of Axl-related diseases and diseases characterized by proliferative activity, particularly in individuals being treated with Axl or Akt3 inhibitors.

In some embodiments the one or more biomarkers is, or includes, PHGDH.

Biomarkers

PHGDH

PHGDH is an enzyme which is involved in the early steps of L-serine synthesis. L-serine is required for D-serine and other amino acid synthesis. L-serine is also the major source of one-carbon units for methylation via generation of S-adenosylmethionine and is required for the production of proteins and phosphatidylserine (Kalhan et al., JBC, vol. 287, pp. 19786-19791 (2012)). Specifically, the enzyme catalyzes the transition of 3-phosphoglycerate into 3-phosphohydroxypyruvate, which is the first and rate-limiting step in the phosphorylated pathway of serine biosynthesis, using NAD+/NADH as a cofactor (Cho et al., Gene. 2000 Mar. 7; 245(1):193-201).

It is known that PHGDH plays a role in cancer progression, and PHGDH has been found to be amplified in a significant subset of tumors, including 6% of breast cancers, 40% of melanomas and 70% of estrogen receptor-negative breast tumors (ref: PMID 21804546 and 21760589). PHGDH is involved in metabolic reprograming of cancer cells. It is the enzyme that catalyses the first step in the serine biosynthesis pathway, and cancer cells with high PHGDH expression have increased serine synthesis flux, which supports high proliferation and tumor growth. Tumor cells with high PHGDH expression are using a "metabolic side street", diverting flux away from the more common metabolic pathway of cancer cells, glycolysis (the Warburgh effect) (DeBerardinis R J., Cell Metab. 2011 Sep. 7; 14(3):285-6).

PHGDH has been linked with some cancer types. For example, Teng et al. (Br J Cancer. 2014 Jan. 7; 110(1):123-32) identified PHGDH as one of 16 candidate circulating cisplatin-resistant biomarkers from epithelial ovarian carcinoma cell secretomes (proteins secreted from the cells). PHGDH was found in the human plasma proteome and in tissue interstinal fluid (Teng ibid.). Jing et al (Int J Gynecol Cancer. 2013 October; 23(8):1465-9) suggests that PHGDH may have use as a marker and/or therapeutic target in cervical cancer. However, until the work of the present inventors, no connection has been made between PHGDH and Axl signalling, nor has PHGDH been suggested as having a role in AML.

An example PHGDH (human) amino acid and mRNA sequence is set out below in the 'Sequences section'.

Axl

Axl is a member of the TAM (Tyro-Axl-Mer) family of transmembrane receptor tyrosine kinases (RTK), which regulates a large range of cellular responses (Hafizi and Dahlback, 2006). Axl, in particular, is expressed in embryonic tissues and plays a role in neural and mesenchymal development. Increased Axl expression or activation is a characteristic of various disease states.

Studies have shown that Axl plays a number of different roles in tumour formation. Axl is a key regulator of angiogenic behaviours including endothelial cell migration, proliferation and tube formation. Axl is also required for human breast carcinoma cells to form a tumour in vivo, indicating that Axl regulates processes that are vital for both neovascularisation and tumorigenesis (Holland S. et al, Cancer Res 2005; 65 (20), Oct. 15, 2005).

The activity of Axl receptor tyrosine kinase is positively correlated with tumour metastasis. More specifically, studies have shown that Axl enhances expression of MMP-9, which is required for Axl-mediated invasion. Axl promotes cell invasion by inducing MMP-9 acitivity through activation of NF-BK and Brg-1 (Tai, K-Y et al, Oncogene (2008), 27, 4044-4055).

Axl is overexpressed in human glioma cells and can be used to predict poor prognosis in patients with Glioblastoma Multiforme (GBM) (Vajkoczy P. et al, PNAS, Apr. 11, 2006, val 103, no. 15, 5799-5804; Hutterer M. et al, Clinical Cancer Res 2008; 14 (1) Jan. 1, 2008). Axl is also relatively overexpressed in highly invasive lung cancer cell lines compared to their minimally invasive counterparts (Shieh, Y-S et al, Neoplasia, val 7, no. 12, December 2005, 1058-1064). Axl is therefore believed to play an important role in tumour invasion and progression.

Likewise, Axl is expressed in highly invasive breast cancer cells, but not in breast cancer cells of low invasivity. More specifically, inhibition of Axl signalling (by dominant-negative Axl mutant, an antibody against the extracellular domain of Axl, or by short hairpin RNA knockdown of Axl) decreased the motility and invasivity of highly invasive breast cancer cells. Small molecule Axl inhibitors interfered with motility and invasivity of breast cancer cells. Thus, Axl is understood to be a critical element in the signalling network that governs the motility/invasivity of breast cancer cells (Zhang, Y-X et al., Cancer Res 2008; 68 (6), Mar. 15, 2008).

The Axl pathway has also been implicated in organ degenerative diseases such as fibrosis of the liver and/or kidney. For example, it has been shown in mice that a deficiency of the Axl ligand Gas6 prevents liver inflammation and fibrosis [Fourcot, A. et al., Am J Physiol Gastrointest Liver Physiol 300: G1043-G1053, 2011].

Axl is also upregulated and constitutively active in human AML (Park et al., 2013). Furthermore, Axl was recently identified as an independent prognostic marker and a potential new therapeutic target in AML (Ben-Batalla et al., 2013). Axl upregulation is also reported to result in constitutive activation of the receptor tyrosine kinase Flt3, both in the wild type form and in Flt3 with an internal tandem duplication (ITD) mutation (Park et al., 2013). About 30% of AML patients carry an ITD mutation in the Flt3 kinase. Flt3-ITD is an independent prognostic marker and is coupled to poor prognosis and therapeutic resistance in AML (Vardiman et al., 2009). So far, no Flt3 inhibitor has been successfully implemented in the clinical treatment of AML (Levis, 2013).

An example Axl (human) amino acid and mRNA sequence is set out below in the 'Sequences section'.

Akt

Akt (Protein kinase B) is a serine/threonine protein kinase that is known to be involved in diverse cellular processes including proliferation, motility, growth, glucose homeostasis, survival and cell death. Akt is one of the three principal components of the PI3K/Akt pathway (phosphatdylinositol 3-kinase, its antagonist PTEN and Akt). Mutation in components of this pathway are among the most frequently observed mutations in cancers and are found in up to 70% of breast cancers. In humans, there are three Akt family members, Akt 1, Akt 2 and Akt3 which are transcribed from different genes. The majority of research publications on Akt refer either to Akt1 or to Akt without specifying which family member, a consequence of the widespread use of pan-Akt antibodies that do not distinguish between the family members. Of the three isoforms, least is known about Akt3. Indeed, in a recent review article "Key signalling nodes in mammary gland development and cancer. Signalling downstream of PI3 kinase in mammary epithelium: a play in 3 Akts" (Wickenden J A and Watson C J, Breast Cancer Research 2010, 12, 202), Akt3 is mentioned just three times: once to establish its existence, once to note that it appears to have a minor role in normal mammary gland development and once to note that it does not affect Stat5a phosphorylation during pregnancy and lactation.

The roles for Akt1, Akt2 and Akt3 in normal development have been studied in knock-out mice, revealing that Akt1 is important for overall growth (knock-out mice are generally healthy but have reduced growth), Akt2 is primarily involved in glucose metabolism (knockout mice grow normally but show insulin resistance) and Akt3 is important in brain development (see e.g. Dummler B, Hemmings B A. Physiological roles of PKB/Akt isoforms in development and disease. Biochem Soc Trans 2007; 35:231-5). A more general role for Akt1 and Akt2 is suggested by their widespread expression throughout the body, while Akt3 has more restricted expression in the brain, kidney and heart.

Akt is considered an attractive target for cancer therapy, and inhibition of Akt alone or in combination with standard cancer chemotherapeutics has been postulated to reduce the apoptotic threshold and preferentially kill cancer cells (Lindley C W, Curr Top Med Chem, 10, 458, 2010). A recent review of attempts to inhibit Akt members pinpoints Akt2 as the most commonly mutated family member in cancers and suggests that inhibition of Akt1 and Akt2 would be optimal (Mattmann M E et al "Inhibition of Akt with small molecules and biologics: historical perspective and current status of the patent landscape", Expert Opinion on Therapeutic Patents, 21, 1309, 2011). Many of the compounds covered in this review have poor selectivity for Akt compared to other kinases and generally focus on Akt1. Compounds reported in this review with selectivity between the different family members overwhelmingly inhibit Akt1 and/or Akt2 rather than Akt3.

Despite the overwhelming focus on Akt1 in the literature, Akt3 overexpression has been linked to several cancers including melanoma (Cancer Res. 2004 Oct. 1; 64(19):7002-10) and ovarian cancer (Cancer Discov. 2012 Jan. 1; 2(1): 56-67).

In AML, one disease-driving mutation is an internal tandem duplication (ITD) in the Flt3 kinase, resulting in constitutive activation of the kinase. ITD-Flt3 mutations are found in about 30% of all AML patients (Vardiman et al., 2009). The presence of the Flt3-ITD mutation constitutively activates Akt signaling in these cells, which drives cytokine-independent survival, cell cycle progression and proliferation (Brandts et al., 2005). Furthermore, Axl upregulation in AML is also reported to result in constitutive activation of Flt3, both in the wild type form and with Flt3-ITD (Park et al., 2013). Thus, Akt is connected both with Axl directly, and with Flt3, a disease driver in AML, lead us to investigate pAkt as a potential biomarker for BGB324-treatment in AML.

Several patent publications relate to the use of Akt3.

WO2010/091354 (H Lee Moffat Cancer Institute, Inc.) relates to methods of diagnosing cancer in a subject involving determining levels of expression of Tyrosine 176-phosphorylated AKT1 rather than AKT3.

US20120040842 (Baker, et al.) lists Akt3 amongst a vast array of genes that may be assessed to determine the prognosis of colorectal cancer. However, Akt3 is not selected as a preferred marker.

US20120028264 (Shaq, et al.) lists Akt3 {Table 3A} amongst a vast array of genes, expression levels of which may be determined in the assessing the likelihood of prostate cancer recurring in a subject. The significance of Akt3 is not specifically mentioned.

US20120021983 (Tsichlis, et al.) relates to a method of diagnosing or prognosing a potential cancer and progression of an existing cancer by assessing a subject's Akt isoform profile, especially the ratio of Akt1 to Akt2, by comparing that profile with a normal Akt isoform profile.

US20120003209 (The Translational Genomics Research Institute) relates to methods and kits used in the identification of invasive glioblastoma based upon the expression levels of Akt1 and Akt2. Akt3 mRNA expression was found to be high in non-neoplastic brain speciments and decreased in glial tumours [[0130]]. Furthermore Akt3 expression was found to be significantly higher in long term surviving patients.

U.S. Pat. No. 8,133,684 (Aebersold et al.) discloses methods of determining androgen responses in prostate cells, mentioning Akt3 in a long list of possible prostate cancer biomarkers.

An example Akt (human Akt3) amino acid and mRNA sequence is set out below in the 'Sequences section'.

Slfn11

Slfn11 (Schlafen family member 11) is a member of the Schlafen family of proteins, characterised by the presence of a Slfn-box domain of unknown function. The Slfn box lies near an AAA domain, which has been demonstrated in other proteins to be an ATP/GTP-binding motif. Slfn11 is a member of the group III Slfn's which have an additional Slfn-specific "SWADL"-domain of unknown function, a nuclear localisation signal and an RNA-helicase-like motif. This constellation of domains has led to suggestions that group III SLFN proteins are involved in processing of RNA in the nucleus [Mavrommatis et al., J Interferon Cytokine Res. April 2013; 33(4): 206-210].

SLFN11 is an interferon (IFN)-induced antiviral protein which acts as an inhibitor of retrovirus protein synthesis. The protein specifically abrogates the production of retroviruses such as human immunodeficiency virus 1 (HIV-1) by acting as a specific inhibitor of the synthesis of retroviruses encoded proteins in a codon-usage-dependent manner [Li M. et al., Nature. 2012; 491(7422):125-128.]. The mechanism by which this inhibition occurs was described, and appears to involve blocking expression of viral proteins in a codon usage-defined manner (Li and others 2012). Thus, human SLFN11 appears to play a key role in the control of HIV infection in humans, and it is possible that its selective targeting may lead to the development of new antiviral drugs.

Slfn11 has also been found to bind to tRNAs and exploits the unique viral codon bias towards A/T nucleotides. The exact inhibition mechanism is unclear: Slfn11 may either sequester tRNAs, prevent their maturation via post-transcriptional processing or accelerate their deacylation. Slfn11 does not inhibit reverse transcription, integration or production and nuclear export of viral RNA.

Other recent studies have demonstrated that SLFN11 has an important role in sensitizing malignant cells to topoisomerase inhibitors [Barretina J. et al. Nature. 2012; 483 (7391):603-607], [Zoppoli G. et al., Proc Natl Acad Sci USA. 2012; 109(37):15030-15035] as well as alkylating agents and other DNA-damaging agents [Zoppoli G. et al., Proc Natl Acad Sci USA. 2012; 109(37):15030-15035].

A role for Slfn11 in cell cycle arrest and/or induction of apoptosis in response to exogenously induced DNA damage has also been suggested, particularly in response to DNA-damaging agents (DDA), leading to the suggestion it can be used as a biomarker for response to DDAs (Zoppoli et al., Proc Natl Acad Sci USA. 2012 Sep. 11; 109(37):15030-5).

SLFN11 has been found to be upregulated in a variety of cancers, including ovarian- and adenocarcinomas. It has also recently been shown that SLFN11 is hypermethylated in estrogen receptor-positive (ER+) breast cancers (but not in estrogen receptor-negative), resulting in transcriptional silencing of the gene (Fackler et al., Cancer Res. 2011 Oct. 1; 71(19):6195-207). This suggests that SLFN11 may plan a role in breast cancer development, and is an ER-specific marker that could be predictive for the outcome within ER subgroups.

An example Slfn11 (human) amino acid and mRNA sequence is set out below in the 'Sequences section'.

ERK

Erk is a known downstream target of Axl signaling, involved in regulating release of matrix metalloproteases from the cells in the process of invasion (Tai et al., Oncogene. 2008 Jul. 3; 27(29):4044-55). Gas6, the ligand for Axl, has also been shown to also activate Erk signaling and thereby stimulate DNA synthesis, proliferation and prolong survival of cardiac fibroblasts in serum-free conditions (Stenhoff et al., Biochem Biophys Res Commun. 2004 Jul. 2; 319(3):871-8). Thus, Erk is a downstream effector of Axl.

An example ERK (human ERK1, also known as MAPK3) amino acid and mRNA sequence is set out below in the 'Sequences section'.

PLCγ1

Phospholipase Gamma-1 (PLCγ1) is an intracellular signaling protein that catalyzes the formation of inositol 1,4,5-trisphosphate and diacylglycerol from phosphatidylinositol 4,5-bisphosphate. This reaction uses calcium as a cofactor and plays an important role in the intracellular transduction of receptor-mediated tyrosine kinase activators.

PLCγ1 has been shown to interact directly with Axl by binding at its C-terminal tyrosine 821 docking site (Braunger et al., Oncogene. 1997 Jun. 5; 14(22):2619-31). However, others report that they did not see a direct interaction of Axl and PLCγ (ref PMID 18346204), the difference being that the former study used the cytoplasmic moiety of Axl, whereas the latter study used full-length Gas-6 stimulated Axl protein. Not much is known about the functional relationship of Axl and PLCγ, but it has implied that it could be related to cytoskeletal regulation of cellular migration (Nielsen-Preiss et al., Endocrinology. 2007 June; 148(6): 2806-14).

An example PLCγ1 (human) amino acid and mRNA sequence is set out below in the 'Sequences section'.

Expression of PHGDH is Regulated by Axl Receptor Tyrosine Kinase Signalling

The present inventors have found that expression of PHGDH is regulated by Axl receptor tyrosine kinase signalling. More specifically, it has been found that levels of PHGDH expression are reduced (relative to untreated cells) in 'responder' acute myeloid leukemia (AML) cell lines upon exposure to the Axl inhibitor BGB324/R428; in contrast, levels of PHGDH expression are increased (relative to untreated cells) in 'non-responder' acute myeloid leukemia (AML) cell lines upon exposure to the Axl inhibitor BGB324/R428. Accordingly, expression of PHGDH can be used as an indicator of Axl receptor tyrosine kinase signalling in the applications described herein.

As used herein, a 'responder AML cell line' is a cell line with a low $IC_{50}$ for the small molecule Axl kinase inhibitor BGB324/R428; examples include the MOLM13 and Mv4-11 cell lines, with an $IC_{50}$ of 0.45 µM and 0.14 µM, respectively. Correspondingly, a 'non-responder AML cell line' is a cell line with a high $IC_{50}$ for the small molecule Axl kinase inhibitor BGB324/R428; examples are the Kasumi and OCI-M1 cell lines, with an $IC_{50}$ of 1.2 µM and 1.8 µM, respectively.

The demonstration of the link between Axl receptor tyrosine kinase signalling and PHGDH expression identifies PHGDH as part of the Axl signalling cascade. Thus, the current studies have identified PHGDH as a potential new target for intervention and treatment of conditions in which the Axl pathway plays a role. Accordingly, it is envisaged that Axl-related conditions can be treated by administering a PHGDH inhibitor to a subject, either alone or in combination with an Axl inhibitor or an EMT inhibitor.

Identifying PHGDH Inhibitors

According to one aspect of the invention, there is provided a method of selecting a pharmaceutical compound useful for the prevention, inhibition or treatment of an Axl-related condition the method comprising providing a group of candidate pharmaceutical compounds for testing, testing the effect of candidate pharmaceutical compounds in a test system, and selecting a candidate pharmaceutical compound on the basis of inhibiting PHGDH expression.

Alternatively the invention provides a method of selecting a candidate pharmaceutical compound useful in the treatment of metastatic or drug resistant cancer, the method comprising providing a group of candidate pharmaceutical compounds for testing, testing the effect of candidate pharmaceutical compounds in a test system, and selecting a candidate pharmaceutical compound on the basis of its inhibition of PHGDH expression.

According to another aspect there is provided a method of selecting a candidate pharmaceutical compound useful in the prevention or inhibition of EMT, the method comprising providing a group of candidate pharmaceutical compounds for testing, testing the effect of candidate pharmaceutical compounds in a test system, and selecting a candidate pharmaceutical compound on the basis of inhibiting PHGDH expression.

It is highly advantageous to be able to determine effective levels of a candidate pharmaceutical compound in an in vitro test system in order to predict in vivo responses. This facilitates determination of effective minimum dosage levels of a pharmaceutical compound and also the validation of drug targets in a dose-dependent manner. Accordingly, it is envisaged that the test systems described herein may be in vitro test systems. A particularly useful approach to predicting in vivo responses to a pharmaceutical is through conditional selective knockout of a target gene through RNA interference. The effective generation of nucleotides for use in such methods is described in WO2009/082488.

According to another aspect of the invention there is provided a method of selecting a candidate pharmaceutical compound useful in the prevention, inhibition or treatment of an Axl-related condition, the method comprising selectively reducing expression of Axl in a test cell, contacting the test cell with the candidate pharmaceutical compound and determining the effect of the candidate pharmaceutical compound on inhibition of PHGDH expression.

According to a further aspect of the invention there is provided a method of selecting a compound useful in the prevention, inhibition or treatment of an Axl-related condition, the method comprising selectively reducing expression of Axl in an in vitro test system to a low level contacting the test system with a candidate pharmaceutical compound, and selecting candidate pharmaceutical compounds which inhibit PHGDH expression.

Identifying Subjects with Axl-Related Conditions

According to a further aspect of the invention there is provided a method of identifying a subject having an Axl-related condition, the method comprising assessing the level of expression or activity of PHGDH in the subject, or in a sample derived from the subject. Generally, the level of expression or activity in a subject or in a sample derived from a subject may be determined relative to a control sample, as described herein.

According to a further aspect of the invention there is provided a method of identifying a subject having a particular risk of developing metastatic or drug-resistant cancer, the method comprising assessing the level of expression or activity of PHGDH in the subject, or in a sample derived from the subject, an increased level of PHGDH expression or activity indicating an increased risk of the subject of developing metastatic or drug-resistant cancer.

According to a further aspect of the invention there is provided a method of identifying the presence of a Cancer Stem Cell in a subject, the method comprising determining the level of PHGDH expression or activity in the subject, or in a sample derived from the subject, increased expression or activity of PHGDH indicating the existence of a Cancer Stem Cell (CSC).

According to a further aspect of the invention there is provided a method of identifying a subject undergoing EMT, the method comprising determining the level of PHGDH expression or activity in the subject, or in a sample derived from the subject, an increase in expression or activity of PHGDH indicating the occurrence of EMT.

Identifying Axl Activity

According to a further aspect of the invention there is provided a method of identifying Axl activity, the method comprising determining the level of PHGDH expression or activity in the subject, or in a sample derived from the subject, increased activity or expression of PHGDH correlating with Axl activity.

In some embodiments, the level of expression of PHGDH is assessed by determining the copy number of the gene encoding PHGDH relative to a control sample, wherein an increase in the copy number indicates an increased level of expression of PHGDH. Copy number (i.e. gene duplication events) may be determined using standard techniques known in the art, e.g. using a DNA chip as described in Jiang et al. (Jiang Q, Ho Y Y, Hao L, Nichols Berrios C, Chakravarti A. Copy number variants in candidate genes are genetic modifiers of Hirschsprung disease. PLoS One. 2011; 6(6)).

In some embodiments, the level of expression of PHGDH is assessed by determining the level of PHGDH protein or mRNA. Methods for determining protein and mRNA expression levels are well known in the art, and described herein.

Methods of Treating a Subject

According to another aspect of the invention there is provided a method of treating a subject having an Axl-related condition, the method comprising contacting the subject with a PHGDH inhibitor, or with a pharmaceutical compound selected as, or derived from, a candidate compound obtained by a method according to the first aspect of the invention.

In some embodiments, PHGDH inhibitors are administered in combination with another cancer therapeutic agent, for example an agent capable of inhibiting or reversing EMT, or another chemotherapeutic agent as defined herein. Agents capable of inhibiting or reversing EMT are described herein e.g. an Akt3 inhibitor or an Axl inhibitor (such as BGB324/R428).

Thus, in some embodiments there is provided a method of treating a subject having an Axl-related condition, the method comprising contacting the subject with:
(i) a PHGDH inhibitor, or with a pharmaceutical compound selected as, or derived from, a candidate compound obtained by a method according to the first aspect of the invention; and
(ii) another cancer therapeutic agent, for example an agent capable of inhibiting or reversing EMT, or another chemotherapeutic agent as defined herein.

Further aspects of the invention include a method of inhibiting EMT in a subject, the method comprising contacting the subject with a compound capable of inhibiting PHGDH expression or activity.

A further aspect of the invention provides a method of inhibiting Cancer Stem Cells in a subject, the method comprising of contacting the subject with a compound capable of inhibiting PHGDH expression or activity.

The invention also provides a method of preventing or inhibiting drug resistance in a subject having cancer, the method comprising contacting the subject with a compound capable of inhibiting PHGDH expression or activity.

The invention also provides the use of a PHGDH inhibitor in the treatment of an Axl related condition, such as cancer.

The invention also provides the use of a PHGDH inhibitor in the inhibition of EMT.

The invention also provides a PHGDH inhibitor for use in a method of treatment as described herein. For example, the treatment of an Axl-related disease.

The invention also provides for the use of a PHGDH inhibitor in the manufacture of a medicament for use in a method of treatment as described herein. For example, the treatment of an Axl-related disease.

According to a further aspect of the invention there is provided the use of a compound capable of inhibiting PHGDH activity or expression in the prevention, inhibition, or treatment of drug resistance in a subject having cancer, the method comprising contacting the subject with a compound capable of inhibiting PHGDH activity or expression.

PHGDH inhibitors identified by methods in accordance with the invention, or used in methods or uses in accordance with the invention, may be used as a monotherapy or in combination therapy with other suitable cancer treatments as mentioned below. In particular, the use of PHGDH inhibitors in combination with one or more agents capable of inhibiting or reversing EMT (e.g. an Akt3 inhibitor or an Axl inhibitor, such as BGB324/R428) are envisaged.

Other suitable chemotherapeutic agents include:
alkylating agents, including alkyl sulfonates such as busulfan;
nitrogen mustards such as chlorambucil, cyclophosphamide, estramustine, ifosfamide, mechlorethamine, melphalan, and uramustine, ethyleneimine derivatives such as thiotepa;
nitrosoureas such as carmustine, lomustine, and streptozocin, triazenes such as dacarbazine, procarbazine, and temozolamide, and
platinum compounds such as cisplatin, carboplatin, oxaliplatin, satraplatin, and picoplatin onnaplatin, tetraplatin, sprioplatin, iproplatin, chloro(diethylenediamino)- platinum (II) chloride, dichloro(ethylenediamino)-platinum (II), diamino(2-ethylmalonato)platinum (II), (1,2-diaminocyclohexane)malonatoplatinum (II), (4-carboxyphthalo)-(1,2-diaminocyclohexane)platinum (II), (1,2-diaminocyclohexane)-(isocitrato)platinum (II), and (1,2-diaminocyclohexane)-cis-(pyruvato) platinum (II);

antimetabolites, including antifolates such as methotrexate, permetrexed, raltitrexed, and trimetrexate, pyrimidine analogs such as azacitidine, capecitabine, cytarabine, edatrexate, floxuridine, fluorouracil, gemcitabine, and troxacitabine, and purine analogs such as cladribine, chlorodeoxyadenosine, clofarabine, fludarabine, mercaptopurine, pentostatin, and thioguanine;

natural products, including antitumor antibiotics such as bleomycin, dactinomycin, mithramycin, mitomycin, mitoxantrone, porfiromycin, and anthracyclines such as daunorubicin, doxorubicin, epirubicin, idarubicin, and valrubicin, mitotic inhibitors such as the vinca alkaloids vinblastine, vinvesir, vincristine, vindesine, and vinorelbine, enzymes such as L-asparaginase and PEG-L-asparaginase, microtubule polymer stabilizers such as the taxanes paclitaxel and docetaxel, topisomerase I inhibitors such as the camptothecins irinotecan and topotecan, and topoisomerase II inhibitors such as podophyllotoxin, amsacrine, etoposide, teniposide, losoxantrone and actinomycin;

hormones and hormone antagonists, including androgens such as fluoxymesterone and testolactone, antiandrogens such as bicalutamide, cyproterone, flutamide, and nilutamide, corticosteroids such as dexamethasone and prednisone, aromatase inhibitors such as aminoglutethimide, anastrozole, exemestane, formestane, and letrozole, estrogens such as diethylstilbestrol, antiestrogens such as fulvestrant, raloxifene, tamoxifen, and toremifine, luteinising hormone-releasing hormone (LHRH) agonists and antagonists such as abarelix, buserelin, goserelin, leuprolide, histrelin, desorelin, nafarelin acetate and triptorelin, progestins such as medroxyprogesterone acetate and megestrol acetate, and thyroid hormones such as levothyroxine and liothyronine;

PKB pathway inhibitors, including perifosine, enzastaurin hydrochloride, and triciribine, PI3K inhibitors such as semaphore and SF1126, and MTOR inhibitors such as rapamycin and analogues;

CDK inhibitors, including seliciclib, alvocidib, and 7-hydroxystaurosporine;

COX-2 inhibitors, including celecoxib;

HDAC inhibitiors, including trichostatin A, suberoylanilide hydroxamic acid, and chlamydocin;

DNA methylase inhibitors, including temozolomide; and miscellaneous agents, including altretamine, arsenic trioxide, thalidomide, lenalidomide, gallium nitrate, levamisole, mitotane, hydroxyurea, octreotide, procarbazine, suramin, photodynamic compounds such as methoxsalen and sodium porfimer, and proteasome inhibitors such as bortezomib.

Molecular targeted therapy agents including:

functional therapeutic agents, including gene therapy agents, antisense therapy agents, tyrosine kinase inhibitors such as erlotinib hydrochloride, gefitinib, imatinib mesylate, and semaxanib, Raf inhibitors such as sorafenib, and gene expression modulators such as the retinoids and rexinoids, for example adapalene, bexarotene, trans-retinoic acid, 9-cis-retinoic acid, and N-(4-hydroxyphenyl)retinamide; and phenotype-directed therapy agents, including monoclonal antibodies such as alemtuzumab, bevacizumab, cetuximab, ibritumomab tiuxetan, rituximab, and trastuzumab, immunotoxins such as gemtuzumab ozogamicin, radioimmunoconjugates such as I-tositumobab, and cancer vaccines.

Biologic therapy agents including:

interferons such as interferon-[alpha]2a and interferon-[alpha]2b, and interleukins such as aldesleukin, denileukin diftitox, and oprelvekin. Axl inhibiting agents including 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine (BGB324/R428), CH5451098 (Roche) and Axl inhibitors described in PCT/US07/089177, PCT/US2010/021275 and PCT/EP2011/004451, incorporated herein by reference.

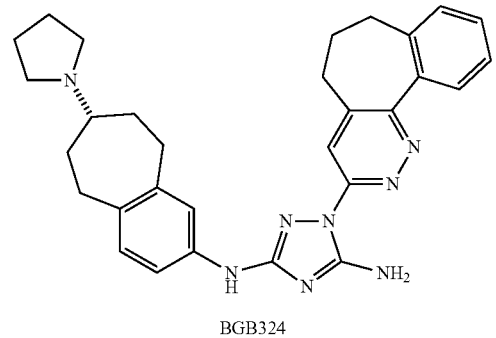

BGB324

In addition to these agents intended to act against cancer cells, anticancer therapies include the use of protective or adjunctive agents, including:

cytoprotective agents such as amifostine, and dexrazoxane, phosphonates such as pamidronate and zoledronic acid, and stimulating factors such as epoetin, darbeopetin, filgrastim, PEG-filgrastim, and sargramostim.

Many combination chemotherapeutic regimens are known to the art, such as combinations of carboplatin/paclitaxel, capecitabine/docetaxel, fluorauracil/levamisole, fluorauracil/leucovorin, methotrexate/leucovorin, and trastuzumab/paclitaxel, alone or in further combination with carboplatin, and the like.

According to a further aspect of the invention is provided a method of selecting patients, preferably human patients, for treatment of an Axl-related condition, the method comprising identifying patients having elevated PHGDH activity or expression and selecting thus identified patients for treatment. The treatment may comprise, for example, administering an EMT inhibitor such as an Axl inhibitor.

In another aspect of the invention is provided a method of selecting patients, preferably human patients, for treatment of an Axl-related condition, the method comprising identifying patients having decreased PHGDH activity or expression (relative to a non-exposed control sample) after contact with a cancer therapeutic agent, and selecting thus identified patients for treatment. The treatment may comprise, for example, administering an EMT inhibitor such as an Axl inhibitor.

Patients may be identified according to the methods of the invention as described herein.

Patients identified or selected according to the methods of the invention may be treated, or selected for treatment. For example, if PHGDH expression is shown to be upregulated in a primary tumor, this can be used to infer an increased probability of metastasis. This information can be used as a guide to treatment options, i.e. more aggressive anti-cancer surgical, chemotherapeutic or radiotherapeutic treatment such as radical mastectomy. In some embodiments, treatment comprises administration of an Akt3 and/or Axl inhibitor, optionally in combination with a further therapeutic agent described herein (such as administration of a PHGDH inhibitor) or known in the art. Preferably the Axl inhibitor is BGB324/R428.

Identifying Axl Inhibitors

The invention also provides a method of identifying a compound which inhibits Axl activity, a method comprising contacting a cell from a cell line according to the invention with a test compound and determining inhibition of PHGDH expression or activity in the cell.

Detection of EMT

One aspect of the invention relates to the use of PHGDH as a biomarker for detecting the occurrence of epithelial-to-mesenchymal transition (EMT) in a subject. In some embodiments, an increase in the expression and/or activation of PHGDH is indicative of the occurrence of epithelial-to-mesenchymal transition (EMT).

Metastasis to distant sites is the most common cause of death from solid tumors (Gupta 2006, Sporn 1996). To accomplish this, tumor cells discard epithelial restraints, redefine junctional complexes and acquire invasive motility to break across the basement membrane border. These metastatic cells then intravasate into the lymphatic and hematogenous circulation, disseminating to distant sites in the body. A few of these metastatic cells succeed in extravasating through the capillary wall and in rare cases colonize the foreign tissue stroma (Weinberg et al). This malignant process is facilitated by an epithelial-to-mesenchymal transition (EMT), a developmental program where epithelial cells transiently assume a mesenchymal phenotype during gastrulation and organogenesis, allowing single cell invasive movement away from the epithelial layer (Hall, 1985; Thierry, 2002). The EMT program is initiated by contextual activation of morphogen signaling pathways that induce the expression of transcriptional regulators, including Twist, Snail, Slug and Zeb2, which alter the expression of junctional complex proteins (Thiery and SLeeman 2006). The EMT gene expression profile reflects the phenotypic shift, repression of E-cadherin and cytokeratins with induction of vimentin and N-cadherin (Weinberg et al 2007).

The term "marker" or "biomarker" is used herein to refer to a gene or protein whose expression in a sample derived from a cell or mammal is altered or modulated, for example, up or down regulated, when epithelial-to-mesenchymal transition (EMT) takes place. Where the biomarker is a protein, modulation or alteration of expression encompasses modulation through different post-translational modifications.

Post-translational modifications are covalent processing events that change the properties of a protein by proteolytic cleavage or by addition of a modifying group to one or more amino acids. Common post-translational modifications include phosphorylation, acetylation, methylation, acylation, glycosylation, GPI anchor, ubiquitination and so forth. A review of such modifications and methods for detection may be found in Mann et al. Nature Biotechnology March 2003, Vol. 21, pages 255-261.

Detection of Axl Expression

Also provided herein is the use of PHGDH as a biomarker for detecting the expression and/or activation of Axl, wherein an increase in the expression and/or activation of PHGDH is indicative of an increase in the expression and/or activation of Axl.

The term "expression" refers to the transcription of a gene's DNA template to produce the corresponding mRNA and translation of this mRNA to produce the corresponding gene product (i.e., a peptide, polypeptide, or protein) as well as the "expression" of a protein in one or more forms that may have been modified post translation.

Detection of the level of expression including gene expression may be performed by any one of the methods known in the art, particularly by microarray analysis, Western blotting or by PCR techniques such as QPCR. Altered expression may also be detected by analysing protein content of samples using methods such as ELISA, PET or SELDI-TOF MS as described herein and using further analytical techniques such as 2D gel electrophoresis. Techniques such as this can be particularly useful for detecting altered expression in the form of alternative post translationally modified forms of a protein.

Suitable samples include, but are not limited to, tissue samples such as biopsy, blood, urine, buccal scrapes etc, serum, plasma or tissue culture supernatant samples. Preferably the sample is a blood sample. In one embodiment, gene expression is preferably detected in tumour cells, particularly cells derived from a tumour such as breast, lung, gastric, head and neck, colorectal, renal, pancreatic, uterine, hepatic, bladder, endometrial and prostate cancers and leukemias or from blood cells such as lymphocytes and, preferably, PBMCs such as lymphocytes.

In detection of proteins in serum and, in particular, in plasma samples of patients, samples are removed and subjected to protein analytical techniques such as flow cytometry, mass cytometry (CyTOF), ELISA, PET and SELDI-TOF MS.

In one preferred embodiment, the method comprises extracting RNA from said sample and detecting gene expression by QPCR.

In one embodiment, gene expression is detected by detecting protein products such as, for example, by Western Blot.

A further aspect of the invention provides a method for detecting the occurrence of epithelial-to-mesenchymal transition (EMT) in a sample, said method comprising determining the expression level or activation of PHGDH in a sample isolated from a cell, group of cells, an animal model or human as compared to a control sample, wherein an increase in the expression level or activation of PHGDH relative to the control sample is indicative of the occurrence of epithelial-to-mesenchymal transition (EMT).

Identifying EMT Inhibitors

A further aspect of the invention relates to a method for identifying an agent capable of inhibiting or reversing epithelial-to-mesenchymal transition (EMT), said method comprising administering said agent to a cell, group of cells or animal model, and monitoring the activation and/or the expression of PHGDH.

In one embodiment, the method comprises:
(i) administering the agent to a cell, group of cells or an animal model, not a human; and
(ii) measuring PHGDH expression and/or PHGDH activation in samples derived from the treated and the untreated cells or animal model; and
(iii) detecting a decrease in the expression and/or activation of PHGDH in the treated sample as compared to the untreated sample as an indication of the ability to inhibit or reverse epithelial-to-mesenchymal transition (EMT).

In some embodiments, the animal model is not a human.

In some embodiments, the level of expression of PHGDH is assessed by determining the copy number of the gene encoding PHGDH relative to a control sample, wherein an increase in the copy number indicates an increased level of expression of PHGDH.

In some embodiments, the level of expression of PHGDH is assessed by determining the level of PHGDH protein or mRNA.

Biomarkers in Diagnostics and Prognostics

Heterogeneous Patient Populations

Whilst cancers are categorised into classes which share broad characteristics, some of these classes are particularly heterogeneous. In such a heterogeneous population, it is advantageous to have a spectrum of biomarkers that are reasonably consistent within different cancer cell lines in order to have markers that will give a reliable readout in a high proportion of patients.

For example, AML is known to be a heterogeneous cancer with existing cell lines such as MOLM13 and Mv4-11 that have a low $IC_{50}$ to Axl inhibitors such as BGB324 (i.e. cells that respond well to treatment with Axl-inhibitors, so-called responder cell lines), and cells such as Kasumi, OCI-M1 and OCI-AML5 that have a high $IC_{50}$ to Axl inhibitors such as BGB324 (i.e. cells that respond poorly to treatment with Axl-inhibitors, so-called non-responder cell lines). By identifying biomarkers that reliably distinguish these cell types it is possible to use the biomarkers to predict the clinical outcome for the patients.

Described herein are the results of the investigation of six biomarkers in AML cell-lines treated with BGB324 in vitro and in xenograft material from in vivo AML models. The markers were Axl (total and phospho), Akt (phospho), Erk (total and phospho), PLCγ1 (total and phospho), PHGDH and SLFN11. PLCγ1-, SLFN11- and PHGDH- were found to be of particular prognostative value, with the expression of these markers going down following contact with BGB324 in 'responder' AML cell-lines and up following contact with BGB324 in 'non-responder' AML cell-lines.

Total Axl expression gives a similar pattern to PLCγ1-, SLFN11- and PHGDH although the changes are less marked, possibly due to a relatively low Axl expression in the cell lines.

Total Erk expression gives a distinct pattern of behaviour, with a reduction in most cell lines (all except MOLM13), with no clear distinction between responders and non-responding cells.

The in vivo data is also instructive, in that it does not exactly mirror the in vitro data. Generally, a similar pattern in all markers was observed in both of the studied tissue types (spleen and bone marrow): pErk, pPLCγ1 and PHGDH are significantly reduced in both, and pAkt is also reduced in both, though not significantly. SLFN11 is only significantly reduced in bone marrows. Thus, whilst a marker such as pAkt appears promising in vitro, it is less so in vivo. Similarly, a marker such as PHGDH does not appear to be the best candidate in vitro, but gives a robust response in in vivo models.

Accordingly, the invention also relates to the use of one or more of the biomarkers described herein (Axl, Akt, Erk, PLCγ, PHGDH, and SLFN11) in the diagnosis or prognosis of Axl-related diseases (such as AML) and diseases characterized by proliferative activity, particularly in individuals being treated with Axl or Akt3 inhibitors.

Throughout this 'Biomarkers in Diagnostics and Prognostics section' specification, "one or more of the biomarkers described herein" (Axl, Akt, Erk, PLCγ, PHGDH, and SLFN11) are referred to. In some embodiments the biomarker is SLFN11. In some embodiments the biomarker is PLCγ1. In some embodiments the biomarker is ERK. In some embodiments the biomarker is Axl. In some embodiments the biomarker is Akt. In preferred embodiments the biomarker is PHGDH. In some embodiments two, three, four, five, or all six of the biomarkers are used. In some embodiments the biomarkers are PHGDH, PLCγ1, and SLFN11. In some embodiments the biomarkers are Axl and Akt. In some embodiments the biomarkers are Axl, Akt, Erk, PLCγ1, PHGDH, and SLFN11.

As used herein, the term "prognostic method" means a method that enables a prediction regarding the progression of a disease of a human or animal diagnosed with the disease, in particular, cancer. More specifically, the cancers of interest include acute myelocytic leukemias (AMLs), breast, lung, gastric, head and neck, colorectal, renal, pancreatic, uterine, hepatic, bladder, endometrial and prostate cancers and other leukemias. AMLs are of particular interest.

The term "diagnostic method" as used herein means a method that enables a determination of the presence or type of cancer in or on a human or animal. Suitably the biomarker allows the success of treatment with an EMT, Axl, Akt3, or PHGDH inhibitor (or combination thereof) to be assessed. As discussed above, suitable diagnostics include probes directed to any of the genes as identified herein such as, for example, QPCR primers, FISH probes and so forth.

The term "prognostic method" as used herein means a method that enables a determination of the likelihood of a subject being susceptible or responsive to treatment with a particular agent/regimen. Such prognostic methods provide information on the likely outcome of a particular treatment regimen, for example, the likelihood of a subject responding to said treatment, and/or information as to how aggressively an individual should be treated within a particular treatment regimen, and/or how aggressively an individual should be treated with conventional therapeutic methods such as radiation/chemotherapy. The prognostic methods described herein therefore have important applications in the field of personalised medicines.

According to a further aspect of the invention there is provided a method of prognosing a cancer-related outcome in a subject, the method comprising assessing the activity or expression of one or more of the biomarkers described herein in the subject, or in a sample derived from the subject (for example, a blood sample).

In some embodiments, an increase in the activity or expression of one or more of the biomarkers described herein relative to a control sample is indicative of increased susceptibility to treatment with a cancer therapeutic agent, for example an agent capable of inhibiting or reversing EMT, or another chemotherapeutic agent as defined herein.

In some embodiments, an increase in the activity or expression of one or more of the biomarkers described herein after contacting the subject, or a sample derived from the subject (for example, a blood sample), with a cancer therapeutic agent (for example an agent capable of inhibiting or reversing EMT) relative to a non-exposed control sample is indicative of decreased susceptibility to treatment with the cancer therapeutic agent.

In some embodiments, a decrease in the activity or expression of one or more of the biomarkers described herein after contacting the subject, or a sample derived from the subject (for example, a blood sample), with a cancer therapeutic agent (for example an agent capable of inhibiting or reversing EMT) relative to a non-exposed control sample is indicative of increased susceptibility to treatment with the cancer therapeutic agent.

Accordingly, one preferred aspect thus relates to the use of one or more of the biomarkers described herein (Axl Akt, Erk, PLCγ1, PHGDH, and/or SLFN11) as biomarkers in a personalised medicine application.

In one preferred embodiment, the personalised medicine application is for determining whether a subject will be susceptible or responsive to treatment with an EMT, Akt3 or Axl inhibitor. For example, in some embodiments a decrease in the activity or expression of one or more of the biomarkers described herein after contacting the subject, or a sample derived from the subject (for example, a blood sample), with a cancer therapeutic agent (for example an agent capable of inhibiting or reversing EMT) relative to a non-exposed control sample is indicative of increased susceptibility to treatment with the cancer therapeutic agent.

In one preferred embodiment, the personalised medicine application is for determining whether a subject is particularly likely to suffer from metastatic cancer.

Another aspect of the invention relates to a prognostic method for determining whether a subject will be susceptible to treatment with an Akt3, Axl, or PHGDH inhibitor, said method comprising detecting the occurrence of epithelial-to-mesenchymal transition (EMT) in said subject.

Another aspect of the invention relates to the use of one or more of the biomarkers described herein in a prognostic agent for determining whether a subject will be susceptible or responsive to treatment with an EMT, Akt3, Axl, or PHGDH inhibitor, such as BGB324. For example, in some embodiments a decrease in the activity or expression of one or more of the biomarkers described herein after contacting the subject, or a sample derived from the subject (for example, a blood sample), with a cancer therapeutic agent (for example an agent capable of inhibiting or reversing EMT) relative to a non-exposed control sample is indicative of increased susceptibility to treatment with the cancer therapeutic agent.

Another aspect of the invention relates to a prognostic method for determining whether a subject is particularly likely to suffer from metastatic cancer, said method comprising detecting the occurrence of epithelial-to-mesenchymal transition (EMT) in said subject.

In some embodiments, the occurrence of epithelial-to-mesenchymal transition (EMT) in said subject is determined by assessing the level of the activity or expression of one or more of the biomarkers described herein, wherein the activity or expression of one or more of the biomarkers described herein, or increased activity or expression of one or more of the biomarkers described herein, is indicative of the occurrence of epithelial-to-mesenchymal transition (EMT).

Throughout the specification, preferably the methods described herein are performed in vitro or ex vivo.

Throughout the specification, references are made to PHGDH inhibitors. As used herein, the term PHGDH inhibitor refers to an agent that inhibits or reduces PHGDH activity or expression.

Measuring Altered Expression of Gene/Protein Markers

Levels of gene and protein expression may be determined using a number of different techniques.

(a) at the RNA Level

Gene expression can be detected at the RNA level. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilising ribonucleic acid hybridisation include nuclear run-on assays, RT-PCR, RNase protection assays (Melton et al, *Nuc. Acids Res.* 12:7035), Northern blotting and In Situ hybridization. Gene expression can also be detected by microarray analysis as described below.

For Northern blotting, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

Nuclease Protection Assays (including both ribonuclease protection assays and S1 nuclease assays) provide an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. NPAs allow the simultaneous detection of several RNA species.

In situ hybridization (ISH) is a powerful and versatile tool for the localization of specific mRNAs in cells or tissues. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. Alternatively, tissue can be sectioned frozen and post-fixed in paraformaldehyde. After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents. This latter method of detection is the basis for Fluorescent In Situ Hybridisation (FISH).

Methods for detection which can be employed include radioactive labels, enzyme labels, chemiluminescent labels, fluorescent labels and other suitable labels.

Typically, RT-PCR is used to amplify RNA targets. In this process, the reverse transcriptase enzyme is used to convert RNA to complementary DNA (cDNA) which can then be amplified to facilitate detection. Relative quantitative RT-PCR involves amplifying an internal control simultaneously with the gene of interest. The internal control is used to normalize the samples. Once normalized, direct comparisons of relative abundance of a specific mRNA can be made across the samples. Commonly used internal controls include, for example, GAPDH, HPRT, actin and cyclophilin.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification (TAS) methods have been described in the literature, for example, general reviews of these methods in Landegren, U. et al., *Science* 242:229-237 (1988) and Lewis, R., *Genetic Engineering News* 10:1, 54-55 (1990).

PCR is a nucleic acid amplification method described inter alia in U.S. Pat. Nos. 4,683,195 and 4,683,202. PCR can be used to amplify any known nucleic acid in a diagnostic context (Mok et al., 1994, *Gynaecologic Oncology* 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, *Proc. Natl. Acad. Sci. USA* 87:1874). Ligation amplification reaction or ligation amplification system uses DNA ligase and four oligonucleotides, two per target strand. This technique is described by Wu, D. Y. and Wallace, R. B., 1989, *Genomics* 4:560. In the Qβ Replicase technique, RNA replicase for the bacteriophage Qβ, which replicates single-stranded RNA, is used to amplify the target DNA, as described by Lizardi et al., 1988, *Bio/Technology* 6:1197.

Quantitative PCR (Q-PCR) is a technique which allows relative amounts of transcripts within a sample to be determined. A suitable method for performing QPCR is described herein.

Alternative amplification technology can be exploited in the present invention. For example, rolling circle amplification (Lizardi et al., 1998, *Nat Genet* 19:225) is an amplification technology available commercially (RCAT™) which is driven by DNA polymerase and can replicate circular oligonucleotide probes with either linear or geometric kinetics under isothermal conditions. A further technique, strand displacement amplification (SDA; Walker et al., 1992, *Proc. Natl. Acad. Sci. USA* 80:392) begins with a specifically defined sequence unique to a specific target.

Suitable probes for detecting the expression of PHGDH identified herein may conveniently be packaged in the form of a test kit in a suitable container. In such kits the probe may be bound to a solid support where the assay format for which the kit is designed requires such binding. The kit may also contain suitable reagents for treating the sample to be probed, hybridising the probe to nucleic acid in the sample, control reagents, instructions, and the like. Suitable kits may comprise, for example, primers for a QPCR reaction or labelled probes for performing FISH.

(b) at the Polypeptide Level

Altered gene or protein expression may also be detected by measuring the polypeptides encoded by the PHGDH gene. This may be achieved by using molecules which bind to the polypeptides encoded by the PHGDH gene. Suitable molecules/agents which bind either directly or indirectly to the polypeptides in order to detect the presence of the protein include naturally occurring molecules such as peptides and proteins, for example antibodies, or they may be synthetic molecules.

Antibodies for the PHGDH gene or protein may be derived from commercial sources or through techniques which are familiar to those skilled in the art. In one embodiment, and where altered expression manifests itself through the expression of alteration of post translationally-modified forms of a protein biomarker, antibodies specific for those different forms may be used.

Methods for production of antibodies are known by those skilled in the art. If polyclonal antibodies are desired, a selected mammal (e.g., mouse, rabbit, goat, horse, etc.) is immunised with an immunogenic polypeptide bearing an epitope(s) from a polypeptide. Serum from the immunised animal is collected and treated according to known procedures. If serum containing polyclonal antibodies to an epitope from a polypeptide contains antibodies to other antigens, the polyclonal antibodies can be purified by immunoaffinity chromatography. Techniques for producing and processing polyclonal antisera are known in the art. In order to generate a larger immunogenic response, polypeptides or fragments thereof may be haptenised to another polypeptide for use as immunogens in animals or humans.

Monoclonal antibodies directed against epitopes in polypeptides can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against epitopes in the polypeptides of the invention can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes whole antibodies, or fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP239400A. For example: monoclonal and polyclonal antibodies, recombinant antibodies, proteolytic and recombinant fragments of antibodies (Fab, Fv, scFv, diabodies), single-domain antibodies (VHH, sdAb, nanobodies, IgNAR, VNAR), and proteins unrelated to antibodies, which have been engineered to have antibody-like specific binding, such as the following:

| Name | Based on: | |
|---|---|---|
| Affibodies | Protein A, Z domain | 6 kDa |
| Affitins | Sac7d (from *Sulfolobus acidocaldarius*) | 7 kDa |
| Anticalins | Lipocalins | 20 kDa |
| DARPins | Ankyrin repeat motif | 14 kDa |
| Fynomers | Fyn, SH3 domain | 7 kDa |
| Kunitz domain peptides | Various protease inhibitors | 6 kDa |
| Monobodies | Fibronectin | |

Standard laboratory techniques such as immunoblotting as described above can be used to detect altered levels of PHGDH activity, as compared with untreated cells in the same cell population.

Gene expression may also be determined by detecting changes in post-translational processing of polypeptides or post-transcriptional modification of nucleic acids. For example, differential phosphorylation of polypeptides, the cleavage of polypeptides or alternative splicing of RNA, and the like may be measured. Levels of expression of gene products such as polypeptides, as well as their post-translational modification, may be detected using proprietary protein assays or techniques such as 2D polyacrylamide gel electrophoresis.

Antibodies may be used for detecting PHGDH expression by a method which comprises: (a) providing an antibody; (b) incubating a biological sample with said antibody under conditions which allow for the formation of an antibody-antigen complex; and (c) determining whether antibody-antigen complex comprising said antibody is formed.

Suitable samples include extracts of tissues such as brain, breast, ovary, lung, colon, pancreas, testes, liver, muscle and bone tissues or from neoplastic growths derived from such tissues. Other suitable examples include blood or urine samples.

Antibodies that specifically bind to PHGDH proteins can be used in diagnostic or prognostic methods and kits that are well known to those of ordinary skill in the art to detect or quantify the expression of PHGDH protein in a body fluid or tissue. Results from these tests can be used to diagnose or predict the occurrence or recurrence of cancer and other cell motility or cell survival-mediated diseases, or to assess the effectiveness of drug dosage and treatment.

Antibodies can be assayed for immunospecific binding by any method known in the art. The immunoassays which can be used include but are not limited to competitive and non-competitive assay systems using techniques such as western blots, immunohistochemistry, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

Such assays are routine in the art (see, for example, Ausubel et aL, eds, 1994, *Current Protocols in Molecular Biology*, Vol. 1, John Wiley & Sons, Inc., New York, which is incorporated by reference herein in its entirety).

Antibodies for use in the invention are preferably bound to a solid support and/or packaged into kits in a suitable container along with suitable reagents, controls, instructions and the like.

Other methods include, but are not limited to, 2D-PAGE although this is less suitable for large-scale screening. Newer techniques include matrix-assisted laser desorption ionization time of flight mass spectrometry (MALDI-TOF MS). In MALDI-TOF analysis, proteins in a complex mixture are affixed to a solid metallic matrix, desorbed with a pulsed laser beam to generate gas-phase ions that traverse a field-free flight tube, and are then separated according to their mass-dependent velocities. Individual proteins and peptides can be identified through the use of informatics tools to search protein and peptide sequence databases. Surface-enhanced laser desorption/ionisation time of flight MS (SELDI-TOF MS) is an affinity-based MS method in which proteins are selectively adsorbed to a chemically modified solid surface, impurities are removed by washing, an energy-absorbing matrix is applied, and the proteins are identified by laser desorption mass analysis.

SELDI-TOF-MS can be used for the detection of the appearance/loss of either intact proteins or fragments of specific proteins. In addition SELDI-TOF-MS can also be used for detection of post translational modifications of proteins due to the difference in mass caused by the addition/removal of chemical groups. Thus phosphorylation of a single residue will cause a mass shift of 80 Da due to the phosphate group. A data base of molecular weights that can be attributed to post-translational modifications is freely accessible on the internet (http://www.abrf.org/index.cfm/dm.home?avgmass=all). Moreover specific polypeptides can be captured by affinity-based approaches using SELDI-TOF-MS by employing antibodies that specifically recognise a post-translationally modified form of the protein, or that can recognise all forms of the protein equally well.

Arrays

Array technology and the various techniques and applications associated with it is described generally in numerous textbooks and documents. These include Lemieux et al., 1998, *Molecular Breeding* 4:277-289; Schena and Davis. *Parallel Analysis with Biological Chips.* in *PCR Methods Manual* (eds. M. Innis, D. Gelfand, J. Sninsky); Schena and Davis, 1999, *Genes, Genomes and Chips*. In *DNA Microarrays: A Practical Approach* (ed. M. Schena), Oxford University Press, Oxford, UK, 1999); *The Chipping Forecast* (*Nature Genetics* special issue; January 1999 Supplement); Mark Schena (Ed.), *Microarray Biochip Technology*, (Eaton Publishing Company); Cortes, 2000, *The Scientist* 14(17): 25; Gwynne and Page, *Microarray analysis: the next revolution in molecular biology, Science,* 1999, Aug. 6; Eakins and Chu, 1999, *Trends in Biotechnology,* 17:217-218, and also at various world wide web sites.

Array technology overcomes the disadvantages with traditional methods in molecular biology, which generally work on a "one gene in one experiment" basis, resulting in low throughput and the inability to appreciate the "whole picture" of gene function. Currently, the major applications for array technology include the identification of sequence (gene/gene mutation) and the determination of expression level (abundance) of genes. Gene expression profiling may make use of array technology, optionally in combination with proteomics techniques (Celis et al., 2000, *FEBS Lett,* 480(1):2-16; Lockhart and Winzeler, 2000, *Nature* 405 (6788):827-836; Khan et al., 1999, 20(2):223-9). Other applications of array technology are also known in the art; for example, gene discovery, cancer research (Marx, 2000, *Science* 289: 1670-1672; Scherf et al., 2000, *Nat Genet* 24(3):236-44; Ross et al., 2000, *Nat Genet* 2000, 24(3):227-35), SNP analysis (Wang et al., 1998, *Science* 280(5366): 1077-82), drug discovery, pharmacogenomics, disease diagnosis (for example, utilising microfluidics devices: *Chemical & Engineering News,* Feb. 22, 1999, 77(8):27-36), toxicology (Rockett and Dix (2000), *Xenobiotica* 30(2): 155-77; Afshari et al., 1999, *Cancer Res* 59(19):4759-60) and toxicogenomics (a hybrid of functional genomics and molecular toxicology). The goal of toxicogenomics is to find correlations between toxic responses to toxicants and changes in the genetic profiles of the objects exposed to such toxicants (Nuwaysir et aL, 1999, *Molecular Carcinogenesis* 24:153-159).

In the context of the present invention, array technology can be used, for example, in the analysis of the expression of PHGDH protein or mRNA. In one embodiment, array technology may be used to assay the effect of a candidate compound on PHGDH activity.

In general, any library or group of samples may be arranged in an orderly manner into an array, by spatially separating the members of the library or group. Examples of suitable libraries for arraying include nucleic acid libraries (including DNA, cDNA, oligonucleotide, etc. libraries), peptide, polypeptide and protein libraries, as well as libraries comprising any molecules, such as ligand libraries, among others. Accordingly, where reference is made to a "library" in this document, unless the context dictates otherwise, such reference should be taken to include reference to a library in the form of an array.

The samples (e.g., members of a library) are generally fixed or immobilised onto a solid phase, preferably a solid substrate, to limit diffusion and admixing of the samples. In a preferred embodiment, libraries of DNA binding ligands may be prepared. In particular, the libraries may be immobilised to a substantially planar solid phase, including membranes and non-porous substrates such as plastic and glass. Furthermore, the samples are preferably arranged in such a way that indexing (i.e., reference or access to a particular sample) is facilitated. Typically the samples are applied as spots in a grid formation. Common assay systems may be adapted for this purpose. For example, an array may be immobilised on the surface of a microplate, either with multiple samples in a well, or with a single sample in each well. Furthermore, the solid substrate may be a membrane, such as a nitrocellulose or nylon membrane (for example, membranes used in blotting experiments). Alternative substrates include glass, or silica based substrates. Thus, the samples are immobilised by any suitable method known in the art, for example, by charge interactions, or by chemical coupling to the walls or bottom of the wells, or the surface of the membrane. Other means of arranging and fixing may be used, for example, pipetting, drop-touch, piezoelectric means, ink-jet and bubblejet technology, electrostatic application, etc. In the case of silicon-based chips, photolithography may be utilised to arrange and fix the samples on the chip.

The samples may be arranged by being "spotted" onto the solid substrate; this may be done by hand or by making use of robotics to deposit the sample. In general, arrays may be described as macroarrays or microarrays, the difference being the size of the sample spots. Macroarrays typically contain sample spot sizes of about 300 microns or larger and may be easily imaged by existing gel and blot scanners. The sample spot sizes in microarrays are typically less than 200 microns in diameter and these arrays usually contain thousands of spots. Thus, microarrays may require specialized robotics and imaging equipment, which may need to be custom made. Instrumentation is described generally in a review by Cortese, 2000, *The Scientist* 14(11):26.

Techniques for producing immobilised libraries of DNA molecules have been described in the art. Generally, most prior art methods described how to synthesise single-stranded nucleic acid molecule libraries, using for example masking techniques to build up various permutations of sequences at the various discrete positions on the solid substrate. U.S. Pat. No. 5,837,832, the contents of which are incorporated herein by reference, describes an improved method for producing DNA arrays immobilised to silicon substrates based on very large scale integration technology. In particular, U.S. Pat. No. 5,837,832 describes a strategy called "tiling" to synthesize specific sets of probes at spatially-defined locations on a substrate which may be used to produce the immobilised DNA libraries of the present invention. U.S. Pat. No. 5,837,832 also provides references for earlier techniques that may also be used.

Arrays of peptides (or peptidomimetics) may also be synthesised on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a target or probe) and reactive library members occur is determined, thereby identifying the sequences of the reactive library members on the basis of spatial location. These methods are described in U.S. Pat. No. 5,143,854; WO 90/15070 and WO 92/10092; Fodor et al., 1991, *Science* 251:767; Dower and Fodor, 1991, *Ann. Rep. Med. Chem.* 26:271.

To aid detection, targets and probes may be labelled with any readily detectable reporter, for example, a fluorescent, bioluminescent, phosphorescent, radioactive, etc reporter. Such reporters, their detection, coupling to targets/probes, etc are discussed elsewhere in this document. Labelling of probes and targets is also disclosed in Shalon et al., 1996, *Genome Res* 6(7):639-45.

Specific examples of DNA arrays include the following:

Format I: probe cDNA (~500-~5,000 bases long) is immobilized to a solid surface such as glass using robot spotting and exposed to a set of targets either separately or in a mixture. This method is widely considered as having been developed at Stanford University (Ekins and Chu, 1999, *Trends in Biotechnology,* 17:217-218).

Format II: an array of oligonucleotide (~20-~25-mer oligos) or peptide nucleic acid (PNA) probes is synthesized either in situ (on-chip) or by conventional synthesis followed by on-chip immobilization. The array is exposed to labeled sample DNA, hybridized, and the identity/abundance of complementary sequences are determined. Such a DNA chip is sold by Affymetrix, Inc., under the GeneChip® trademark. Examples of some commercially available microarray formats are set out, for example, in Marshall and Hodgson, 1998, *Nature Biotechnology* 16(1):27-31.

Data analysis is also an important part of an experiment involving arrays. The raw data from a microarray experiment typically are images, which need to be transformed into gene expression matrices—tables where rows represent for example genes, columns represent for example various samples such as tissues or experimental conditions, and numbers in each cell for example characterize the expression level of the particular gene in the particular sample. These matrices have to be analyzed further, if any knowledge about the underlying biological processes is to be extracted. Methods of data analysis (including supervised and unsupervised data analysis as well as bioinformatics approaches) are disclosed in Brazma and Vilo J, 2000, *FEBS Lett* 480(1): 17-24.

As disclosed above, proteins, polypeptides, etc may also be immobilised in arrays. For example, antibodies have been used in microarray analysis of the proteome using protein chips (Borrebaeck C A, 2000, *Immunol Today* 21(8):379-82). Polypeptide arrays are reviewed in, for example, MacBeath and Schreiber, 2000, *Science,* 289(5485):1760-1763.

Pharmaceutical Composition

A further aspect relates to a pharmaceutical composition comprising an PHGDH inhibitor or other agent identified according to any of the above-described methods admixed with a pharmaceutically acceptable diluent, excipient or carrier. In some embodiments the pharmaceutical composition further comprises one or more agents capable of inhibiting or reversing EMT (e.g. an Akt3 inhibitor or an Axl inhibitor, such as BGB324/R428).

For use according to the present invention, the agent may be presented as a pharmaceutical formulation, comprising the compounds or physiologically acceptable salt, ester or other physiologically functional derivative thereof, together with one or more pharmaceutically acceptable carriers and optionally other therapeutic and/or prophylactic ingredients.

The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients", 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active agent. A tablet may be made by compression or moulding, optionally with one or more accessory ingredients. Compressed tablets may be prepared by compressing in a suitable machine an active agent in a free-flowing form such as a powder or granules optionally mixed with a binder, lubricant, inert diluent, lubricating agent, surface-active agent or dispersing agent. Moulded tablets may be made by moulding an active agent with an inert liquid diluent. Tablets may be optionally coated and, if uncoated, may optionally be scored. Capsules may be prepared by filling an active agent, either alone or in admixture with one or more accessory ingredients, into the capsule shells and then sealing them in the usual manner. Cachets are analogous to capsules wherein an active agent together with any accessory ingredient(s) is sealed in a rice paper envelope. An active agent may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active agent is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active agent with the softened or melted carrier(s) followed by chilling and shaping in moulds.

Pharmaceutical formulations suitable for parenteral administration include sterile solutions or suspensions of an active agent in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active agent may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active agent, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active agent is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics;

advantageously the valve is of a metered type delivering a fixed volume, for example, 25 to 100 microlitres, upon each operation thereof.

As a further possibility an active agent may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active agent in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing an agent into association with a pharmaceutically or veterinarily acceptable carrier or vehicle.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier. Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific agent employed, the metabolic stability and length of action of that agent, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of agent may be administered to inhibit PHGDH. Of course, this dosage amount will further be modified according to the type of administration of the agent. For example, to achieve an "effective amount" for acute therapy, parenteral administration is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase. The agents may be administered one to four times daily at a level to achieve a total daily dose of about 0.4 to about 400 mg/kg/day. The precise amount of an active agent which is therapeutically effective, and the route by which such agent is best administered, is readily determined by one of ordinary skill in the art by comparing the blood level of the agent to the concentration required to have a therapeutic effect.

The agents of this invention may also be administered orally to the patient, in a manner such that the concentration of drug is sufficient to achieve one or more of the therapeutic indications disclosed herein. Typically, a pharmaceutical composition containing the agent is administered at an oral dose of between about 0.1 to about 50 mg/kg in a manner consistent with the condition of the patient. Preferably the oral dose would be about 0.5 to about 20 mg/kg.

The agents of this invention may be tested in one of several biological assays to determine the concentration of an agent, which is required to have a given pharmacological effect.

Kit of Parts

Another aspect of the invention relates to a kit comprising an PHGDH inhibitor, anti-Slfn11 antibody, nucleic acid probe for PHGDH or at least one QPCR primer for PHGDH, for use in any of the above-described methods.

Definitions

Axl-Related Conditions

These include, but are not limited to:

Preferably the Axl-related condition is cancer. The cancer may be one or more of the following cancers: Leukemias such as but not limited to acute myelocytic leukemias (AMLs) such as myeloblastic, promyelocytic, myelomonocytic, monocytic, erythroleukemia leukemias and myelodysplastic syndrome, acute leukemia, acute lymphocytic leukemia, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; genital cancers such as penile cancer; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. Preferably, the cancer is selected from acute myelocytic leukemia (AML), breast, melanoma, prostate, ovarian, colorectal, lung or glioma cancer; the cancer may be metastatic. Most preferably the cancer is acute myelocytic leukemias (AMLs).

Solid cancer tumors, including, but not limited to, breast, renal, endometrial, ovarian, thyroid, and non-small cell lung carcinoma, melanoma, prostate carcinoma, sarcoma, gastric cancer and uveal melanoma; liquid tumors, including but not limited to, leukemias (particularly myeloid leukemias) and lymphomas;

Leukaemias such as but not limited to, acute leukemia, acute lymphocytic leukemia, acute myeloid leukemia, acute myelocytic leukaemias such as myeloblastic, promyelocytic, myelomonocytic, monocytic, erythroleukaemia leukaemias and myelodysplastic syndrome, chronic leukaemias such as but not limited to, chronic myelocytic (granulocytic) leukemia, chronic lymphocytic leukemia, hairy cell leukemia; polycythemia vera;

Lymphomas such as but not limited to Hodgkin's disease, non-Hodgkin's disease;

Endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis, osteoporosis and cataracts;

Immune disorders, cardiovascular disorders, thrombosis, diabetes, immune checkpoint disorders, fibrotic disorders (fibrosis), or proliferative diseases such as cancer, particularly metastatic cancer. Furthermore, Axl is known to play a role in many cancers of epithelial origin;

Fibrosis (including but not limited to lung fibrosis and liver fibrosis); Fibrotic disorders of interest include strabmisus, scleroderma, keloid, Nephrogenic systemic fibrosis, pulmonary fibrosis, idiopathic pulmonary fibrosis (IPF), cystic fibrosis (CF), systemic sclerosis, cardiac fibrosis, non-alcoholic steatohepatitis (NASH), other types of liver fibrosis, primary biliary cirrhosis, renal fibrosis, cancer, and atherosclerosis. In these diseases, the chronic development of fibrosis in tissue leads to marked alterations in the architecture of the affected organs and subsequently cause defective organ function. As a result of this process of sustained attrition to organs, many diseases that involve fibrosis are often progressive conditions and have a poor long-term prognosis (see Rockey, D. C., Bell, P. D. and Hill, J. A. (2015), N. Engl. Med., Vol. 372, pp. 1138-1149);

Immune checkpoint disorders of interest include: Chronic viral infections, Melanoma, Colorectal cancer, Breast cancer, Ovarian cancer, Non-small cell lung cancer (NSCLC), Prostate cancer, Renal cell cancer, Pancreatic cancer, Esophagus cancer, Bladder cancer, Myeloma, Kidney cancer, Bladder cancer, Brain tumor, and Lymphoma.

The treatment of metastatic cancer depends on where the primary tumor is located. When breast cancer spreads to the lungs, for example, it remains a breast cancer and the treatment is determined by the metastatic cancer origin within the breast, not by the fact that it is now in the lung. About 5 percent of the time, metastatic cancer is discovered but the primary tumor cannot be identified. The treatment of these metastatic cancers is dictated by their location rather than their origin. Metastatic cancers are named by the tissue of the original tumor (if known). For example, a breast cancer that has spread to the brain is called metastatic breast cancer to the brain.

Agent Capable of Inhibiting or Reversing EMT/EMT Inhibitor

The terms "agent capable of inhibiting EMT" and "EMT inhibitor" are used interchangeably herein to mean an agent that prevents or reduces the rate of the EMT transition.

The term "agent capable of reversing EMT" is used herein to denote an agent which promotes the reverse of EMT, that is, promotes the Mesenchymal-to-epithelial (MET) transition.

Examples of EMT inhibitors include inhibitors of the Axl kinase (Axl inhibitors) and inhibitors of the Akt3 kinase (Akt3 inhibitors). Accordingly, in some embodiments the EMT inhibitor is an Axl inhibitor. In some embodiments the EMT inhibitor is an Akt3 inhibitor. In some embodiments the EMT inhibitor is a PHGDH inhibitor.

Conversely, in some embodiments the EMT inhibitor is not an Axl inhibitor. In some embodiments the EMT inhibitor is not an Akt3 inhibitor. In some embodiments the EMT inhibitor is neither an Axl inhibitor nor an Akt3 inhibitor. In some embodiments the EMT inhibitor is not a PHGDH inhibitor.

Statements of Invention

1. A method of identifying a subject having an Axl-related condition, the method comprising assessing the level of expression or activity of PHGDH in the subject, or in a sample derived from the subject.

2. A method according to statement 1 of identifying a subject having a particular risk of developing metastatic or drug-resistant cancer, the method comprising assessing the level of expression or activity of PHGDH in the subject, or in a sample derived from the subject, an increased level of PHGDH expression or activity indicating an increased risk of the subject of developing metastatic or drug-resistant cancer.

3. A method according to statement 1 of identifying the presence of a Cancer Stem Cell in a subject, the method comprising determining the level of PHGDH expression or activity in the subject, or in a sample derived from the subject, increased expression or activity of Slfn11 indicating the existence of a Cancer Stem Cell (CSC).

4. A method according to statement 1 of identifying a subject undergoing epithelial-to-mesenchymal transition (EMT), the method comprising determining the level of PHGDH expression or activity in the subject, or in a sample derived from the subject, an increase in expression or activity of PHGDH indicating the occurrence of EMT.

5. A method of prognosing a cancer-related outcome in a subject, the method comprising assessing the activity or expression of one or more biomarker in the subject, or in a sample derived from the subject;
  wherein the one or more biomarker is selected from the group consisting of Axl, Akt, Erk, PLCγ, PHGDH, and SLFN11.

6. A method according to statement 5, wherein an increase in the activity or expression of one or more biomarker relative to a control sample is indicative of susceptibility to treatment with an agent capable of inhibiting or reversing EMT, or of increased susceptibility to a chemotherapeutic agent.

7. A method according to statement 5, wherein an increase in the activity or expression of one or more biomarker relative to a control sample after contacting the subject with a cancer therapeutic agent is indicative of decreased susceptibility to treatment with an agent capable of inhibiting or reversing EMT, or of decreased susceptibility to a chemotherapeutic agent.

8. A method according to statement 5, wherein a decrease in the activity or expression of one or more biomarker relative to a control sample after contacting the subject with a cancer therapeutic agent is indicative of increased susceptibility to treatment with an agent capable of inhibiting or reversing EMT, or of increased susceptibility to a chemotherapeutic agent.

9. A method according to any one of statements 6 to 8, wherein the agent capable of inhibiting or reversing EMT is an Axl inhibitor, Akt3 inhibitor, or PHGDH inhibitor.

10. A method of identifying Axl activity, the method comprising determining the level of PHGDH expression or activity in the subject, or in a sample derived from the subject, increased expression or activity of PHGDH correlating with Axl activity.

11. A method according to any one of statements 1 to 10 in which the subject is mammalian.

12. A method according to statement 11 in which the subject is human.

13. A method according to any one of statements 1 to 12, wherein the level of expression or activity in the subject or sample derived from the subject is determined relative to a control sample.

14. A method according to any one of statements 1 to 13, wherein the level of expression of PHGDH is assessed by determining the copy number of the gene encoding PHGDH relative to a control sample, wherein an increase in the copy number indicates an increased level of expression of Axl.

15. A method according to any one of statements 1 to 14, wherein the level of expression of PHGDH is assessed by determining the level of PHGDH protein or mRNA.

16. A method of selecting patients, preferably human patients, for treatment of an Axl-related condition, the method comprising identifying patients having elevated PHGDH activity or expression and selecting thus identified patients for treatment.

17. A method of selecting patients, preferably human patients, for treatment of an Axl-related condition, the method comprising identifying patients having decreased activity or expression of one or more biomarker relative to a control sample after contact the patient with a cancer therapeutic agent, and selecting thus identified patients for treatment;
  wherein the one or more biomarker is selected from the group consisting of Axl, Akt, Erk, PLCγ, PHGDH, and SLFN11.

18. A method of selecting patients according to and one of statements 5 to 8 or statement 17 in which the cancer therapeutic agent is an agent capable of inhibiting or reversing EMT, such as an Axl inhibitor.

19. A method according to any one of statements 5 to 8 or 17 to 18 wherein the one or more biomarker is PHGDH.

20. A method according to any one of statements 5 to 8 or 17 to 19 wherein the one or more biomarker is:
  (i) SLFN11;
  (ii) PLCγ1;
  (iii) ERK;
  (iv) Axl;
  (v) Akt;
  (vi) PHGDH, PLCγ1, and SLFN11; or
  (vii) Axl, Akt, Erk, PLCγ1, PHGDH, and SLFN11.

21. A method of selecting patients according to any one of statements 16 to 20 which the Axl-related condition is cancer.

22. A method according to any one of statements 16 to 21, wherein the patient is identified according to a method of any one of statements 1 to 15.

23. A method according to any one of statements 16 to 22, wherein the treatment comprises administering an agent capable of inhibiting or reversing EMT.

24. A method according to statement 23, wherein the agent comprises a PHGDH inhibitor, an Akt3 inhibitor, or an Axl inhibitor.

25. A method according to any one of statements 1 to 24, wherein the cancer or Axl-related condition is a cancer selected from acute myelocytic leukemia (AML), breast, melanoma, prostate, ovarian, colorectal, lung or glioma cancer.

26. A PHGDH inhibitor for use in the treatment of an Axl-related condition.

27. A PHGDH inhibitor according to statement 26 in which the condition is cancer.

28. A PHGDH inhibitor for use in the inhibition of EMT.

29. A compound capable of inhibiting activity for use in the prevention, inhibition, or treatment of drug resistance in a subject having cancer, the method comprising contacting the subject with a compound capable of inhibiting PHGDH activity or expression.

30. A PHGDH inhibitor according to any one of statements 27 to 29 in combination with another therapeutic agent.

31. A PHGDH inhibitor according to statement 30, wherein the other therapeutic agent is an EMY inhibitor, such as an Axl inhibitor.

32. A method of treating a subject having an Axl-related condition, the method comprising contacting the subject with a PHGDH inhibitor or pharmaceutical compound selected as, or derived from, a candidate compound obtained by a method according to any one of statements 44 to 48.

33. A method of treatment of a subject according to statement 32 having an Axl-related condition, the method comprising periodically assessing PHGDH activity or expression in the subject.

34. A method according to one of statements 32 to 33 in which the Axl-related condition is cancer.

35. A method according to one of statements 32 to 34 in which treatment of the subject is adjusted according to detected levels of PHGDH activity or expression.

36. A method according to any one of statements 26 to 29 in which the subject is being treated with a PHGDH inhibitor, a Slfn11 inhibitor, an Axl inhibitor, or an Akt3 inhibitor.

37. A method of inhibiting EMT in a subject, the method comprising contacting the subject with a compound capable of inhibiting PHGDH activity or expression.

38. A method of inhibiting Cancer Stem cells in a subject, the method comprising contacting the subject with a compound capable of inhibiting PHGDH activity or expression.

39. A method according to any one of statements 32 to 38 in which the subject is also contacted with another cancer therapeutic, such as an EMT inhibitor or an Axl inhibitor.

40. A method of preventing or inhibiting drug resistance in a subject having cancer, the method comprising contacting the subject with a compound capable of modulating PHGDH activity or expression.

41. A method according to any one of statements 32 to 40 in which the subject is mammalian.

42. A method according to statement 41 in which the subject is human.

43. A PHGDH inhibitor according to any one of statements 26 to 31, or a method of treatment according to any one of statements 39 to 42 in which the other therapeutic agent is a cancer treatment selected from alkylating agents, including alkyl sulfonates such as busulfan, nitrogen mustards such as chlorambucil, cyclophosphamide, estramustine, ifosfamide, mechlorethamine, melphalan, and uramustine, ethyleneimine derivatives such as thiotepa, nitrosoureas such as carmustine, lomustine, and streptozocin, triazenes such as dacarbazine, procarbazine, and temozolamide, platinum compounds such as cisplatin, carboplatin, oxaliplatin, satraplatin, and picoplatin onnaplatin, tetraplatin, sprioplatin, iproplatin, chloro(diethylenediamino)-platinum (II) chloride, dichloro(ethylenediamino)-platinum (II), diamino(2-ethylmalonato)platinum (II), (1,2-diaminocyclohexane)malonatoplatinum (II), (4-carboxyphthalo)-(1,2-diaminocyclohexane)platinum (II), (1,2-diaminocyclohexane)-(isocitrato)platinum (II), and (1,2-diaminocyclohexane)-cis-(pyruvato)platinum (II); antimetabolites, including antifolates such as methotrexate, permetrexed, raltitrexed, and trimetrexate, pyrimidine analogues such as azacitidine, capecitabine, cytarabine, edatrexate, floxuridine, fluorouracil, gemcitabine, and troxacitabine, and purine analogues such as cladribine, chlorodeoxyadenosine, clofarabine, fludarabine, mercaptopurine, pentostatin, and thioguanine; natural products, including antitumor antibiotics such as bleomycin, dactinomycin, mithramycin, mitomycin, mitoxantrone, porfiromycin, and anthracyclines such as daunorubicin, doxorubicin, epirubicin, idarubicin, and valrubicin, mitotic inhibitors such as the vinca alkaloids vinblastine, vinvesir, vincristine, vindesine, and vinorelbine, enzymes such as L-asparaginase and PEG-L-asparaginase, microtubule polymer stabilizers such as the taxanes paclitaxel and docetaxel, topisomerase I inhibitors such as the camptothecins irinotecan and topotecan, and topoisomerase II inhibitors such as podophyllotoxin, amsacrine, etoposide, teniposide, losoxantrone and actinomycin; hormones and hormone antagonists, including androgens such as fluoxymesterone and testolactone, antiandrogens such as bicalutamide, cyproterone, flutamide, and nilutamide, corticosteroids such as dexamethasone and prednisone, aromatase inhibitors such as aminoglutethimide, anastrozole, exemestane, formestane, and letrozole: estrogens such as diethylstilbestrol, antiestrogens such as fulvestrant, raloxifene, tamoxifen, and toremifine, luteinising hormone-releasing hormone (LHRH) agonists and antagonists such as abarelix, buserelin, goserelin, leuprolide, histrelin, desorelin, nafarelin acetate and triptorelin, progestins such as medroxyprogesterone acetate and megestrol acetate, and thyroid hormones such as levothyroxine and liothyronine; PKB pathway inhibitors, including perifosine, enzastaurin hydrochloride, and triciribine, P13K inhibitors such as semaphore and SF1126, and MTOR inhibitors such as rapamycin and analogues; CDK inhibitors, including seliciclib, alvocidib, and 7-hydroxystaurosporine; COX-2 inhibitors, including celecoxib; HDAC inhibitiors, including trichostatin A, suberoylanilide hydroxamic acid, and chlamydocin; DNA methylase inhibitors, including temozolomide, and miscellaneous agents, including altretamine, arsenic trioxide, thalidomide, lenalidomide, gallium nitrate, levamisole, mitotane, hydroxyurea, octreotide, procarbazine, suramin, photodynamic compounds such as methoxsalen and sodium porfimer, and proteasome inhibitors such as bortezomib: molecular targeted therapy agents including: functional therapeutic agents, including gene therapy agents, antisense therapy agents, tyrosine kinase inhibitors such as erlotinib hydrochloride, gefitinib, imatinib mesylate, and semaxanib, Raf inhibitors such as sorafenib, and gene expression modulators such as the retinoids and rexinoids, for example adapalene, bexarotene, trans-retinoic acid, 9-cis-retinoic acid, and N-(4-hydroxyphenyl)retinamide; and phenotype-directed therapy agents, including monoclonal antibodies such as alemtuzumab, bevacizumab, cetuximab, ibritumomab tiuxetan, rituximab, and trastuzumab, immunotoxins such as gemtuzumab ozogamicin, radioimmunoconjugates such as I-tositumobab, and cancer vaccines; Biologic therapy agents including: interferons such as interferon-[alpha]2a and interferon-[alpha]2b, and interleukins such as aldesleukin, denileukin diftitox, and oprelvekin anticancer therapies involving the use of protective or adjunctive agents, including: cytoprotective agents such as amifostine, and dexrazoxane, phosphonates such as pamidronate and zoledronic acid, and stimulating factors such as epoetin, darbeopetin, filgrastim, PEG-filgrastim, and sargramostim; and Axl inhibitor such as 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine; or further combination chemotherapeutic regimens, such as combinations of carboplatin/paclitaxel, capecitabine/docetaxel, fluorauracil/levamisole, fluorauracil/leucovorin, methotrexate/leucovorin, and trastuzumab/paclitaxel, alone or in further combination with carboplatin, and the like.

44. A method of selecting a pharmaceutical compound useful for the prevention, inhibition or treatment of an Axl-related condition, the method comprising providing a group of candidate pharmaceutical compounds for testing, testing the effect of candidate pharmaceutical compounds on PHGDH activity or expression in a test system, and selecting a candidate pharmaceutical compound on the basis of modulating PHGDH activity or expression.

45. A method of selecting a candidate pharmaceutical compound useful in the treatment of metastatic or drug resistant cancer, the method comprising providing a group of candidate pharmaceutical compounds for testing, testing the effect of candidate pharmaceutical compounds on PHGDH activity or expression in a test system, and selecting a candidate pharmaceutical compound on the basis of its modulation of PHGDH activity or expression.

46. A method of selecting a candidate pharmaceutical compound useful in the prevention or inhibition of EMT, the method comprising providing a group of candidate pharmaceutical compounds for testing, testing the effect of candidate pharmaceutical compounds on PHGDH activity or expression in a test system, and selecting a candidate pharmaceutical compound on the basis of modulating PHGDH activity or expression.

47. A method of selecting a candidate pharmaceutical compound useful in the prevention, inhibition or treatment of an Axl-related condition, the method comprising selectively reducing expression of PHGDH in a test cell, contacting the test cell with the candidate pharmaceutical compound and determining the effect of the candidate pharmaceutical compound on the modulation of PHGDH activity or expression.

48. A method of selecting a candidate pharmaceutical compound useful in the prevention, inhibition or treatment of an Axl-related condition, the method comprising selectively reducing expression of PHGDH in an in vitro test system to a low level contacting the test system with a candidate pharmaceutical compound, and selecting candidate pharmaceutical compounds which modulate PHGDH activity or expression.

49. A method according to any one of statements 44 to 48 in which candidate pharmaceutical compounds which substantially or completely inhibit PHGDH activity or expression are selected.

50. A method of selecting candidate pharmaceutical compounds according to statement 47, 48 or 49 in which inhibition of PHGDH activity or expression is indicated by a reduction in EMT.

51. A method according to any one of statements 46 to 50 in which the expression of PHGDH in cells in the test system is reduced by 90%, 80%, 70%, 60%, 50%, 40%, 30%, or 20%.

52. A method according to statement 51 in which the expression of PHGDH is reduced so as to not cause inhibition of EMT.

53. A method according to any one of statements 46 to 52 in which the expression of PHGDH is selectively reduced by introducing into cells in the test system a nucleotide which interferes with expression of PHGDH.

54. A cell line which is sensitive to inhibitors of EMT, the cell line having a level of PHGDH expression that is just insufficient to prevent EMT.

55. A cell line according to statement 54 which is a human cell line.

56. A method of identifying a compound which inhibits PHGDH activity or expression, the method comprising contacting a cell from a cell line according to statement 54 or 55 with a test compound and determining inhibition of PHGDH activity or expression in the cell.

57. A method according to statement 56 in which inhibition of PHGDH activity or expression is identified by inhibition of EMT.

58. Use of PHGDH as a biomarker for detecting the occurrence of epithelial-to-mesenchymal transition (EMT) in a subject.

59. Use according to statement 58 wherein an increase in the expression and/or activation of PHGDH is indicative of the occurrence of epithelial-to-mesenchymal transition (EMT).

60. Use of PHGDH as a biomarker for detecting the expression and/or activation of Axl, wherein an increase in the expression and/or activation of PHGDH is indicative of an increase in the expression and/or activation of Axl.

61. A method for detecting the occurrence of epithelial-to-mesenchymal transition (EMT) in a sample, said method comprising
determining the expression level or activation of PHGDH in a sample isolated from a cell, group of cells, an animal model or human as compared to a control sample, wherein an increase in the expression level or activation of PHGDH relative to the control sample is indicative of the occurrence of epithelial-to-mesenchymal transition (EMT).

62. A method for identifying an agent capable of inhibiting or reversing epithelial-to-mesenchymal transition (EMT), said method comprising administering said agent to a cell, group of cells or animal model, and monitoring the activation and/or the expression of PHGDH.

63. A method according to statement 62 which comprises:
(i) administering the agent to a cell, group of cells or an animal model, not a human; and
(ii) measuring PHGDH expression and/or PHGDH activation in samples derived from the treated and the untreated cells or animal model; and
(iii) detecting an increase in the expression and/or activation of PHGDH in the treated sample as compared to the untreated sample as an indication of the ability to inhibit or reverse epithelial-to-mesenchymal transition (EMT).

64. A method according to statement 62 or statement 63, wherein the animal model is not a human.

65. A use or method according to any one of statements 59 to 64 wherein the level of expression of PHGDH is assessed by determining the copy number of the gene encoding PHGDH relative to a control sample, wherein an increase in the copy number indicates an increased level of expression of PHGDH.

66. A use or method according to any one of statements 58 to 65 wherein the level of expression of PHGDH is assessed by determining the level of PHGDH protein or mRNA.

67. Use of a PHGDH inhibitor in the manufacture of a medicament for the treatment of an Axl-related condition.

68. Use according to statement 67 in which the condition is cancer.

69. Use of a PHGDH inhibitor in the manufacture of a medicament for the inhibition of EMT.

Figure 21:
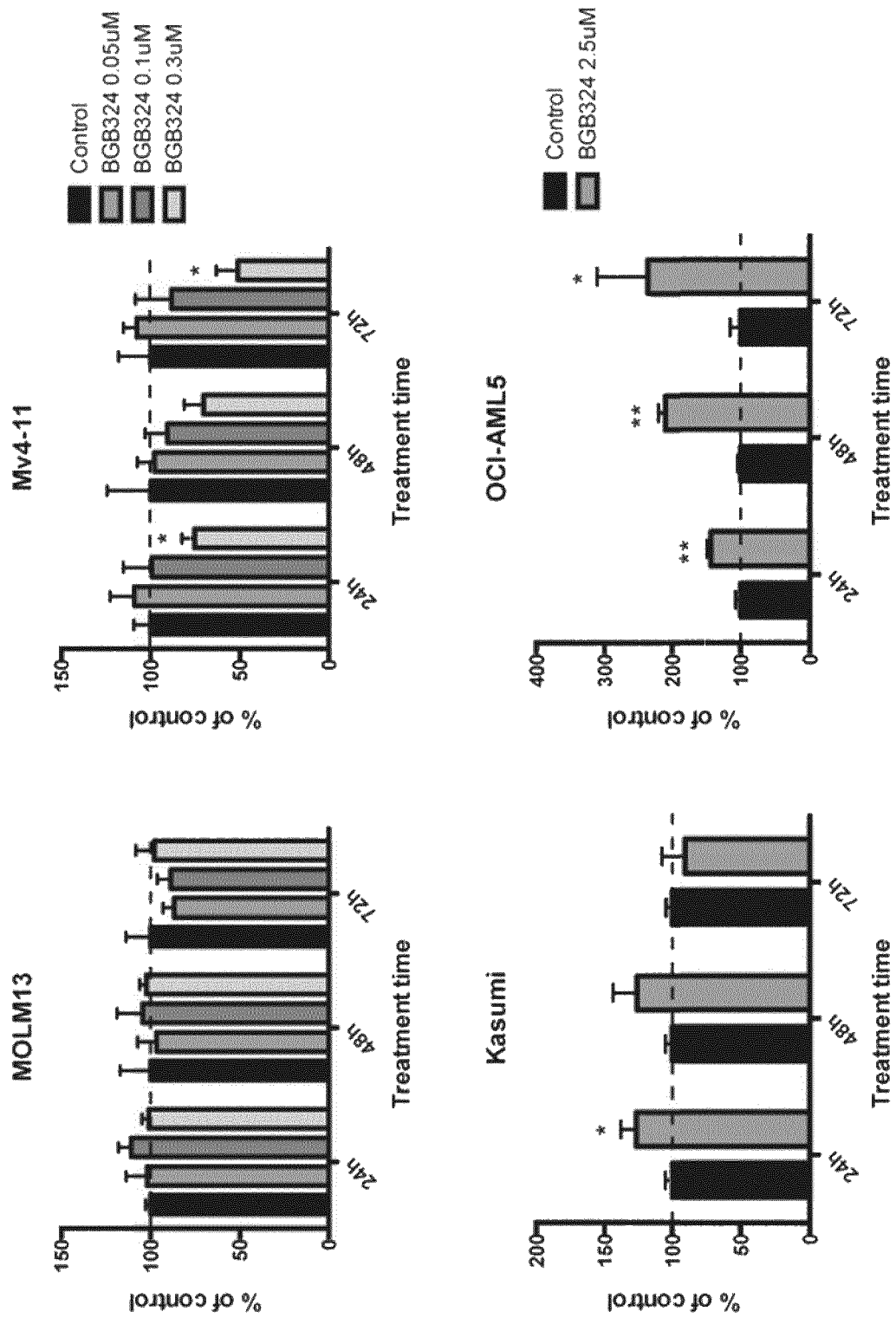

FIG. 21: Response in totPHGDH in AML cell lines after 24, 48 and 72 hours of treatment with BGB324 at 0.05, 0.1 or 0.3 µM (MOLM13 and Mv4-11, upper panels) or at 2.5 µM (Kasumi and OCI-AML5, lower panels). The graphs show geometric mean of fluorescence, calculated as % of control (which is set to 100%—indicated by a dotted line), ±SEM. * indicates significance relative to control, calculated using a two-tailed Student's t-test. *p<0.05, **p<0.005, n=3.

Figure 22:
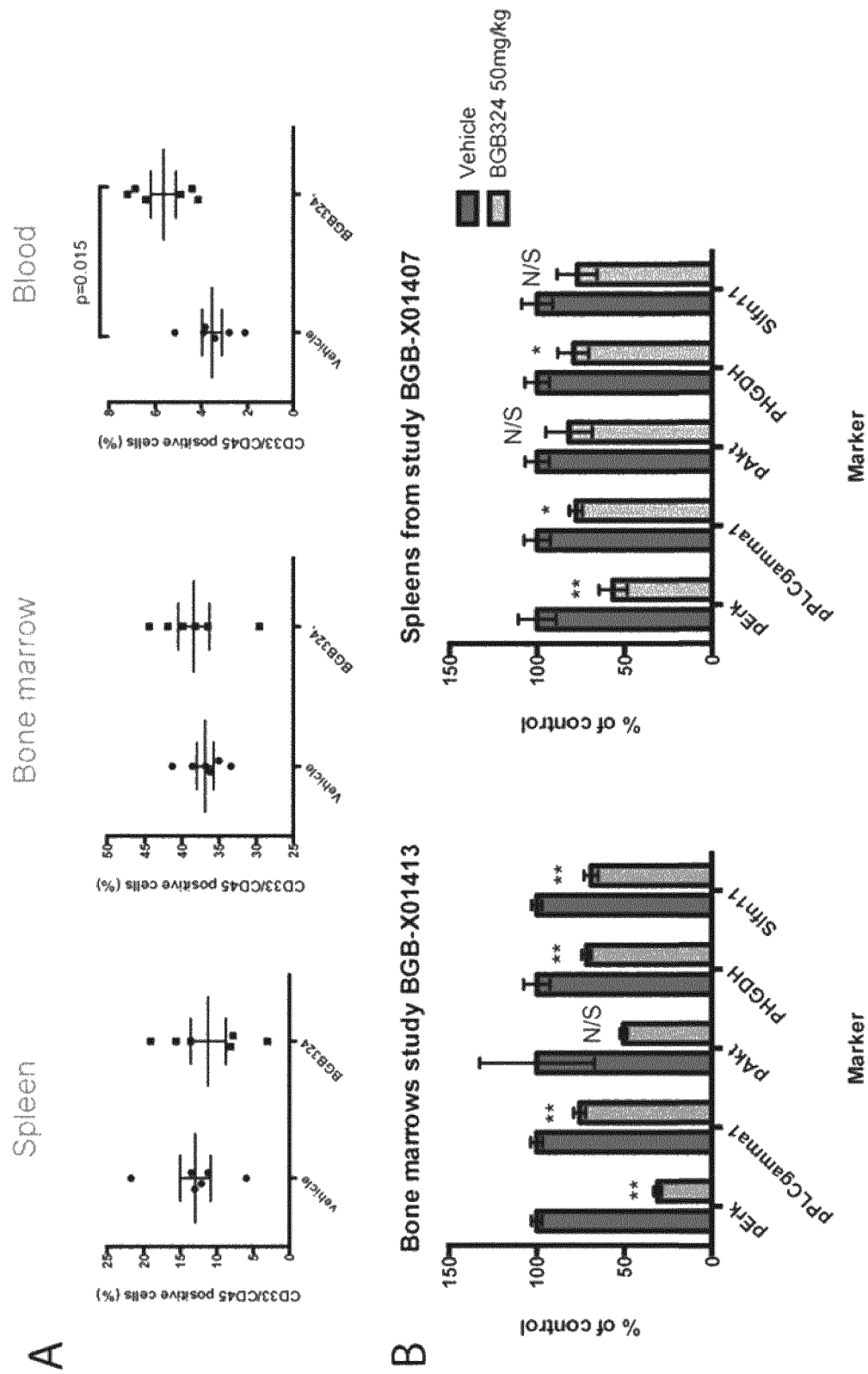

FIG. 22: Spleen, bone marrow and blood from mice was stained with anti-human-CD33 and -CD45 antibodies to identify leukemic cells in the tissues. CD33/CD45 double-positive cells were quantified as % of total live cell count (A). Bone marrows and spleens from treated and non-treated mice were assessed for biomarker expression by flow cytometry. The samples were stained with anti-human CD33 antibody, and biomarker expression was only evaluated in CD33-positive cells (B). The graphs show geometric mean of fluorescence, calculated as % of control (which is set to 100%), ±SEM. * indicates significance relative to control, calculated using a two-tailed Student's t-test. *p<0.05, **p<0.005, n≥5.

The invention will now be described in more detail, by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the spirit and scope of the invention. All documents cited herein are expressly incorporated by reference.

EXAMPLES

Materials

10% NuPAGE® Bis-Tris precast gels (#NP0301 BOX, Invitrogen)
Alkaline Phosphatase, Calf Intestinal (CIP) (#M0290, New England Biolabs)
Amersham Hybond-P PVDF transfer membrane (#RPN303F, GE Healthcare)
Anti-PHGDH antibody (mouse monoclonal, ab57030, Abcam, BGB #133)
Anti-PLCgamma1 antibody (mouse monoclonal [M156], ab41433, Abcam, BGB #152)
APC Mouse Anti-Human CD33 Clone WM53 (551378 BD, BGB #2-45)
BGB324 (Manufacturer: Almac Group, N Ireland. Lot #011-SR-324 DA2al-15.
  Drug was dissolved in DMSO for a main stock concentration at 10 mM. Working stock was made by diluting main stock in DMSO to 1 mM stock, which was further diluted in sterile water to a final concentration of 100 µM. All stocks were kept at −20° C.
Complete Mini Protease Inhibitor Cocktail tablets (#04693116001, Roche)
ECL-reagents: Reagent1 and Reagent2 (#1859701 and #1859698, Thermo Scientific)
EDTA Vacutainers (BD Biosciences)
Fetal Bovine Serum (FBS, #A9647, Sigma)
Goat anti-Mouse IgG (H+L) Secondary Antibody, Pacific Blue conjugate (P-10993, Invitrogen, BGB #2-7)
Goat anti-Rabbit IgG (H+L) Secondary Antibody, Alexa Fluor® 488 conjugate (A11008 Invitrogen, BGB #2-11)
MagicMark™ XP Western Protein Standard (#LC5602, Invitrogen)
Mouse-anti-human Axl Ab (10C9, Genovac, BGB #31)
Mouse-anti-human Axl Ab (1H12-1B7-5D6, BerGenBio, BGB #47)
Mouse-anti-human Axl Ab (1H12-1B7-5D6, BerGenBio, BGB #47) Alexa 647-conjugated (1.2 mg/ml in PBS. Stock: 22 Oct. 2013, made by Hallvard Haugen)
Mouse-anti-human pAxl Y779 Ab (MAb6965, R&D Systems)
Mouse-anti-human SLFN11 Ab (sc-374339, Santa Cruz, BGB #91)
NEBuffer3 (#B7003S, New England Biolabs)
Nitrocellulose membrane, Whatman Protran BA85 (#10401196, GE Healthcare)
NP-40: Pierce IP lysis buffer (#87788, Thermo Scientific)
NuPAGE Antioxidant (#NP0005, Invitrogen)
NuPAGE LDS Sample Buffer 4× (#NP0007, Invitrogen)
Octagam, 50 mg/ml (#430215, Octapharma)
p44/42 MAPK (Erk1/2) (137F5) (Rabbit monoclonal, #4695 Cell Signaling, BGB #78)
PE-Cy™7 Mouse Anti-Human CD45 Clone HI30 (557748 BD, BGB #2-46)
Phospho-p44/42 MAPK (Erk1/2) (Thr202/Tyr204) (D13.14.4E) XP® (Rabbit monoclonal, #4370, Cell Signaling, BGB #53)Phospho-P LCγ1 (Tyr783) (D6M9S) (Rabbit monoclonal #14008, Cell Signaling, BGB #144)
phosSTOP Phosphatase Inhibitor Cocktail tablets (#04693116001, Roche)
Pierce BCA protein assay kit (#PI-23227, Thermo Scientific)
Rabbit anti actin Ab (#A5060, Sigma-Aldrich)
Rabbit-anti-human pAkt S473 Ab (#4060, Cell Signaling Technology)
SeeBlue® Plus 2 Pre-Stained Standard (#LC5625, Invitrogen)

Cells

MOLM13 cells were grown in RPMI-1640 media (R8758, Sigma-Aldrich), supplemented with 10% fetal bovine serum (FBS), L-glutamine (4 mM) and penicillin-streptomycin (5 µg/ml).

The MOLM13 cell line carries a Flt3-ITD-mutation. In addition to MOLM13 wt cells, MOLM13 espressing an shAxl- (BG123) or shLuc (L108, as a control for the BG123-construct) construct were used to examine whether changes observed in these cells after BGB324-treatment was Axl-specific.

Mv4-11 cells (ATCC, CRL9591) were grown in Isovec's Modified Dulbecco's Medium (IMDM; #30-2005, ATCC) supplemented with 10% fetal bovine serum (FBS), L-glutamine (4 mM), streptomycin (5 µg/ml) and penicillin (5 U/ml).

OCI-M1 cells were grown in Isovec's Modified Dulbecco's Medium (IMDM; #30-2005, ATCC) supplemented with 20% fetal bovine serum (FBS), L-glutamine (4 mM), streptomycin (5 µg/ml) and penicillin (5 U/ml).

OCI-AML3 cells were grown in Alpha MEM (#22561-021, Gibco by Life Technologies) supplemented with 20% fetal bovine serum (FBS), L-glutamine (4 mM), streptomycin (5 µg/ml) and penicillin (5 U/ml).

OCI-AML5 cells were grown in Alpha MEM (#22561-021, Gibco by Life Technologies) supplemented with 20% fetal bovine serum (FBS), L-glutamine (4 mM), streptomycin (5 µg/ml), penicillin (5 U/ml), and GM-CSF (2.5 ng/ml).

Kasumi cells were grown in RPMI-1640 media (R8758, Sigma-Aldrich) supplemented with 20% fetal bovine serum (FBS), L-glutamine (4 mM), streptomycin (5 µg/ml) and penicillin (5 U/ml).

Methods

Western Blot, General Protocol:

For western blot analysis, cells were lysed on ice using NP-40 lysis buffer with protease- and phosphatase inhibitors. Total protein concentration in lysates was measured using a BCA protein assay kit following the manufacturers instructions. 10% NuPAGE® Bis-Tris precast gels were loaded with 30-50 µg of protein in each well diluted in sample buffer and antioxidant. A 1:1 mix of MagicMark™ XP Western Protein Standard (Invitrogen) and SeeBlue® Plus 2 Pre-Stained Standard was used as protein standard. Gels were run at 50V for 20 min, then at 100V for 1 h 30 min. Blotting was done on ice for 1 h 30 min at 100V onto PVDF (pre-activated with MeOH) or nitrocellulose membranes. Membranes were washed in TBS-0.1% Tween-20 (TBS-T), and blocked in TBS-T 5% BSA for at least 1 h at RT. Primary ABs were added at 1:1000 in TBS-T 5% BSA (rabbit-anti-actin AB was added at 1:2000) in TBS-T 5% BSA, and membranes were incubated over night at 4° C. Membranes were then washed 3× in TBS-T, and incubated in HRP-conjugated secondary ABs at 1:5000 dilution in TBS-T 5% milk for 45 min at RT. Membranes were developed for 1 min using ECL-reagents and imaged with chemiluminescence using a Molecular Imager ChemiDoc™ XRS (BioRad). All incubation- and washing steps were done on a roller.

Staining of Cells for Flow Cytometry, General Protocol:

Live cells were centrifuged at 300 G for 5 minutes, washed once with PBS and centrifuged again. Cells were then fixed in 4% PFA in PBS for 10 minutes at 37° C., and resuspended in PBS. Unless processed immediately, samples were at this point stored in PBS at 4° C. (up to three weeks) or at −80° C. (for long-term storage). If intracellular epitopes were stained, cells were permebealized in 90% MeOH for 30 minutes on ice. Unless processed immediately, samples were also be stored in 90% MeOH at −20° C. for up to two months.

Further staining procedure (permebealized or non-permebealized cells):

Cells were washed 1× in PBS and blocked in blocking buffer; either PBS+0.5% BSA or PBS+1:1000 Octagam (5 mg/ml) for 15 minutes at room temperature. Thereafter, cells were incubated with primary AB at the indicated dilutions in incubation buffer (IB, PBS+0.5% BSA) for 1 hour at room temperature. Cells were then washed 3× with IB and incubated with secondary AB (conjugated to a fluorescent flurophore) at 1:1000 dilution in IB for 30 minutes at room temperature. Finally, cells were washed 3× in IB and resuspended in PBS. Cells were analyzed immediately, or stored for up to 24 hours at 4° C. before analysis.

Analysis of cells was done on a BD LSR Fortessa or a BD C6 Accuri flow cytometer, and further processing was done using FlowJo v.7.6.

All incubation steps (but not storage) were done on a spinning wheel or gentle shaker.

Treatment of Cells with Alkaline Phosphatase:

In order to test the specificity of phospho-antibodies for flow cytometry, fixed cells were in some experiments treated with alkaline phosphatase to remove phosphorylation on all phospho-sites. These samples were used as negative staining controls.

Cells were fixed as described above, and washed 1× in PBS. Cells were then pelleted, and resuspended 495 µl 1× NEBuffer3 and 5 µl 1% Alkaline phosphatase (CIP) (stock 10 000 U/ml), and incubated at 37° C. for 1 hour. The cells were then pelleted again, resuspended in blocking buffer, and blocked and stained for flow cytometry, as described above.

Staining of Blood for Flow Cytometry, General Protocol:

Human blood from healthy donors was collected in the presence of sodium citrate and mixed with 20 volumes of pre-warmed BD phosflow lyse/fix buffer (diluted to 1× in destilled water), followed by incubation in 37° C. water bath for 10 minutes. Cells were spun at 500 g for 8 minutes and washed once with PBS.

Cells were permebilized by adding 70% MeOH followed by 30 min incubation on ice. Unless processed immediately, samples were at this point stored in MeOH at −20° C. for up to 4 weeks.

Staining of permeabilized cells:

Cells were spun at 600 g, washed twice and resuspended in IB. Cells were aliquoted into volums corresponding to 100 ul collected blood (before dilution), and stained as described above (section two in "Staining of cells for flow cytometry, general protocol").

All washing and incubation steps were done on a spinning wheel or gentle shaker.

Example 1

Evaluation of Phospho-Akt as a Potential Biomarker in AML

MOLM13 cells were treated with BGB324 at different doses, and phosphorylation of Akt at the S473 phosphorylation site was assessed using a pAkt (S473) XP antibody from Cell Signaling Technology (#4060, BGB #109). Due to previous experience using this AB for flow, the AB was not titrated, but used at the concentration recommended by the manufacturer for flow cytometry.

MOLM13 cells were cultured in starvation medium (RPMI, 0.1% FBS) over night, pre-treated with BGB324 at 3 µM for 20 minutes, and thereafter stimulated with 10% FBS for 20 minutes (+/−BGB324) to induce Akt phosphorylation. MOLM13 cells carry the Flt3 ITD-mutation, and therefore have constitutively active Flt3 and hence also constitutively active Akt.

Figure 1:
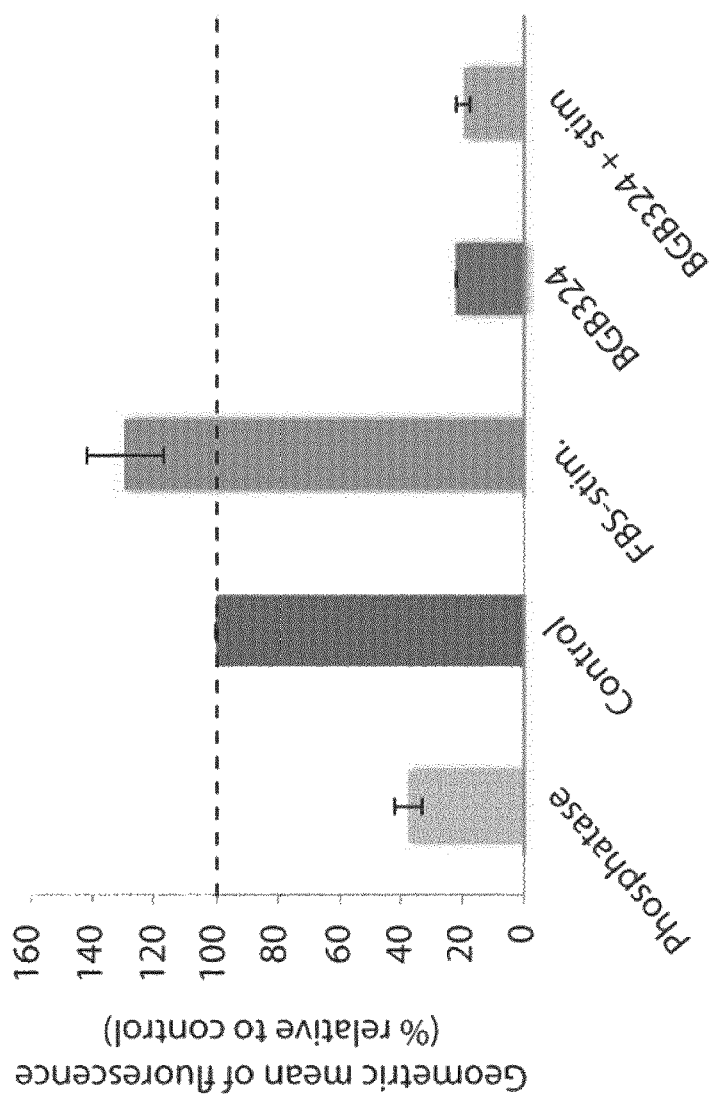
FIG. 1: Assessment of pAkt(S473) in MOLM13 cells by flow cytometry after overnight starvation and treatment with 3 uM BGB324 for 1 hour+/−20 minutes FBS-stimulation. The graph shows quantification of geometric mean of fluorescence, calculated as % relative to control (starved cells. Set to 100%, indicated by a dotted line). N=2.
Figure 1:
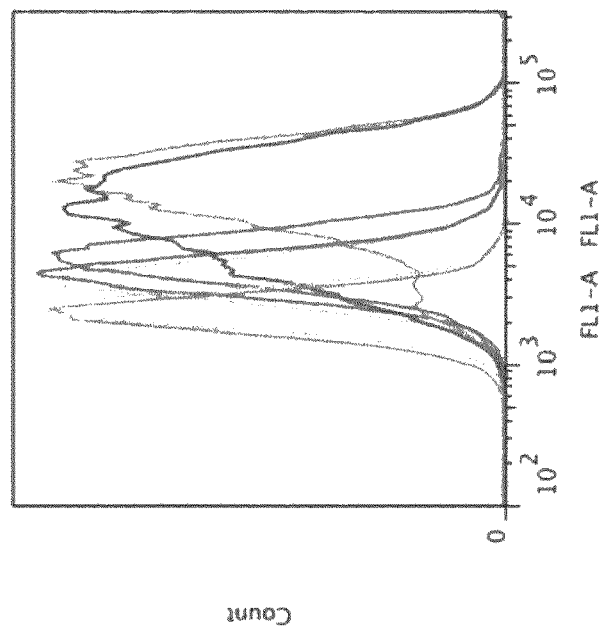
Figure 2A:
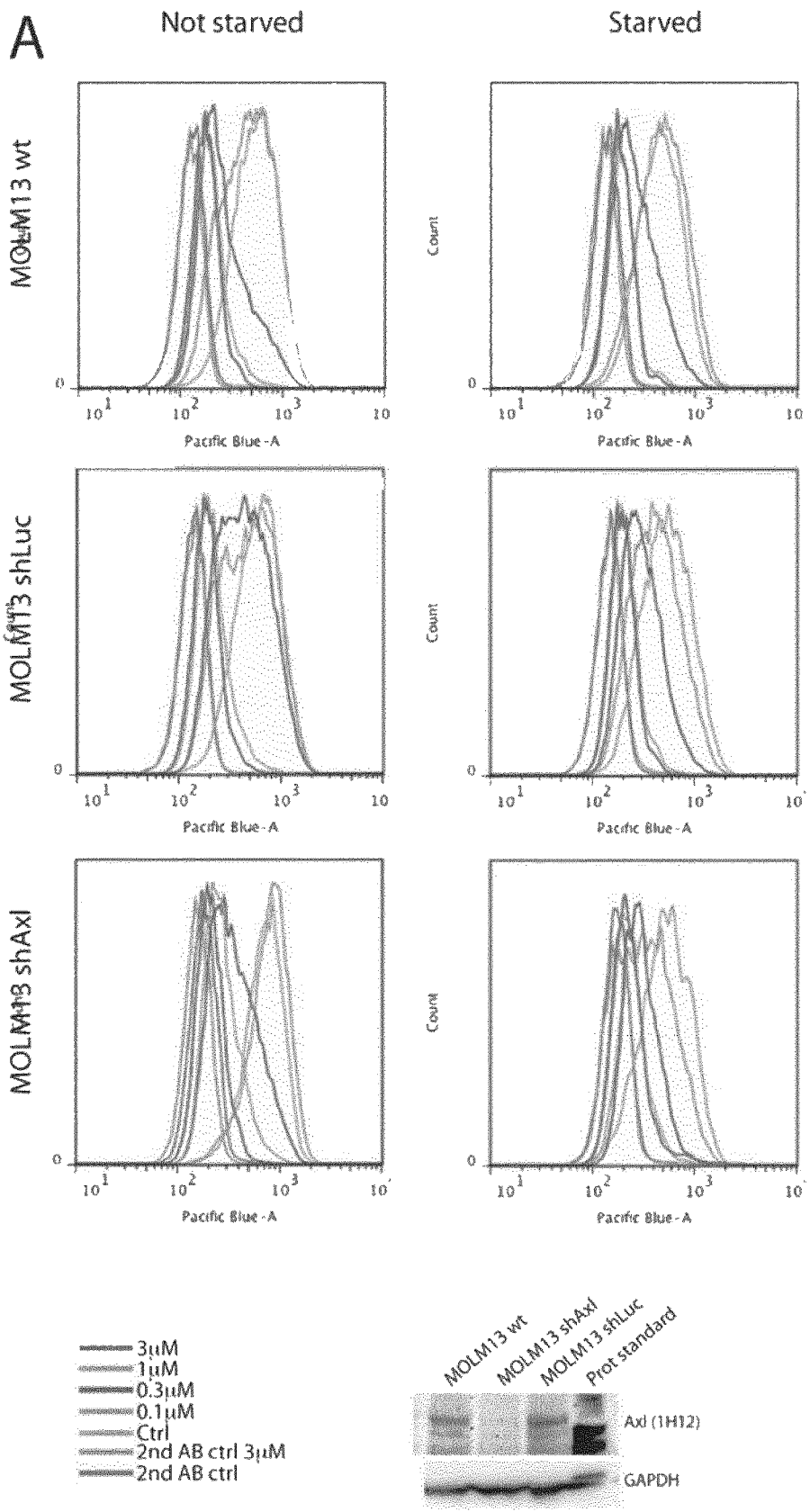
FIG. 2: Histograms showing pAkt(S473) dose-response of BGB324 in MOLM13 wt, shLuc and shAxl. Starved cells are compared to non-starved cells (A). The geometrig mean of fluorescence was also quantified in non-starved (B) and starved (C) cells. The graphs show % change relative to control (set to 100%).
Figure 2B:
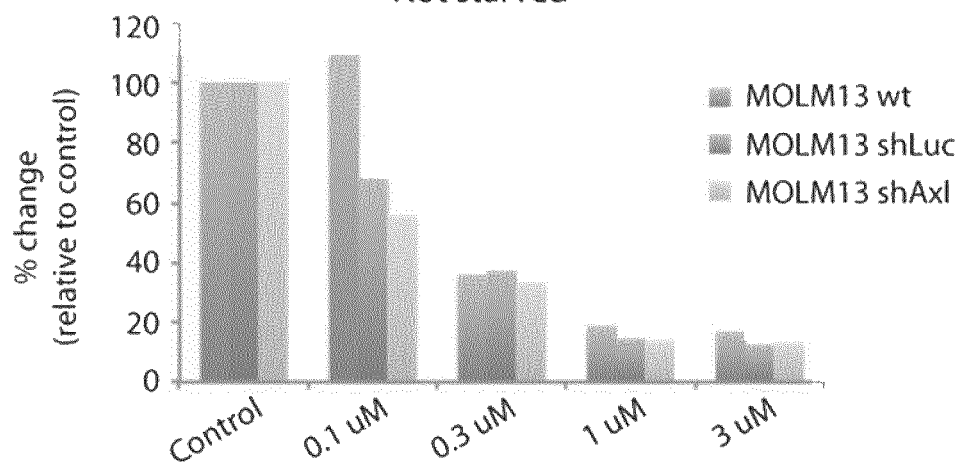
Figure 2C:
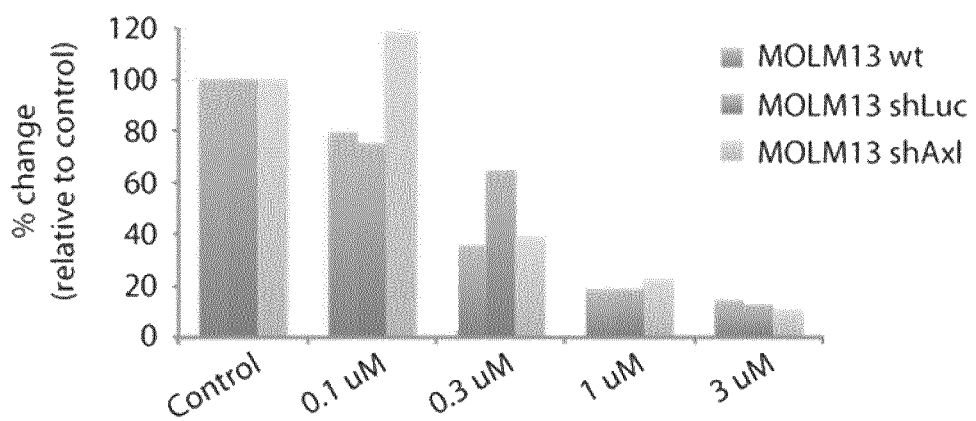

It was found that MOLM13 cells have a high basal phosphorylation level of Akt at the S473 site, and over night starvation did not decrease Akt phosphorylation significantly (FIGS. 1 and 2). Stimulation of the cells with 10% FBS increased the phosphorylation of Akt(S473) slightly. When treated with BGB324, Akt phosphorylation was potently inhibited, both in the presence and absence of 10% FBS (see FIG. 1).

To investigate if pAkt inhibition is caused by a specific inhibition of the Axl kinase, MOLM13 expressing an Axl knockdown construct (shAxl) were treated with BGB324 at different concentrations from 0.1-3 µM. Wt and shLuc-expressing cells were used as controls. In addition, cells that had been starved over night prior to treatment were compared with cells that had been cultured in normal full-serum medium. No significant differences between the response in starved vs. non-starved cells were found. In both experimental conditions, potent dose-dependent reduction of pAkt after BGB324-treatment were found (see FIG. 2).

Surprisingly, inhibition of pAkt was also seen in shAxl-expressing cells, indicating that this inhibition could be an off-target effect rather than a specific response caused by Axl inhibition by BGB324. Thus, Akt inhibition could be caused by an off-target inhibition of a target other than Axl, for example the Flt3 kinase directly. The activation status of Flt3 in these cells after BGB324 treatment was not examined; this needs to be done in order to clarify if there is an off-taget inhibition of Flt3.

Example 2

Evaluation of Phospho-Axl in AML Cells After BGB324-Treatment

When treating with an Axl Tyrosine Kinase inhibitor, a reduction of Axl phosphorylation in the target cells is expected.

MOLM13 cells were used and showed a strong response in pAkt after BGB324-treatment (as assessed by the Mouse-anti-human pAxl (phospho-Axl) antibody Y779 AB (MAB6965) from R&D Systems (BGB #11). These studies were done in parallel with studies looking at pAkt (in the same cells), with the same doses and duration of treatment.

Figure 3:
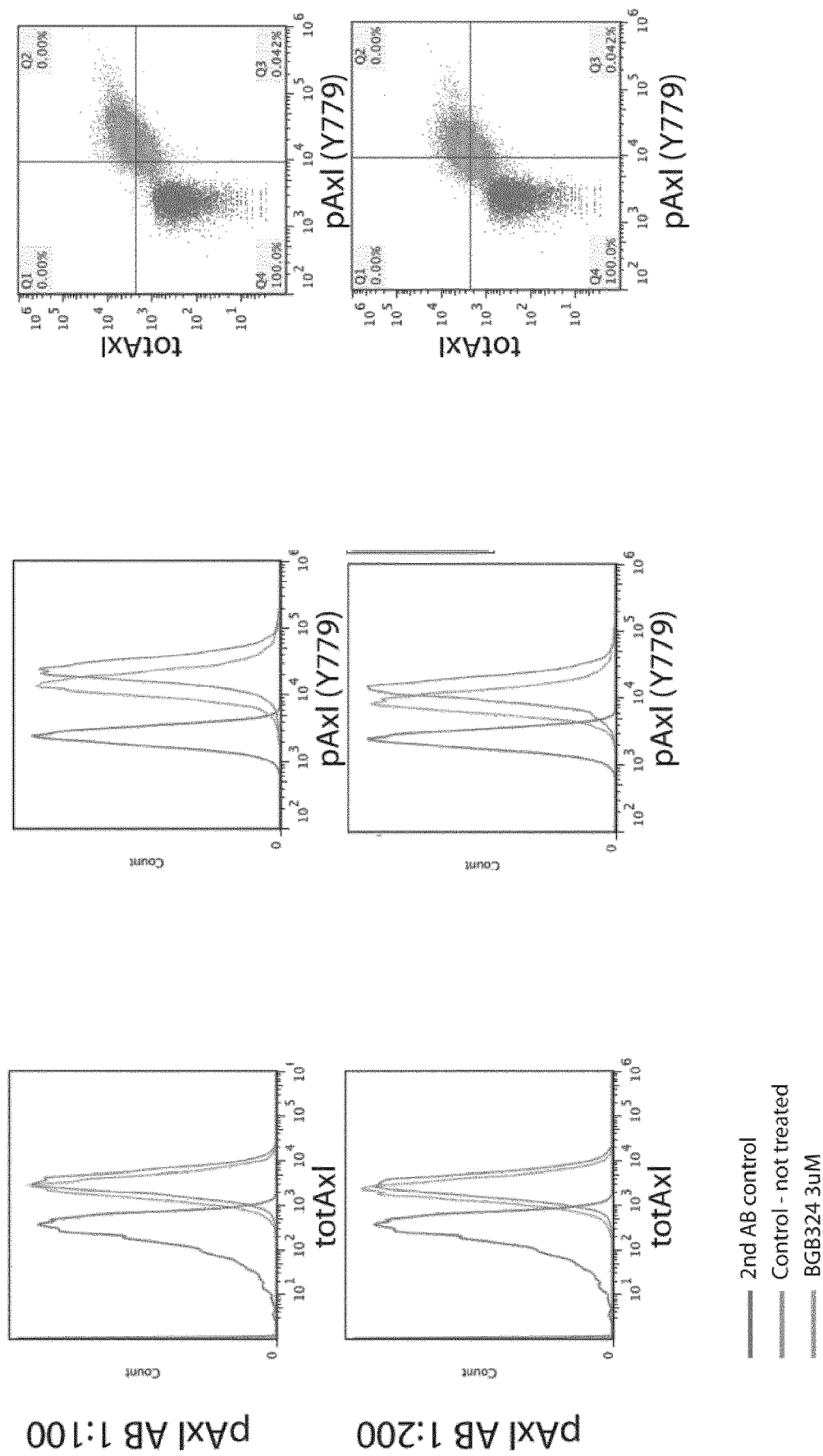
FIG. 3: Assessment of totAxl and pAxl(Y779) in MOLM13 after treatment with 3 μM BGB324 for 40 minutes showed that the total Axl level did not change upon treatment (left panels). However, we found a slight decrease in pAxl (middle panels). The right panels show that the shift seen in pAxl was found in the cells with the highest Axl levels (upper right quadrant).

MOLM13 cells were cultured in starvation medium (RPMI, 0.1% FBS) over night and treated with BGB324 at 3 µM for a total of 40 minutes. (cells were also stimulated with 10% FBS and recombinant human Gas6 (1 µg/ml), but there was no response in pAxl after stimulation, so these data are omitted from the report). Cells were co-stained with pAxl(Y779) and tAxl (1H12) antibodies. We found that MOLM13 cells stained positive for Axl and phospho-Axl. Total Axl expression did not change in the cells after 40 minutes of BGB324-treatment, but we found a modest reduction of pAxl. When gating for Axl-expressing cells, we saw that the reduction of pAxl signal was only seen in Axl-positive cells, showing that the pAxl antibody appears to be Axl-specific (see FIG. 3).

pAxl was further assessed pAxl by, in the same experimental conditions, examining for phosphorylation of Akt (see above, and FIG. 2), comparing starvation with non-starved cells, and using MOLM13 wt, shAxl and shLuc (cells were co-stained with antibodies for both pAkt and pAxl). MOLM13shAxl were used as a negative control, to separate between background binding of the antibodies and the "real" pAxl-signal. In cells that were not starved, only a slight inhibition of pAxl after treatment was found (around 20% at 3 µM BGB324 dose).

Figure 4A:
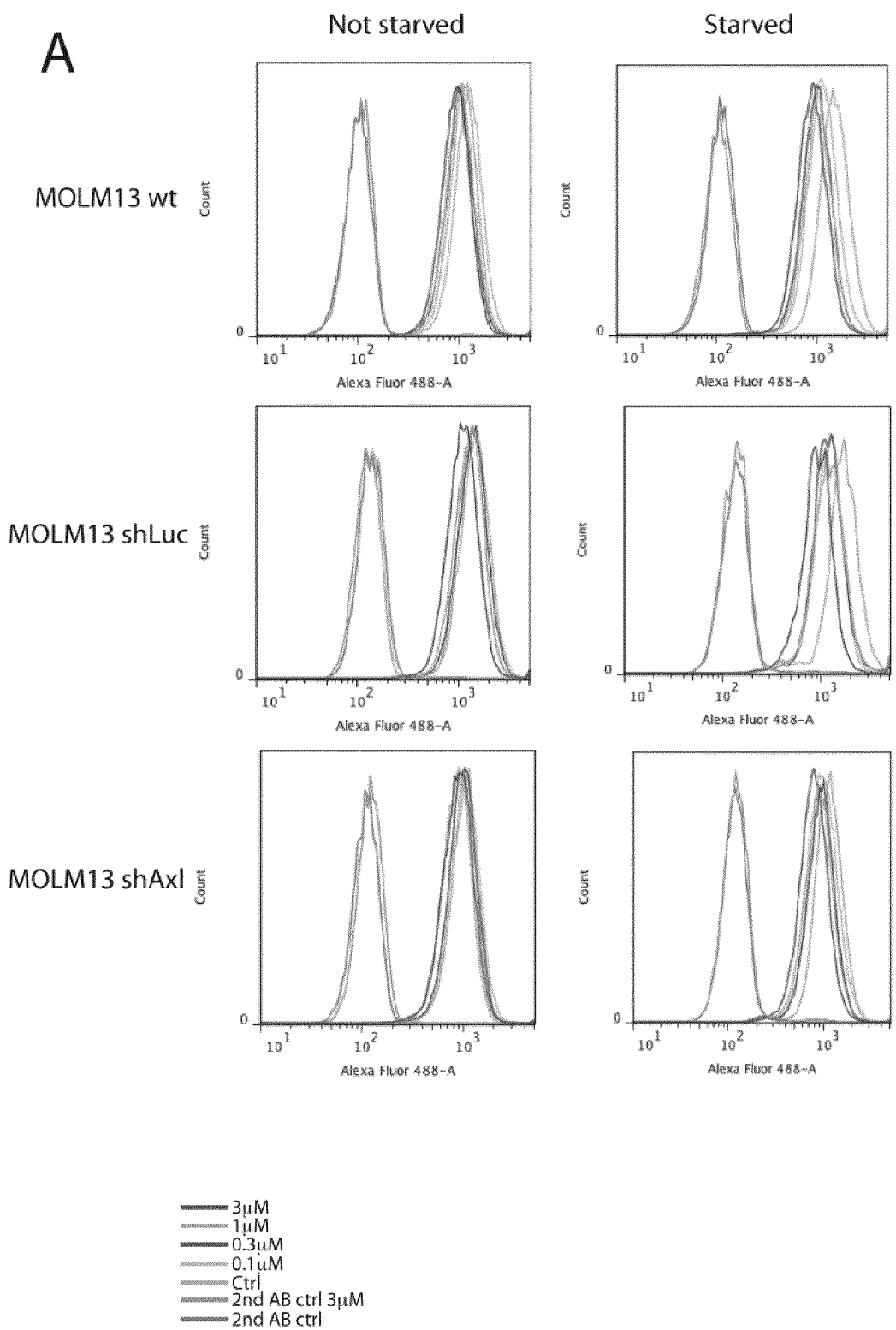
FIG. 4: Histograms showing pAxl(Y779) dose-response of BGB324 in MOLM13 wt, shLuc and shAxl. Starved cells are compared to non-starved cells (A). The geometrig mean of fluorescence was also quantified in non-starved (B) and starved (C) cells. The graphs show % change relative to control (set to 100%).

The response in shAxl cells was the same as in wt and shLuc cells, indicating that the change seen here is not inhibition of Axl phosphorylation, but an unspecific binding of the antibody (FIGS. 4A and B). However, in pre-starved cells, a stronger inhibition after treatment was found. ShAxl cells were still inhibited approximately 20% at 3 µM, but wt and shLuc cells had an additional 20% inhibition (40% total reduction), indicating that phosphorylation of Axl might indeed be inhibited in these cells (FIGS. 4A and C).

Titration of the pAxl(Y779) Antibody

Figures 4B, 4C:
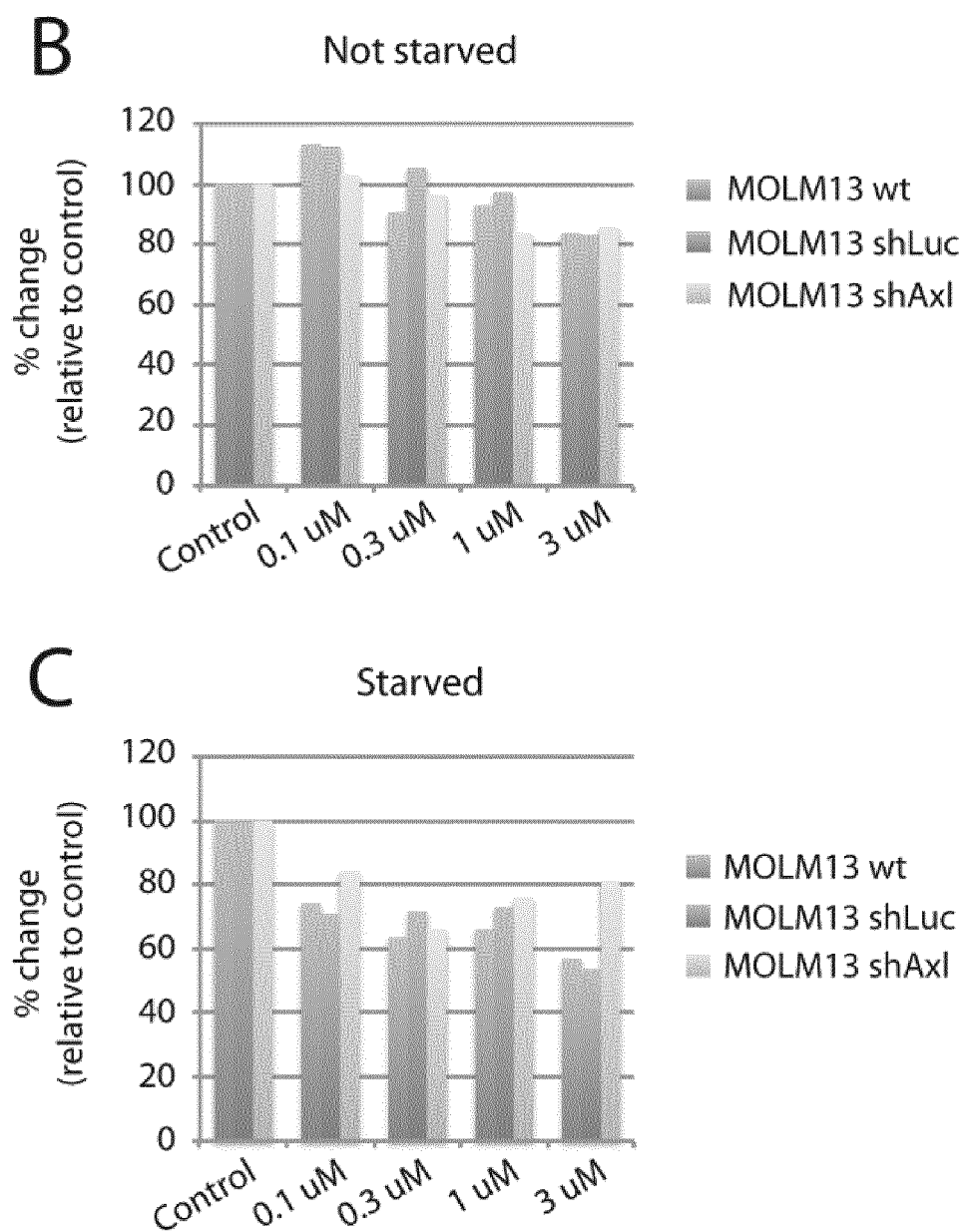
Figure 5A:
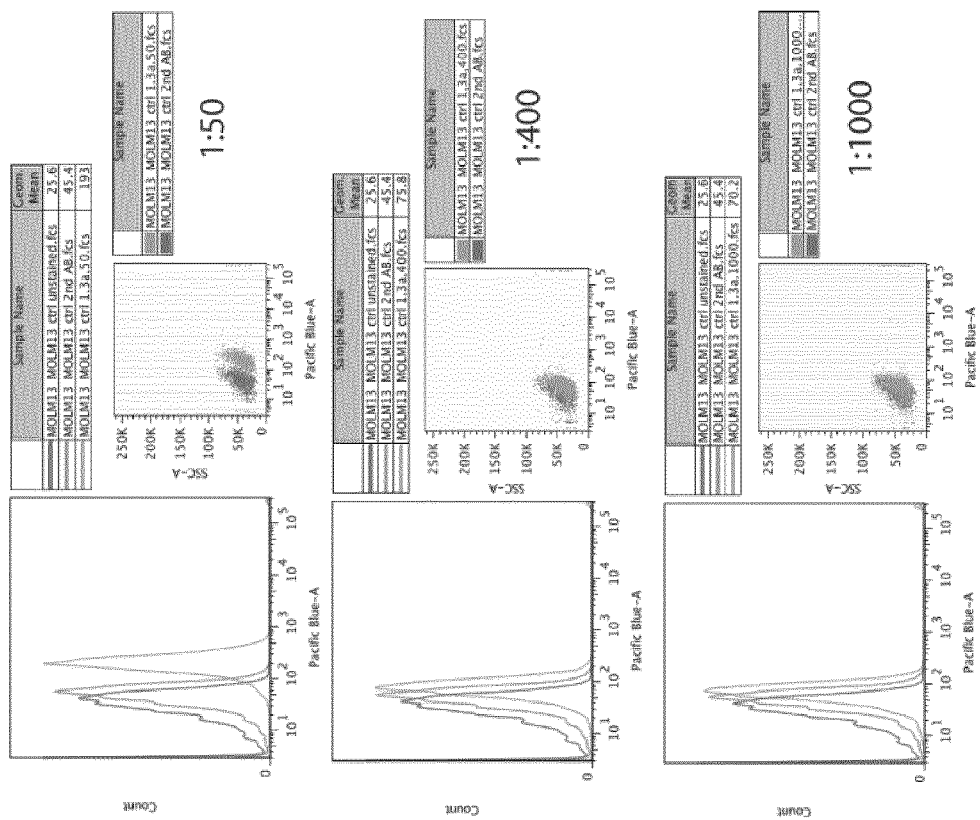
FIG. 5: Titration of pAxl AB for flow cytometric evaluation at dilutions 1:50-1:3000. Phosphatase-treated cells were included as baseline controls. Representative histograms are included for three dilutions (A). Geometric mean (B) and signal-to-noise ratio (C) was compared in phosphatase- vs non-phosphatase treated cells at all dilutions.
Figure 5A:
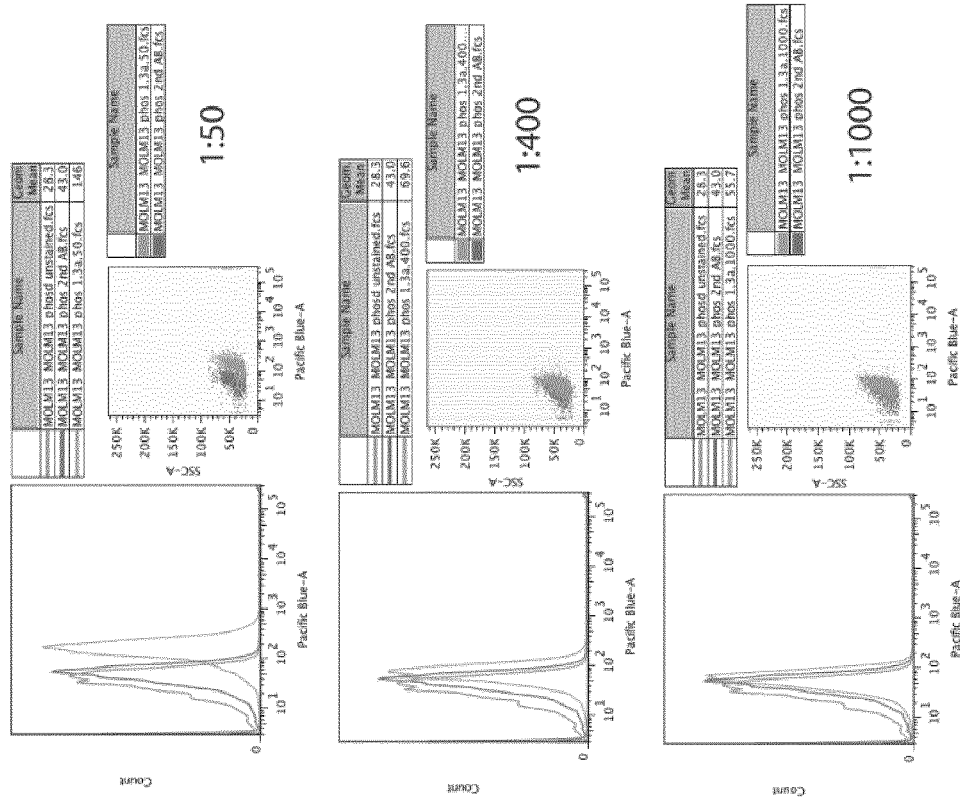
Figure 5B:
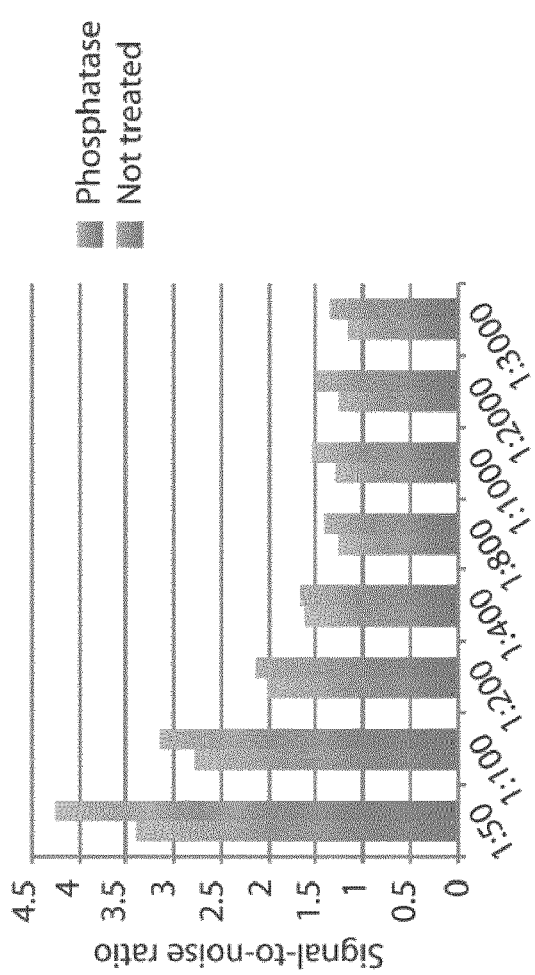
Figure 5C:
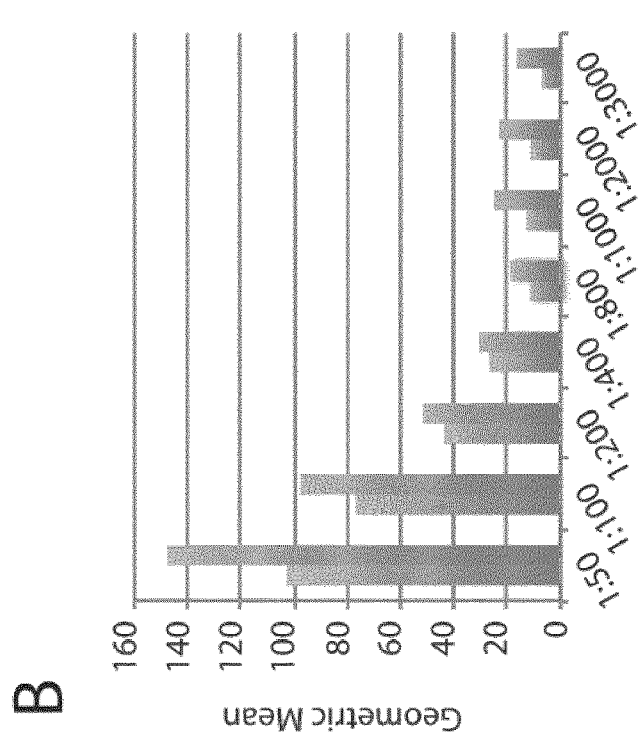

As seen in FIG. 4, the pAxl antibody has a high background binding in MOLM13 shAxl cells. Therefore, the antibody was titrated in MOLM13 wt cells, at dilutions from 1:50 to 1:3000 (FIG. 5). The cells were phosphatase-treated, to separate the background binding from the "real" pAxl-signal. It was found that the background-binding was high in phosphatase-treated cells, but these cells stained more or less negative at 1:400 dilution of the pAxl antibody. At this antibody dilution, only a slight pAxl signal is seen in non-phosphatase treated cells. This could be due to low levels of phosphorylated Axl in the MOLM13 cells.

The signal-to-noise ratio is at 1.5. To increase the signal slightly, it is recommended to use a slightly lower dilution, at 1:200, but to include a phosphatase-treated control to subtract background binding. If phosphatase-treated control cells are not included, an antibody-dilution of 1:400 is recommended.

Example 3

Axl Expression in Human Blood Samples

During an AML clinical trial, blood samples will be collected from patients at different time points. Analyses of drug efficacy will be done in patient blood samples collected before- and after treatment, looking at a large panel of phospho-proteins as well as the total protein level of a few selected biomarker-candidates. Therefore, blood samples from healthy volunteers were examined by flow cytometry, in order to evaluate the staining procedures as well as the expression levels of potential biomarkers in normal healthy blood.

Evaluation of the Axl expression level in blood samples could be important in patient stratification in the clinical trial, as a high Axl level in the blood of AML patients has been shown to correlate to susceptibility to Axl inhibition by BGB324 (Ben-Batalla et al., 2013). Therefore, it was decided to examine whether Axl could also be detected in normal blood samples from healthy subjects.

Figure 6A:
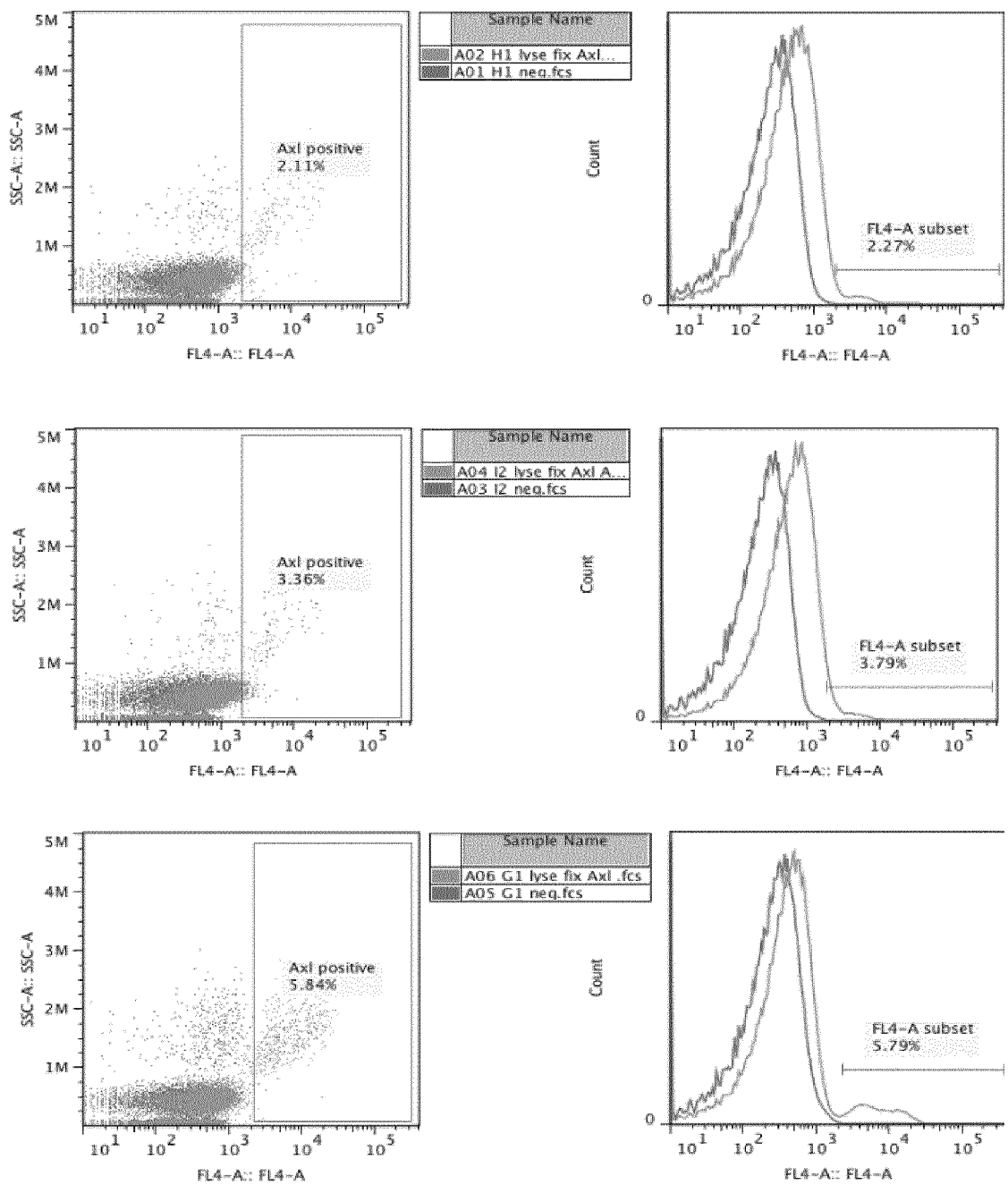
FIG. 6: Expression of Axl in normal blood samples collected from 6 healthy volunteers shows that there are detectable levels of Axl, although in small quantities. The percentage of Axl-positive cells varies from around 2-6%, with some individual variation. The red cells in the small scatterplots on the far right are Axl positive cells, and the upper plots show that Axl might be expressed on several different types of white blood cells.
Figure 6B:
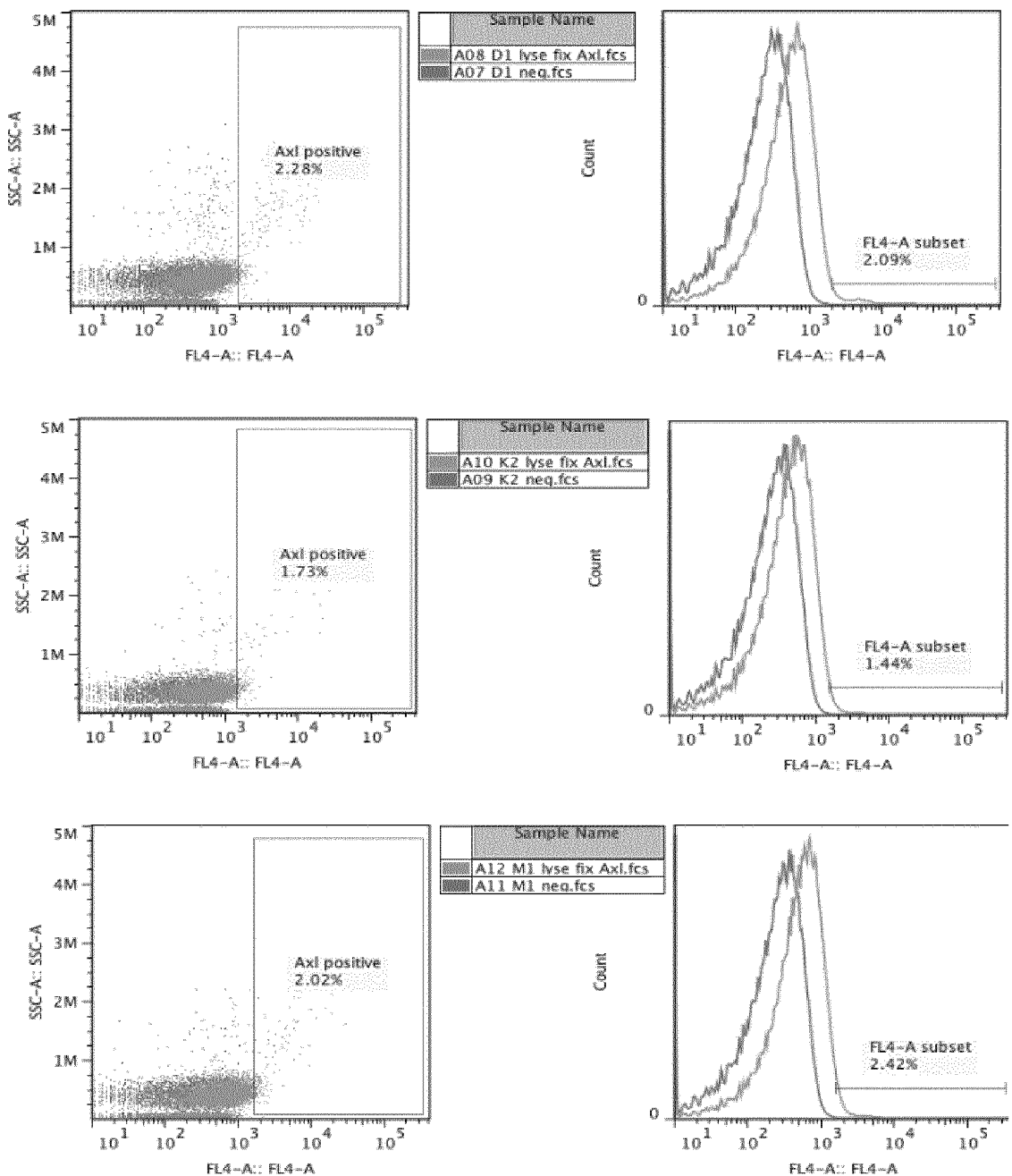

Blood was collected from 6 healthy volunteers in sodium citrate vacutainers. The blood was fixed and PBMCs were prepared for flow and stained with 1H12-A647-conjugate (1.2 mg/ml diluted 1:3000 in PBS 0.5% BSA). Low, but detectable, levels of Axl were found in all blood samples, although the Axl levels seems to vary between individuals (figure x). The Axl-level was highest in subject "G" (FIG. 6, panel 3 from the top), which reported having a cold on the day of blood sampling. This could indicate that Axl may be expressed specifically on immune cells that are upregulated as a response to bacterial- or virus-infection. However, back-gating of the Axl positive cells onto the general population reveals staining in multiple populations distinguishable by their FSC/SSC properties in all subjects. Detailed assignment to different cell types will require co-staining with multiple CD markers.

The phosphorylation levels of Axl(Y779) and Akt(S473) in blood samples from two healthy volunteers was also examined.

In a first experiment samples were stained without permebealization (data not included). The pAxl (but not the pAkt) antibody gave a strong signal in these samples, indicating that the pAxl AB has a high background binding to the outside surface of the cell at the dilution recommended by the manufacturer (staining non-permeabilised cells should result in no binding of either antibody to the cells, as they both bind to intracellular epitopes).

To minimize the background, the antibodies should ideally be titrated in blood samples. However, in the absence of sufficient blood samples to perform titrations, samples can be phosphatase-treated after fixation and permebealization, to remove all phosphate groups and thereby identify the baseline/background binding of the phospho-antibodies (so as to distinguish the background-signal from the real phospho-signal).

Blood samples from BGB324-treated individuals were not available, so BGB324-treatment was simulated by incubating fresh unfixed blood samples with 1 μM BGB324 for 30 minutes before fixation. Thereafter, samples were fixed, permebealized, and stained for flow with pAxl and pAkt antibodies to examine whether we could see a response to BGB324-treatment in these biomarkers (see FIG. 7). Phosphatase-treated cells were included as a negative staining control.

Figure 7:
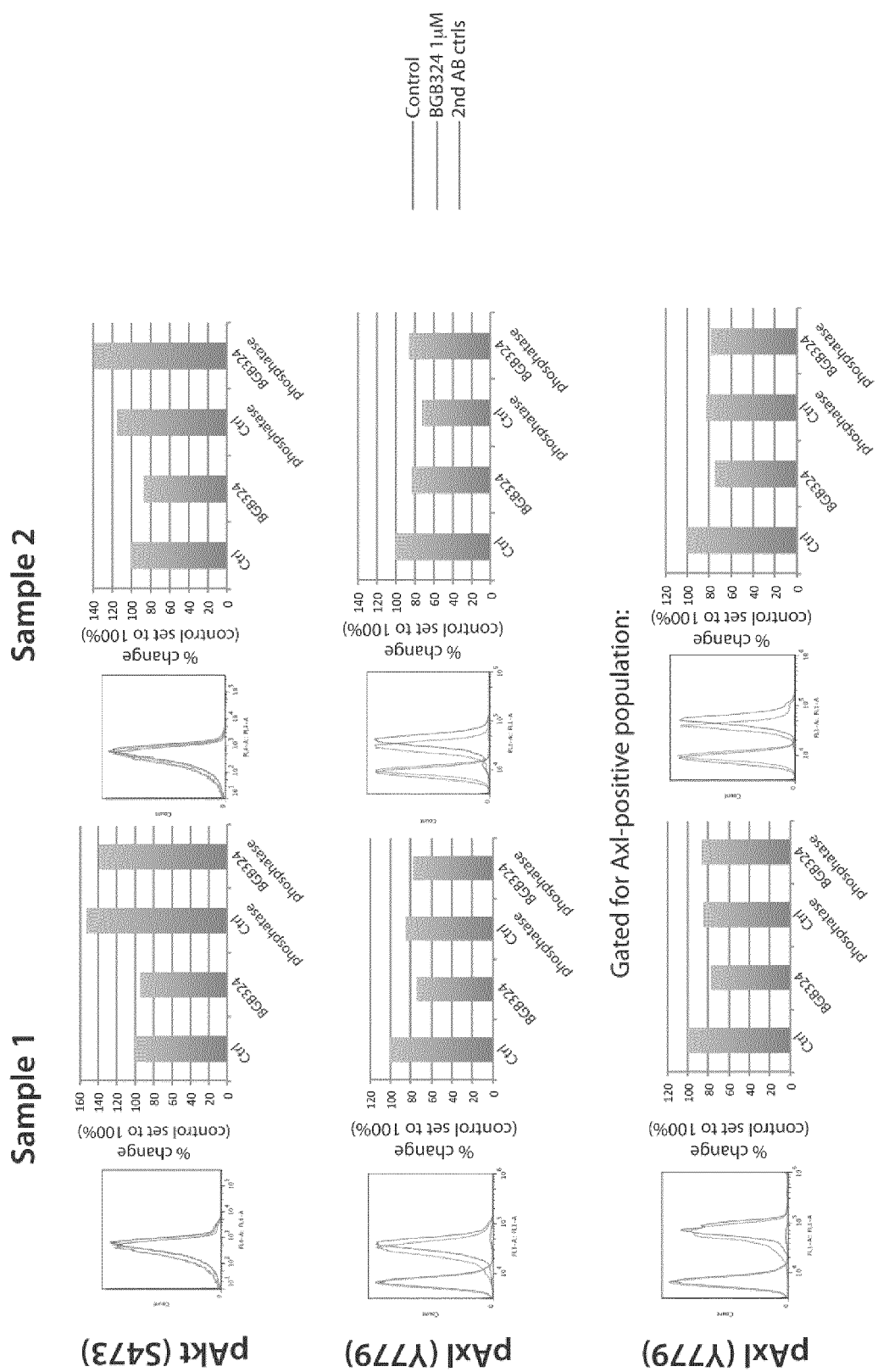
FIG. 7: Blood samples from two individual healthy volunteers were treated with BGB324 at 1 μM ex vivo for 30 minutes, and phosphorylation of Akt(S473) (upper panels) and Axl(Y779) (middle panels) was assessed by flow cytometry. The samples were also stained for total Axl expression, and the phosphorylation of Axl was assessed in these cells only to evaluate background binding of the pAxl antibody (lower panels). Graphs show quantification of geometric mean of fluorescence, calculated as % change relative to control (set to 100%).

There was close to no expression of phosphorylated Akt in live cells (PBMCs) from the blood samples (as compared to the secondary AB controls/background fluorescence). The signal was only slightly higher than the background (FIG. 7, upper panels). After substracting the background signal the geometric mean of each sample was quantified and the control sample was set to 100%. The quantification showed a very slight reduction in pAkt after BGB324-treatment in both samples, but the phosphatase-treated samples had an even higher signal than the controls. Therefore, it is likely that the inhibition can be disregarded as false due to the very low signal. It is therefore concluded that pAkt is undetectable in normal blood samples.

When looking at the pAxl signal in the whole live cell population, it was found that pAxl is reduced around 20% after BGB324-treatment in both samples (as compared to the control; see FIG. 7, middle panels). The phosphatase-treated controls gave approximately the same signal as the BGB324-treated sample, indicating that pAxl is close to fully inhibited in these cells, assuming that phosphatase-treatment removes all phosphorylation of signaling proteins.

Due to the background binding-issue with the pAxl AB, the samples were also co-stained with total-Axl AB (1H12-A647 conjugate) in order to evaluate whether there was a difference between the pAxl-signal in Axl-positive cells versus the whole live cell population. When gated for Axl-positive cells (around 5% of the total live cell population), an ~20% reduction of pAxl(Y779) was found in both samples, and a comparably low signal from phosphatase-treated samples (see FIG. 7, lower panels). Thus, it is concluded that Axl phosphorylation in PBMCs isolated from healthy volunteers appears to be inhibited by in vitro treatment of the blood with BGB324.

No blood samples from patients with AML were available: although the phosphorylation-levels of Akt and Axl and the level of total Axl may be low in normal blood, this is likely to look very different in AML patient samples (such as in AML cells carrying the ITD Flt3 mutation). As such, clinical testing of these markers in patient samples is planned.

Example 4

Screening of Selected Biomarkers in a Panel of AML Cell Lines

AML is a highly heterogenous clonal disorder. Accordingly, although a strong response of biomarkers such as pAkt(S473) is seen in the MOLM13 cell line after BGB324-treatment, it is not known if this response will be universal in the diverse spectrum of AML patients.

The diversity of AML cells and their responses was investigated using a panel of AML cell lines and assessing their responses after BGB324-treatment. The cells were selected based on $IC_{50}$ values of BGB324 (determined by resazurin assay), and include MOLM13 & Mv4-11 (considered to be responders, with an IC50 of 0.45 μM and 0.14 μM, respectively) and Kasumi & OCI-M1 (considered to be non-responders, with an $IC_{50}$ of 1.2 μM and 1.8 μM, respectively). Downstream phospho-markers were examined after short term treatment (1 hour); total protein expression of downstream markers was examined after long term treatment (24-72 hours).

When investigating phospho-markers, the cells were starved overnight in the appropriate growth medium containing 0.1% FBS, pre-treated with BGB324 at 0.5 and 1 μM for one hour, and stimulated with 10% FBS for 20 minutes (to induce phosphorylation, with BGB324 present). Cells were then fixed and stained for flow cytometric analyses.

Long-term treatment was done in complete medium, without starvation. The responders were treated with 0.05, 0.1 or 0.3 μM BGB324, whereas the non-responders were treated with only a single dose of 2.5 μM BGB324. The cells were fixed after 24, 48 or 72 hours, and the samples were stored in 90% MeOH at −20° C. until all samples were harvested, and stained for flow at the same time.

pAkt (S473) in the AML Panel

As previously mentioned, Akt signaling is linked directly to Axl signaling, as well as to Flt3, which is an important disease driver in AML. Therefore, the Akt signaling pattern was investigated in the AML panel before and after BGB324-treatment. Akt was only examined in short term treated cells. Total Akt was not assessed.

Figure 8:
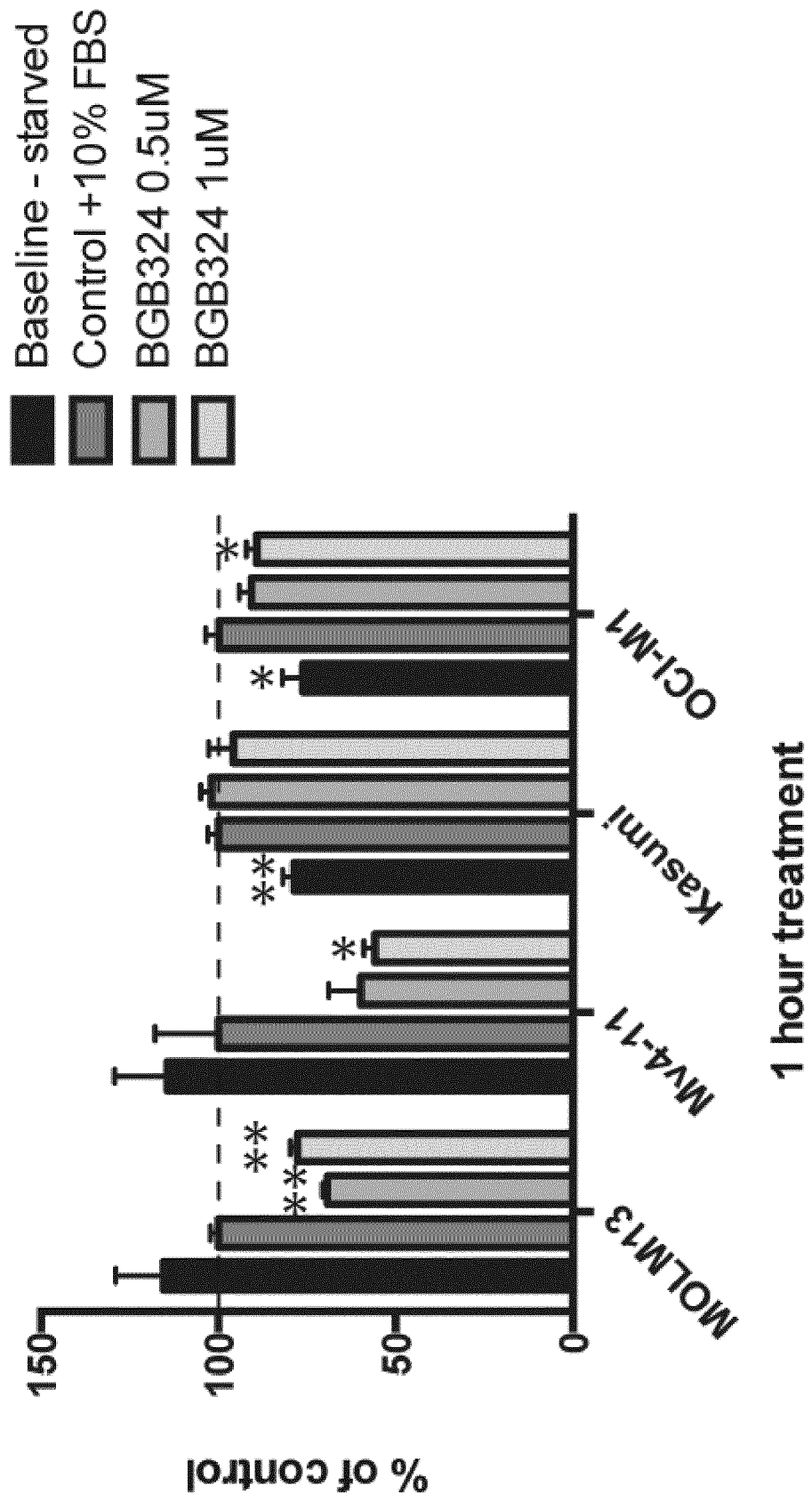
FIG. 8: Response in pAkt(S473) in AML cells after 1 hour BGB324-treatment at the indicated doses. The graph shows geometric mean of fluorescence, calculated as % of control (10% FBS stimulation, which is set to 100%—indicated with a dotted line), ±SEM. * indicates significance relative to control, calculated using a two-tailed Student's t-test. *$p<0.05$, **$p<0.005$, n=3.

It was found that BGB324 inhibits Akt phosphorylation at 0.5 and 1 μM concentration in MOLM13 and Mv4-11 (although the inhibition is not significant at 0.5 μM in Mv4-11 due to a large standard deviation in the control group) (see FIG. 8). In Kasumi and OCI-M1, BGB324 had close to no effect, although there was a slight and significant inhibition of pAkt in OCI-M1 cells at 1 μM concentration. It should also be noted that starvation lead to increased Akt phosphorylation in MOLM13 and Mv4-11, whereas in Kasumi and OCI-M1 starvation lead to decreased phosphorylation. Consequently, FBS-stimulation reduced Akt phosphorylation in MOLM13 and Mv4-11, whereas pAkt was stimulated by FBS in Kasumi and OCI-M1. The reasons for these differences between the cell types is presently unclear.

Axl in the AML Panel

To investigate the direct effect of BGB324-treatment on Axl signaling, the phosphorylation of Axl after short term treatment was examined, as well as the total protein expression of Axl after long-term treatment in the AML panel.

The expression of Axl is generally low in AML cells (compared to adherent cells), and is also variable among the AML cells examined. The cells with high $IC_{50}$ of BGB324 generally have quite low Axl expression, as determined by western blot (see FIG. 3).

Figure 9:
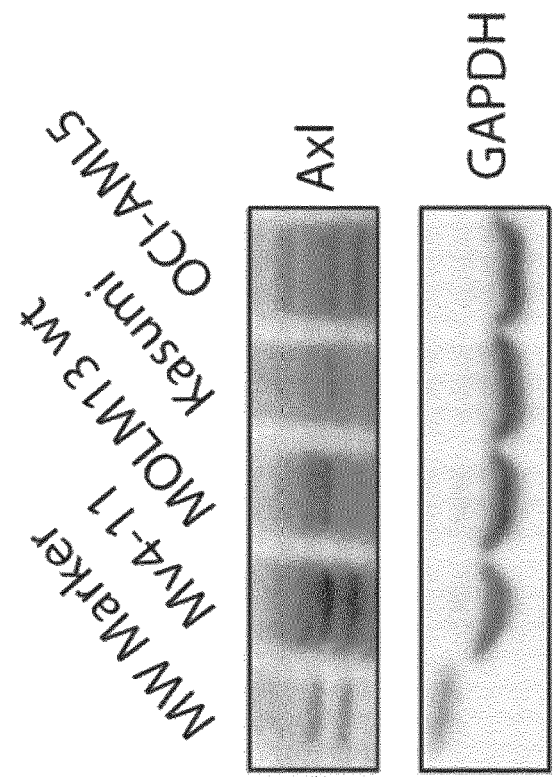
FIG. 9: Axl expression in Mv4-11, MOLM13, Kasumi and OCI-AML 5 cells shown by western blot. Two individual western blots were included to illustrate the variable Axl expression seen in AML cells.
Figure 9:
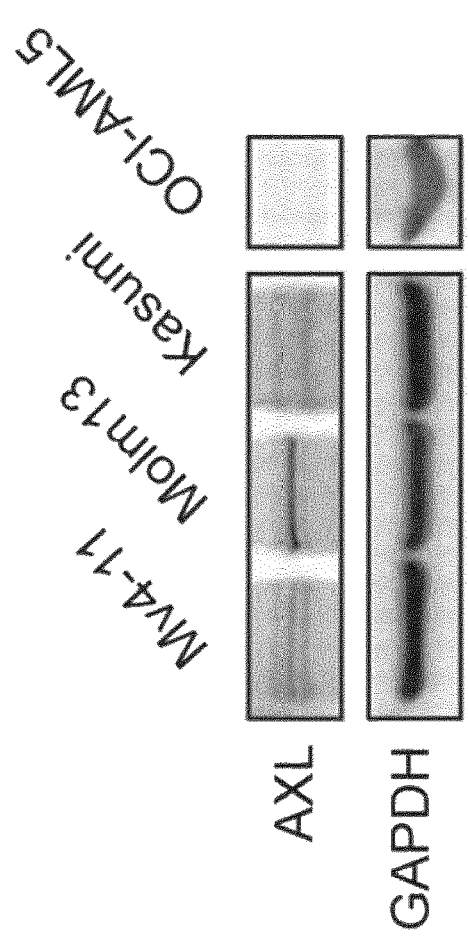

MOLM13 appear to have the highest Axl expression. Although Mv4-11 cells are considered responders and have a relatively low $IC_{50}$, they still appear to express low levels of Axl. However, the non-responder Kasumi cells have an even lower expression. OCI-AML5 cells appear, in the left blot, to have no Axl, but on the blot to the right they appear to have low but detectable levels of Axl (see FIG. 9). This correlates well with the high $IC_{50}$ of these cells.

Figure 10:
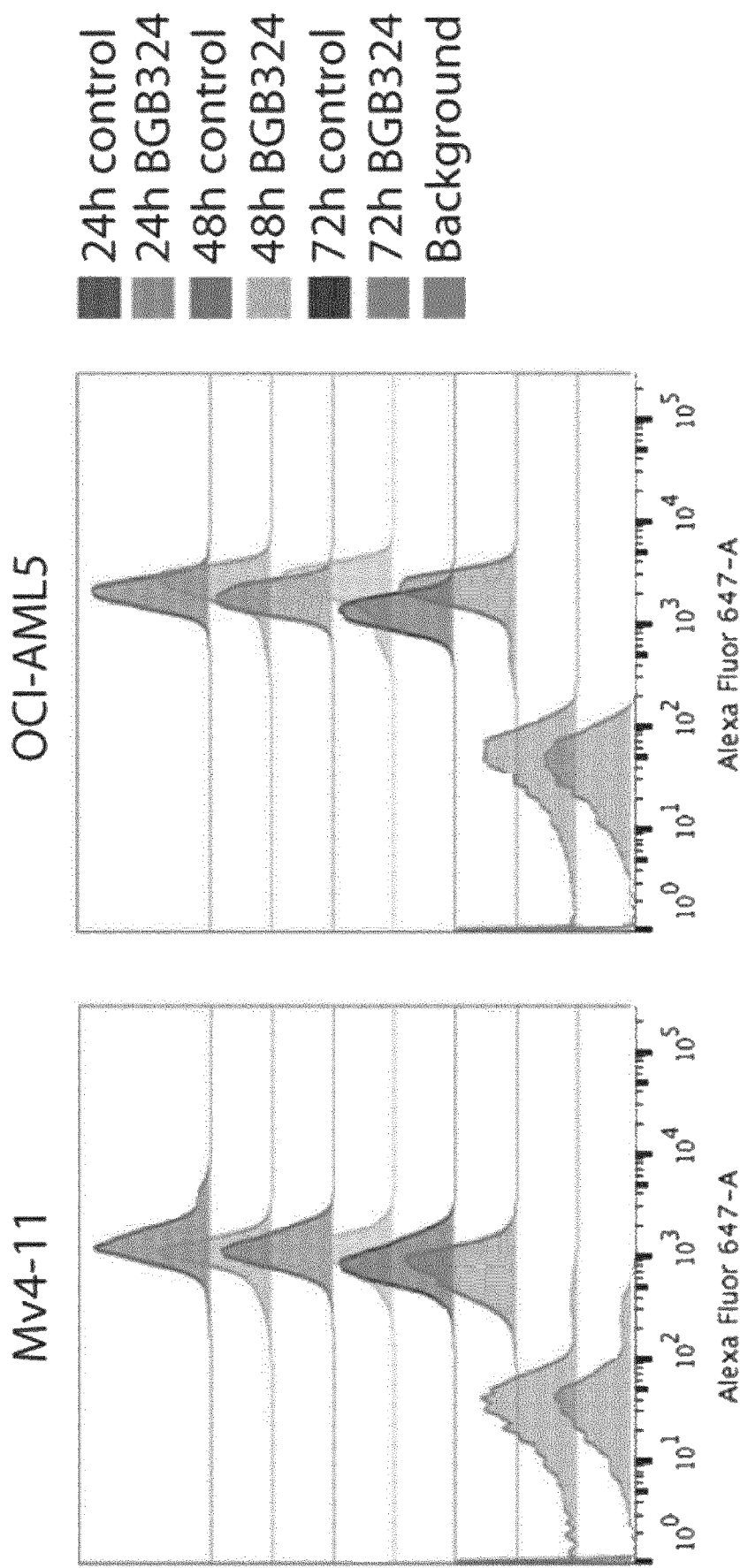
FIG. 10: Axl expression in Mv4-11 and OCI-AML cells on flow, before and after treatment with 0.3 μM (Mv4-11) or 2.5 μM (OCI-AML5) BGB324 for 24, 48 or 72 hours. The cells are stained with 1H12-A647 pre-conjugated antibody, and background illustrates spontaneous background fluorescence in unstained cells.
Figure 10A:
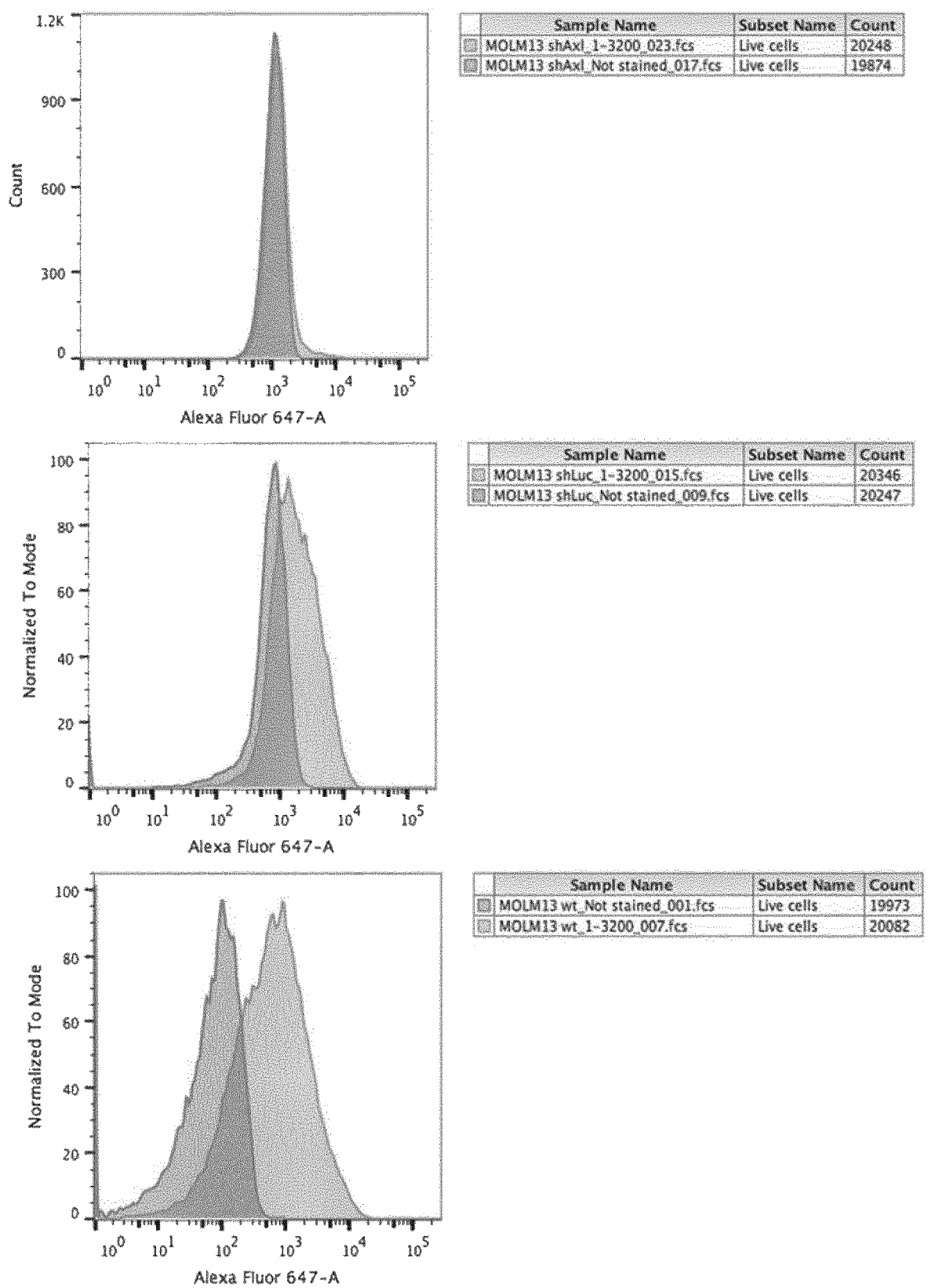
FIG. 10A: MOLM13 cells expressing shAxl (upper panel), shLuc (middle panel) and MOLM13 wt cells (lower panel) were stained with Axl-1H12-A647 antibody, and analysed by flow cytometry. Red histograms are signal from unstained cells (background), whereas blue histograms are signal from 1H12-A647-stained cells. There is minimal background binding of the 1H12 antibody in shAxl-expressing cells.

Axl expression in AML cells (by western blot) was noted to be variable in OCI-AML5 cells and also in Mv4-11: the cells can appear Axl-negative on one blot, and positive on the next. However, when OCI-AML5 and Mv4-11 cells were stained with anti-Axl 1H12 antibody for flow, a clear positive signal was seen (se FIG. 10). This could be due to unspecific binding of the antibody, but this seems unlikely since the 1H12 antibody has been titrated in Axl-expressing MOLM13 wt cells and MOLM13 cells expressing an Axl knockdown construct (shAxl) and displays virtually no unspecific binding in MOLM13shAxl, even at very high concentrations (see FIG. 10A).

Figure 11:
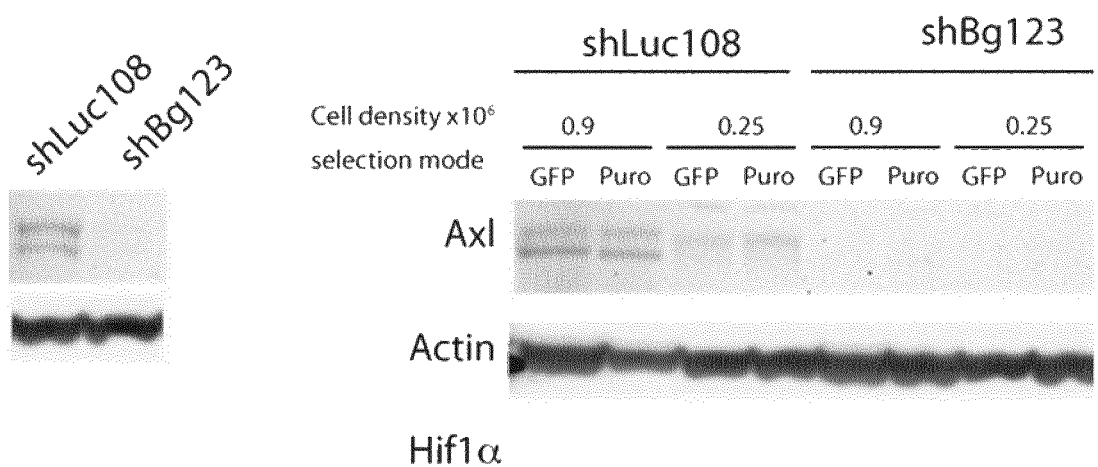
FIG. 11: MOLM13 and Mv4-11 cells were grown at low (0.25×106) or high (0.9×106) density, and Axl expression was examined by western blot. Normal cells expressing a control construct (shLuc108) were compared to cells espressing an Axl knockout construct (shBg123). In both MOLM13 and Mv4-11, we found that Axl is upregulated at high cell density.
Figure 11:
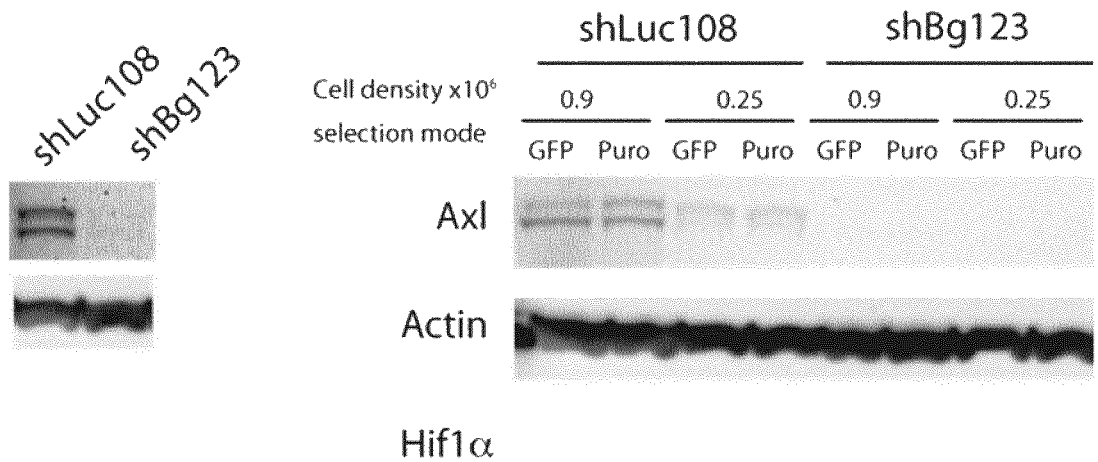

Axl is a receptor located in the cell membrane, and the variability of Axl expression in the same cell lines seen on western blot might be an artifact caused by insufficient lysis of the cells (insoluble membrane debris is cleared from the lysate by centrifugation before further processing). However, an alternative explanation could be an upregulation of Axl expression under certain growth conditions. It has been seen in previous experiments that suspension cells (MOLM13 and Mv4-11) will upregulate Axl significantly in harsh culture conditions, such as at very high cell density and/or in hypoxic or acidic growth conditions (see FIG. 11). Interestingly, this does not happen in adherent cells (pers. comm., Magnus Blø). Thus, it could be possible that even though OCI-AML5 cells appear to have no Axl expression in the western blot in FIG. 9, the culture conditions in the flow-experiment could have been such that Axl was expressed in these cells. However, more experiments are necessary to determine this.

Figure 12:
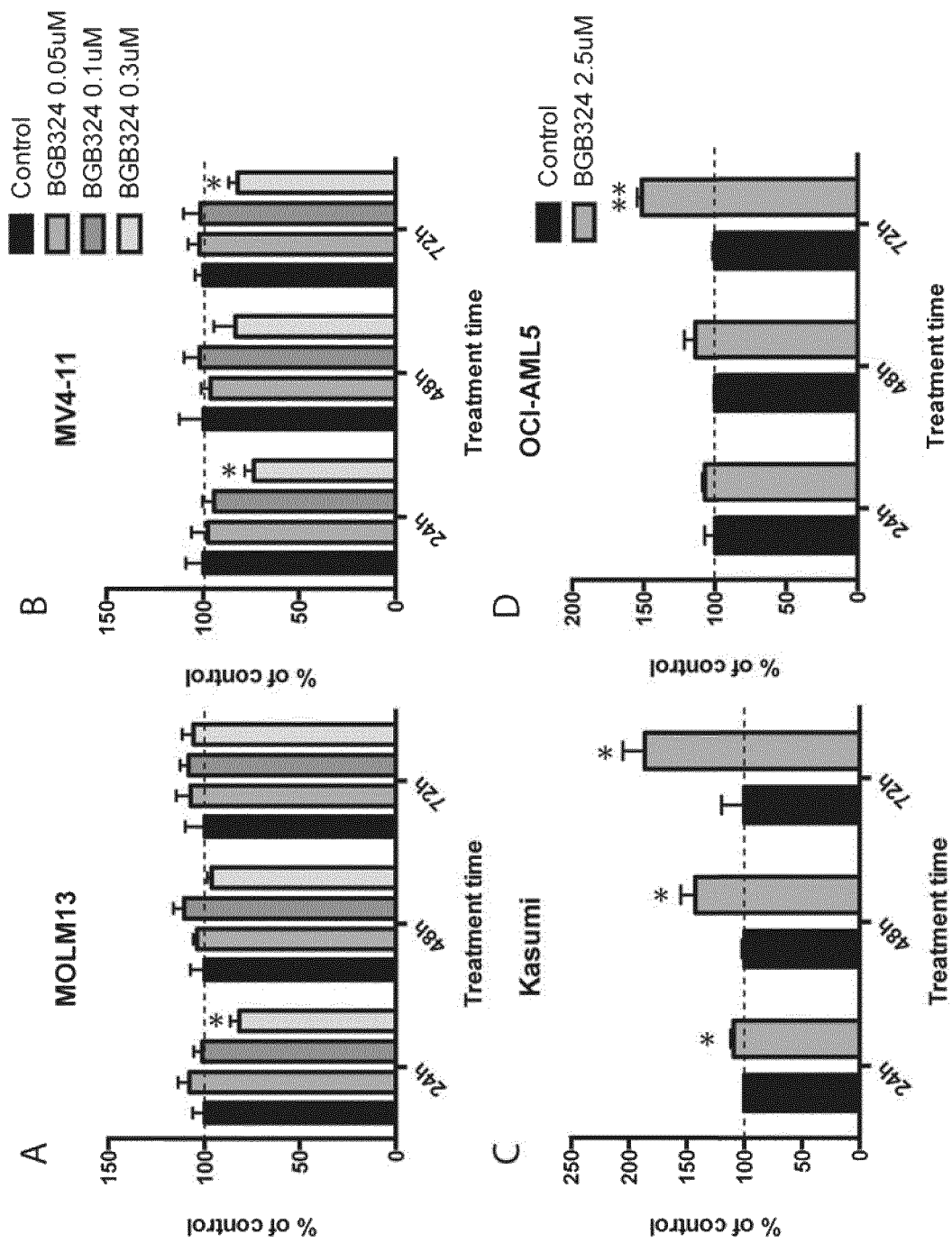
FIG. 12: Response in totAxl in AML cell lines after 24, 48 and 72 hours of treatment with BGB324 at 0.05, 0.1 or 0.3 μM (MOLM13 and Mv4-11, upper panels) or at 2.5 μM (Kasumi and OCI-AML5, lower panels). The graphs show geometric mean of fluorescence, calculated as % of control (which is set to 100%—indicated by a dotted line), ±SEM. * indicates significance relative to control, calculated using a two-tailed Student's t-test. *$p<0.05$, **$p<0.005$, n=3.

When examining the selected cell lines for Axl expression before and after treatment with BGB324 for 24, 48 and 72 hours (see FIG. 12), it was found that the Axl expression in Mv4-11 and MOLM13 was relatively stable. A slight and significant reduction of Axl was seen in both MOLM13 and Mv4-11 at the highest treatment dose (0.3 µM) at 24 hours, and in Mv4-11 also at 72 hours. Interestingly, Kasumi and OCI-AML5 cells responds oppositely to MOLM13 and Mv4-11. Axl expression in both these cell lines goes significantly up with treatment.

Figure 13:
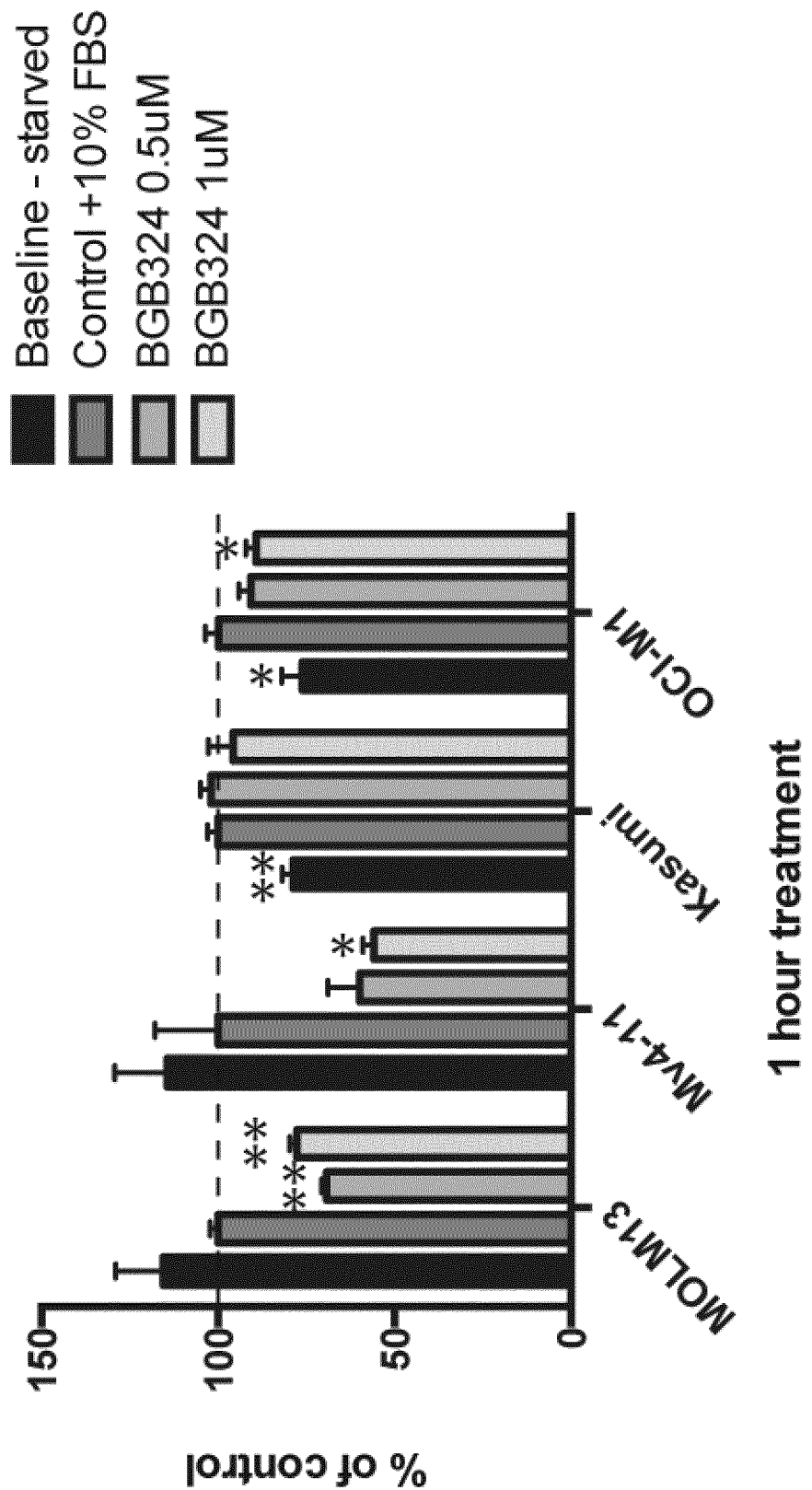
FIG. 13: Response in pAxl in AML cells after after 1 hour BGB324-treatment at the indicated doses. The graph shows geometric mean of fluorescence, calculated as % of control (10% FBS stimulation, which is set to 100%—indicated with a dotted line), ±SEM. * indicates significance relative to control, calculated using a two-tailed Student's t-test. *$p<0.05$, **$p<0.005$, n=3.

When examining the phosphorylation of Axl in the AML panel before and after BGB324-treatment (1 hour, 0.5 and 1 µM BGB324) it was found that the phosphorylation of Axl at Y779 is significantly reduced in MOLM13 and Mv4-11 whereas, in the non-responders, only OCI-M1 show a slight (but significant) reduction of pAxl at the highest treatment dose. Kasumi cells show no response to treatment (see FIG. 13). It should also be noted that starvation appears to induce pAxl in MOLM13 and Mv4-11, whereas the opposite is seen in Kasumi and OCI-M1. This is the same pattern seen in pAkt in the same cells (see FIG. 8).

Erk in the AML Panel

Both phosphorylation and total protein expression of Erk was investigated, after short- and long-term treatment, respectively.

Figure 14:
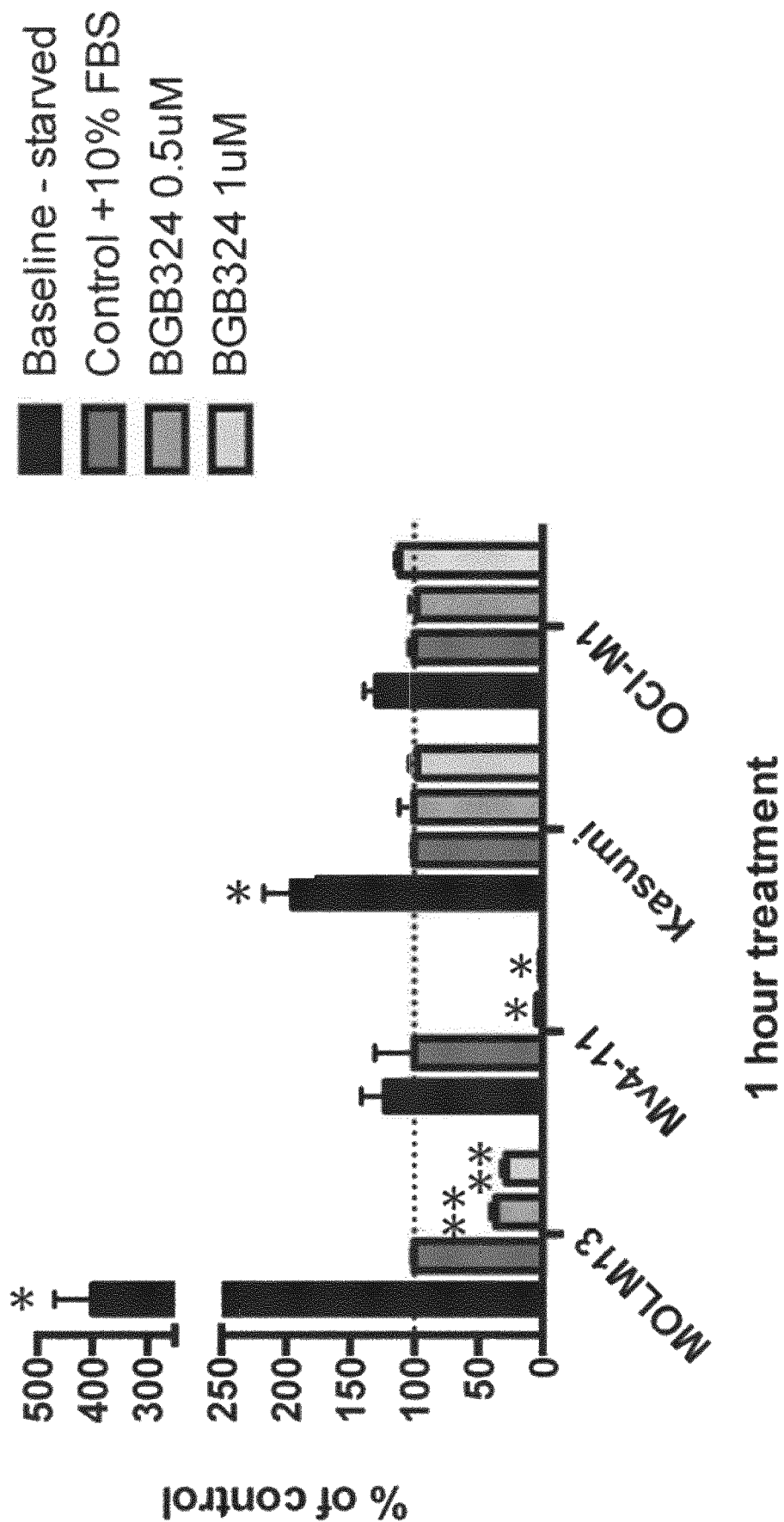
FIG. 14: Response in pErk in AML cells after after 1 hour BGB324-treatment at the indicated doses. The graph shows geometric mean of fluorescence, calculated as % of control (10% FBS stimulation, which is set to 100%—indicated with a dotted line), ±SEM. * indicates significance relative to control, calculated using a two-tailed Student's t-test. *$p<0.05$, **$p<0.005$, n=3.

When examining phosphorylation of Erk, a strong and significant reduction in the 'responder cells', MOLM13 and Mv4-11, was found at all treatment doses. In the 'non-resonders', Kasumi and OCI-M1, there was no significant differences in pErk after treatment with BGB324 (FIG. 14). It should be noted that overnight starvation strongly induces phosphorylation of Erk in MOLM13 and Kasumi, but not in Mv4-11 and OCI-M1 cells.

Figure 15:
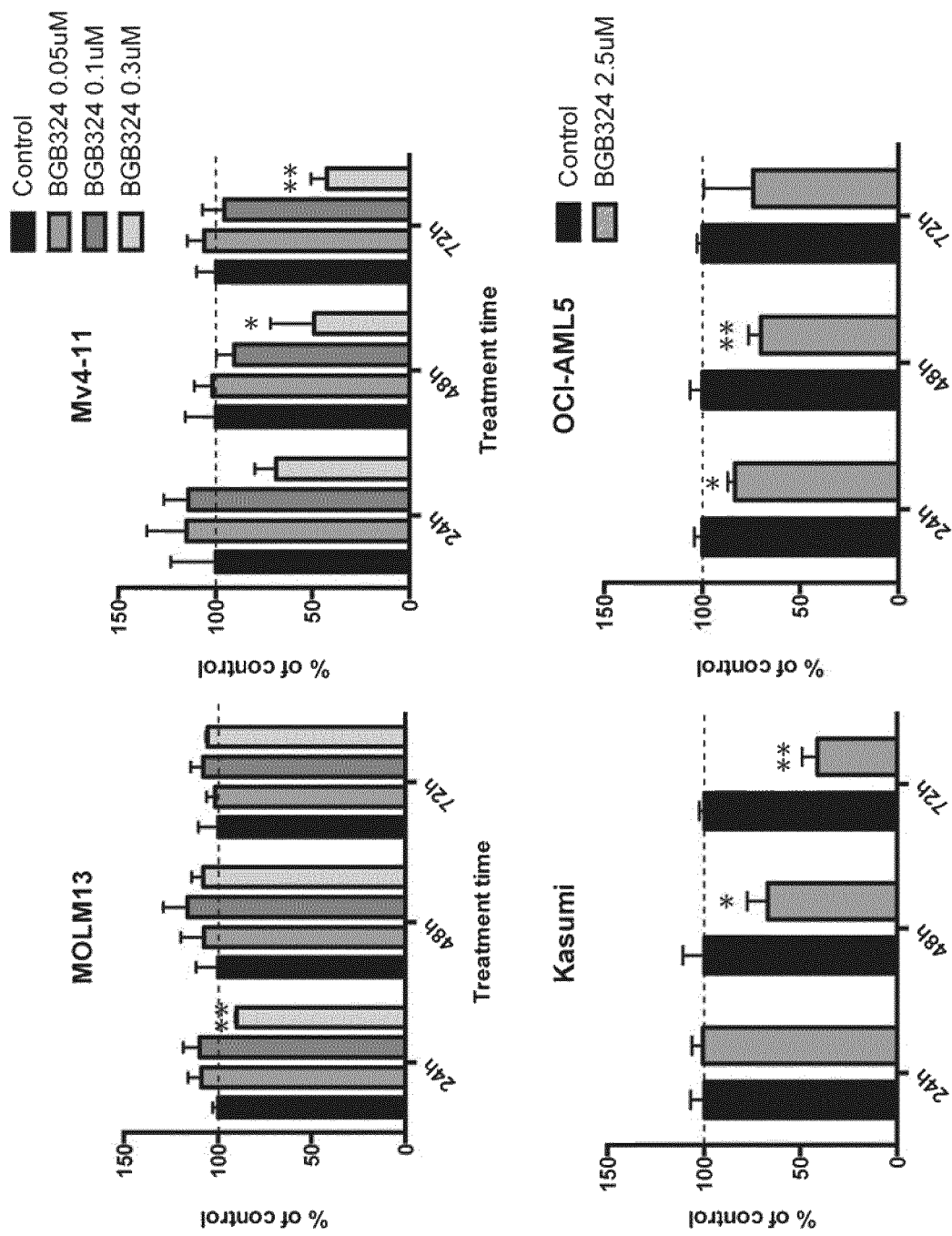
FIG. 15: Response in totErk in AML cell lines after 24, 48 and 72 hours of treatment with BGB324 at 0.05, 0.1 or 0.3 μM (MOLM13 and Mv4-11, upper panels) or at 2.5 μM (Kasumi and OCI-AML5, lower panels). The graphs show geometric mean of fluorescence, calculated as % of control (which is set to 100%—indicated by a dotted line), ±SEM. * indicates significance relative to control, calculated using a two-tailed Student's t-test. *$p<0.05$, **$p<0.005$, n=3.

The total protein expression of Erk in AML cells before and after treatment with BGB324 for 24, 48 and 72 hours (see FIG. 15) was also examined. In MOLM13 only a slight, but significant, reduction of Erk expression after 24 hours of treatment was observed with 0.3 µM of BGB324. However, the protein expression normalized to control-levels at 48 and 72 hours. In Mv4-11 a gradual reduction of Erk expression was observed following treatment with 0.3 µM BGB324 for 24, 48 and 72 hours. Erk expression was significantly lower than control cells at 48 and 72 hours. A reduction of Erk expression following treatment with BGB324 was also seen in Kasumi and OCI-AML5 cells. The reduction was significant at 48 and 72 hours in Kasumi, and at 24 and 48 hours in OCI-AML5.

Thus, reduction of Erk expression after BGB324-treatment appears to be more variable than the other markers investigated. This marker that does not show a similar response within the selected 'responders' vs 'non-responders'.

PLCγ1 in the AML Panel

Figure 16:
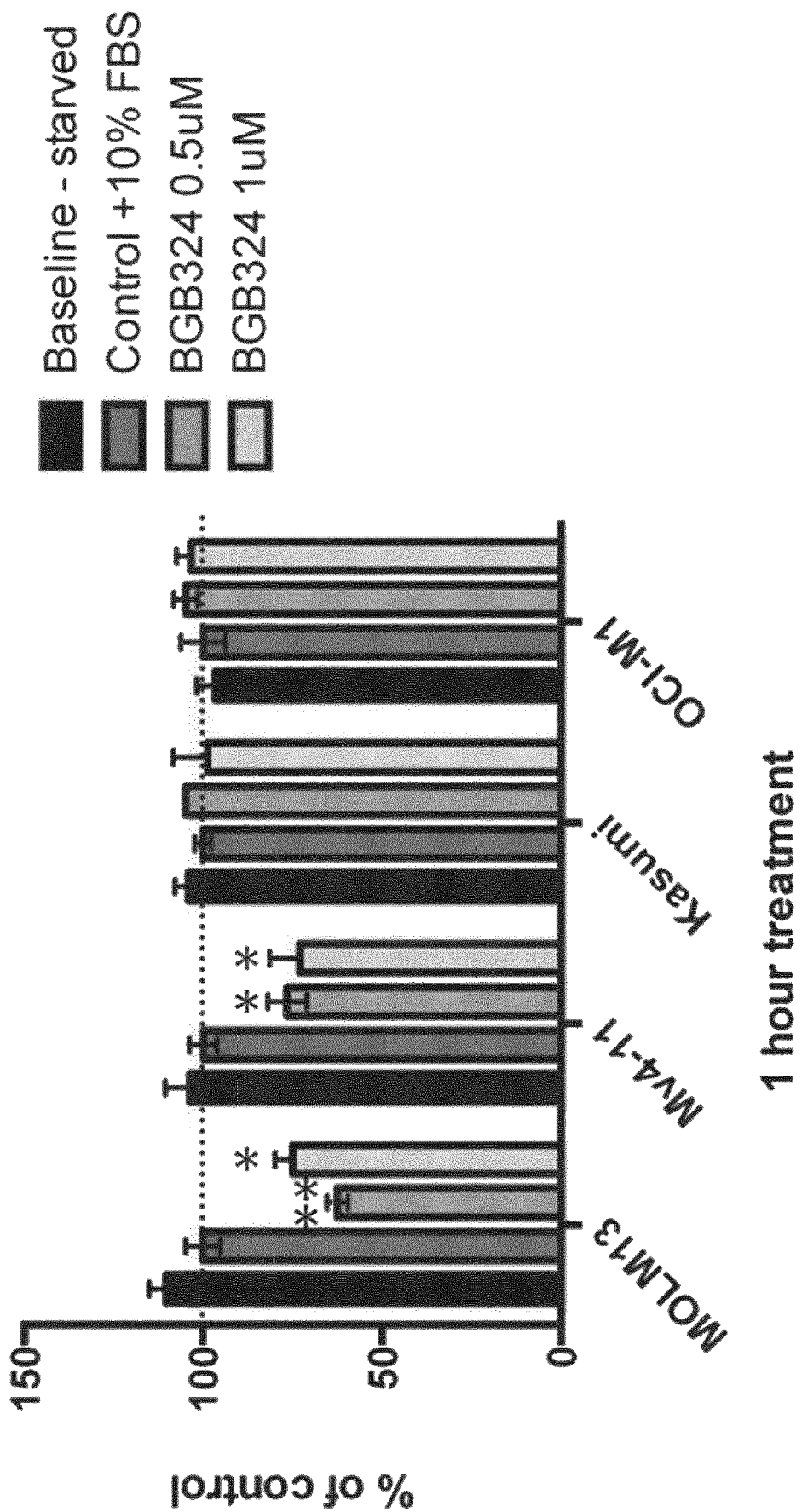
FIG. 16: Response in pPLCγ1 in AML cells after after 1 hour BGB324-treatment at the indicated doses. The graph shows geometric mean of fluorescence, calculated as % of control (10% FBS stimulation, which is set to 100%—indicated with a dotted line), ±SEM. * indicates significance relative to control, calculated using a two-tailed Student's t-test. *$p<0.05$, **$p<0.005$, n=3.

When investigating the activation of PLCγ after BGB324-treatment for 1 hour, it was found that pPLCγ was significantly reduced in MOLM13 and Mv4-11 cells at all treatment doses. No response in PLCγ in Kasumi or OCI-M1 cells was observed (see FIG. 16).

Figure 17:
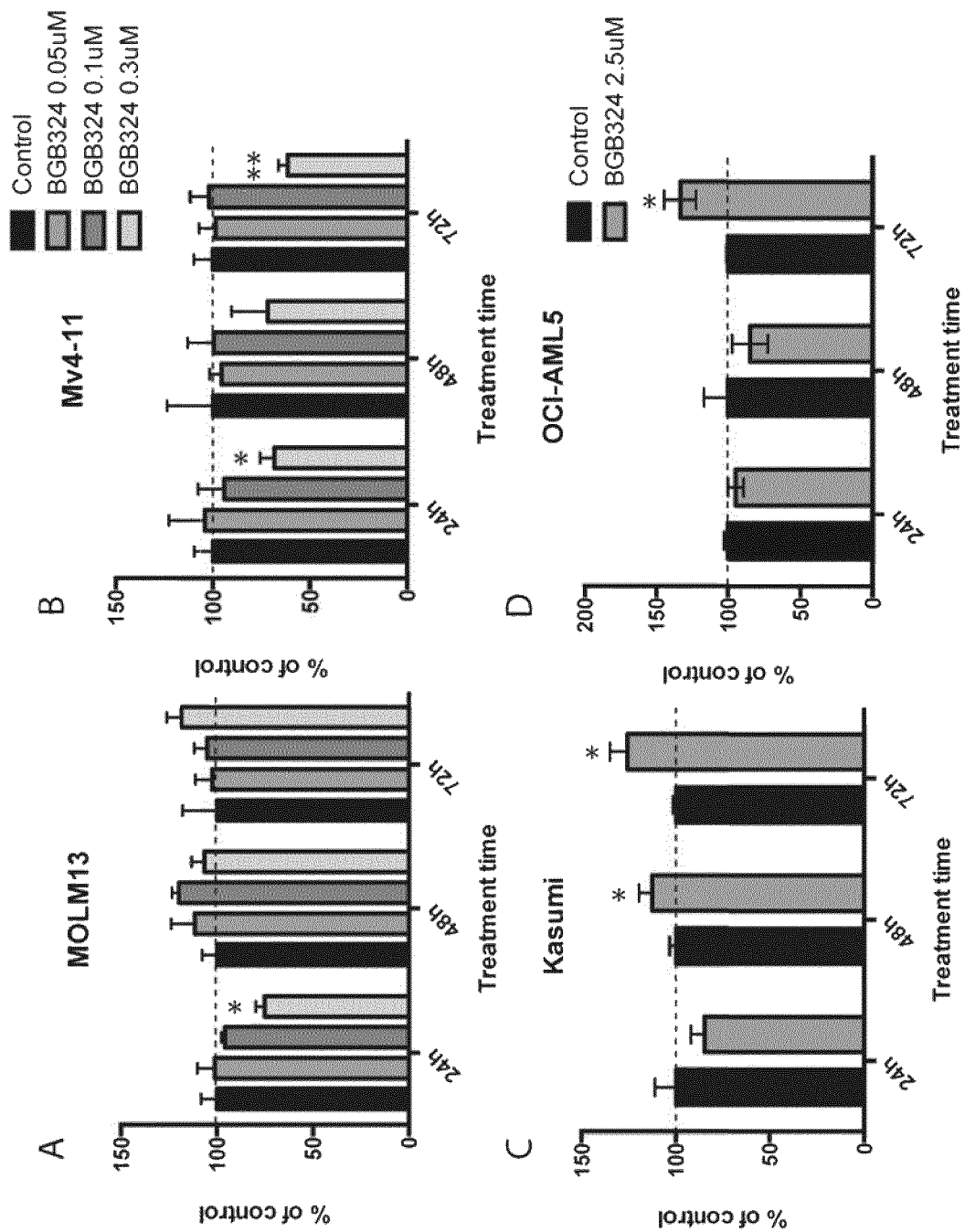
FIG. 17: Response in totPLCγ1 in AML cell lines after 24, 48 and 72 hours of treatment with BGB324 at 0.05, 0.1 or 0.3 μM (MOLM13 and Mv4-11, upper panels) or at 2.5 μM (Kasumi and OCI-AML5, lower panels). The graphs show geometric mean of fluorescence, calculated as % of control (which is set to 100%—indicated by a dotted line), ±SEM. * indicates significance relative to control, calculated using a two-tailed Student's t-test. *$p<0.05$, **$p<0.005$, n=3.

When examining total protein expression of PLCγ1 in the AML cell panel after long-term treatment (24, 48 and 72 hours) with BGB324 a slight but significant reduction at 24 hours in MOLM13 cells was found, and significant reduction at 24 and 72 hours in Mv4-11 at the highest treatment dose (0.3 µM) (see FIG. 17).

The opposite was observed in Kasumi and OCI-AML5; a significant increase of PLCγ1 expression at 48 and 72 hours (only 72 hours in OCI-AML5). Thus, again opposite effects are seen in 'responding' and 'non-responding' cells.

SLFN11 in the AML Panel

Slfn11 was included in the biomarker panel following microarray analysis of Mv4-11 and MOLM13 xenograft material after BGB324-treatment. Schlafen11 (SLFN11) was identified as one of the most significantly downregulated transcripts in an Mv4-11 subcutaneous xenograft model after 14 days of BGB324-treatment. SLFN11 was also significantly downregulated after treatment with only a single dose of BGB324 at 100 mg/kg (samples analyzed 24 hours after drug treatment). However, SLFN11 was not significantly reduced in a MOLM13 systemic xenograft model.

The expression of Slfn11 was evaluated in the AML cell line panel after long-term treatment with BGB324, in order to investigate if the marker could be a universal biomarker or if the downregulation after BGB324-treatment was cell line-specific.

We have found that SLFN11 is expressed in a wide variety of AML cell lines, and we also found indications that SLFN11 should be co-expressed with Axl in normal blood myeloid cells.

Figure 18:
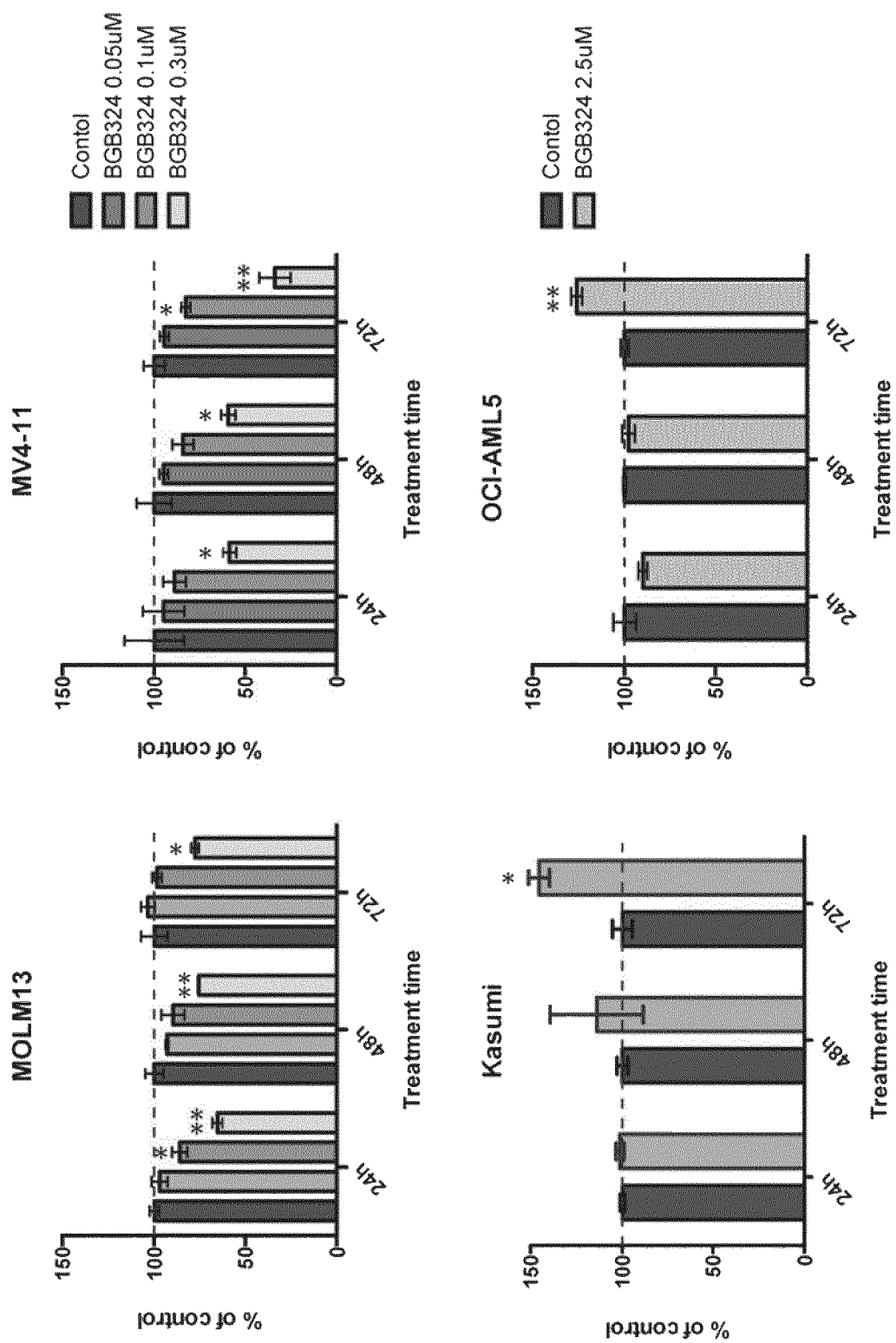
FIG. 18: Response in totSLFN11 in AML cell lines after 24, 48 and 72 hours of treatment with BGB324 at 0.05, 0.1 or 0.3 μM (MOLM13 and Mv4-11, upper panels) or at 2.5 μM (Kasumi and OCI-AML5, lower panels). The graphs show geometric mean of fluorescence, calculated as % of control (which is set to 100%—indicated by a dotted line), ±SEM. * indicates significance relative to control, calculated using a two-tailed Student's t-test. *$p<0.05$, **$p<0.005$, n=3.

When examining total protein expression of SLFN11 in the AML cell panel after long-term treatment (24, 48 and 72 hours) with BGB324, a significant reduction at all time points was found in MOLM13 and Mv4-11 at the highest treatment dose (0.3 µM) (FIG. 18). In Mv4-11, SLFN11 was also significantly reduced at treatment with 0.1 uM BGB324 for 72 hours. In Kasumi and OCI-AML5, the opposite was observed; a significant increase of SLFN11 expression, but only after 72 hours of treatment. At 24 and 48 hours, there was no significant differences between treated- and control cells. Thus, SLFN11 is oppositely regulated in the 'responding' and the 'non-responding' cells, indicating that a reduction of SLFN11 could indicate biological response to BGB324.

PHGDH in the AML Panel

PHGDH was included in the biomarker panel following microarray analysis of Mv4-11 and MOLM13 xenograft material after BGB324-treatment. PHGDH was identified as one of the most significantly downregulated transcripts in an Mv4-11 subcutaneous xenograft model after 14 days of BGB324-treatment.

PHGDH) was found to be significantly downregulated in samples from both the subcutaneous Mv4-11 xenograft model and the systemic MOLM13 xenograft model, as one of only 16 commonly regulated transcripts that were altered more than 1.5-fold after treatment.

The expression of PHGDH was evaluated in the AML cell line panel after long-term treatment with BGB324, in order to investigate if the marker could be a universal biomarker or if the downregulation after BGB324-treatment was cell line-specific.

Figure 19:
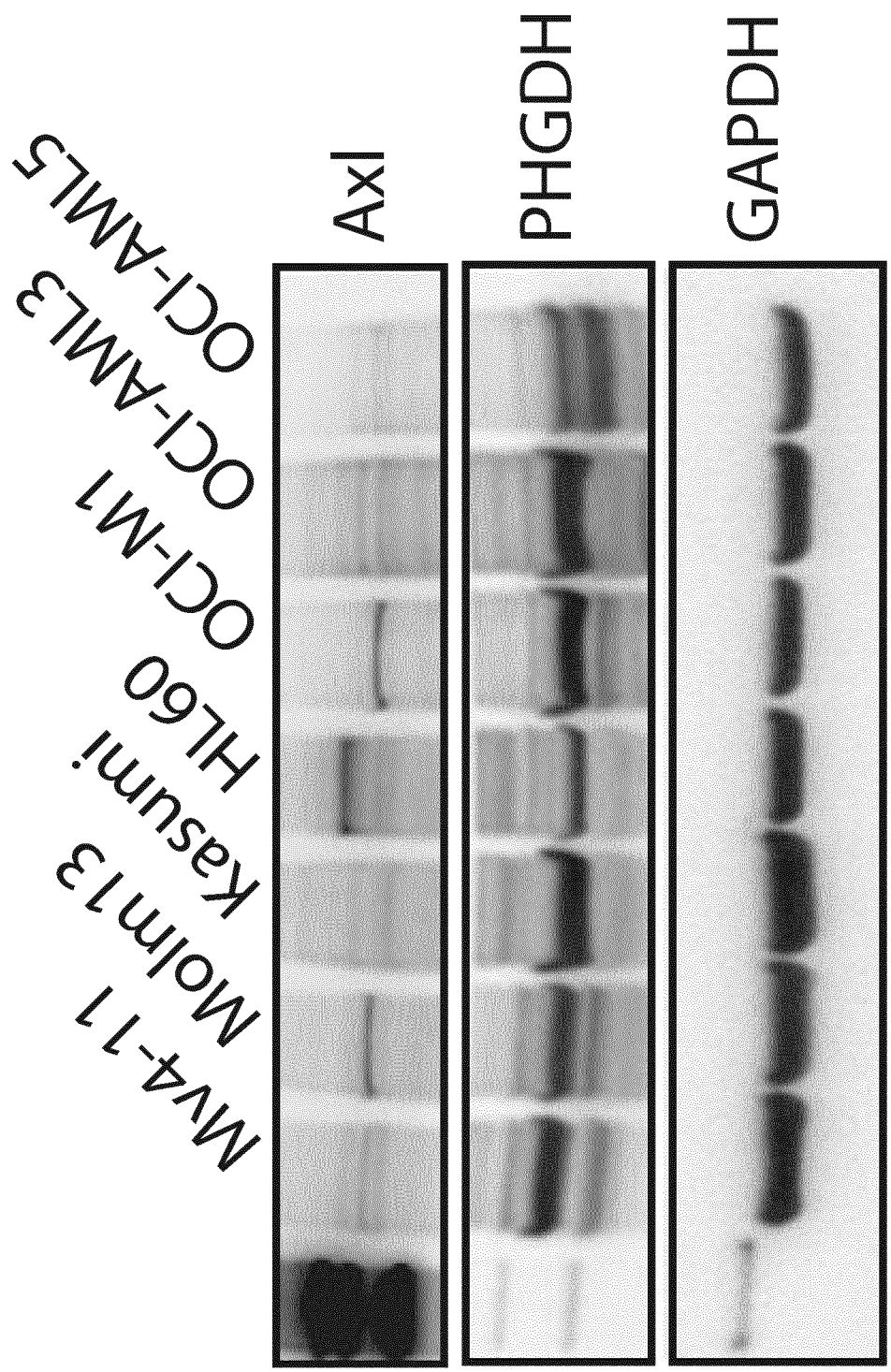
FIG. 19: Western blot showing expression of Axl and PHGDH in a panel of AML cells. The cells have a comparable PHGDH expression level, but PHGDH-expression does not correlate to Axl-expression. GAPDH was used as loading control.

PHGDH expression was evaluated in a number of AML cell lines, including Mv4-11, MOLM13, Kasumi, HL-60, OCI-M1, OCI-AML3 and OCI-AML5. These cells all express PHGDH at a comparable level, with HL60, OCI-M1 and OCI-AML3 having the highest expression. PHGDH-expression does not correlate to Axl expression in these cells (see FIG. 19).

To validate the reduction of PHGDH in in vivo samples found by microarray, the PHGDH expression in tumour material from in vivo samples was investigated by western blot. In MV4-11 tumour lysates from study BGB-X01304 (Mv4-11 sub-q model, animals treated with 25 mg/kg BID, 50 mg/kg BID or 50 mg/kg QD for 15 days and 100 mg/kg single dose, tumours harvested 6 h after dosing), reduction of PHGDH was observed in most of the tumours after 15 day treatment, but only in one of two tumours examined after a single dosing (see FIG. 20A). Therefore, it was investigated at what time point PHGDH is reduced after treatment with a single high dose of BGB324 100 mg/kg.

Figure 20:
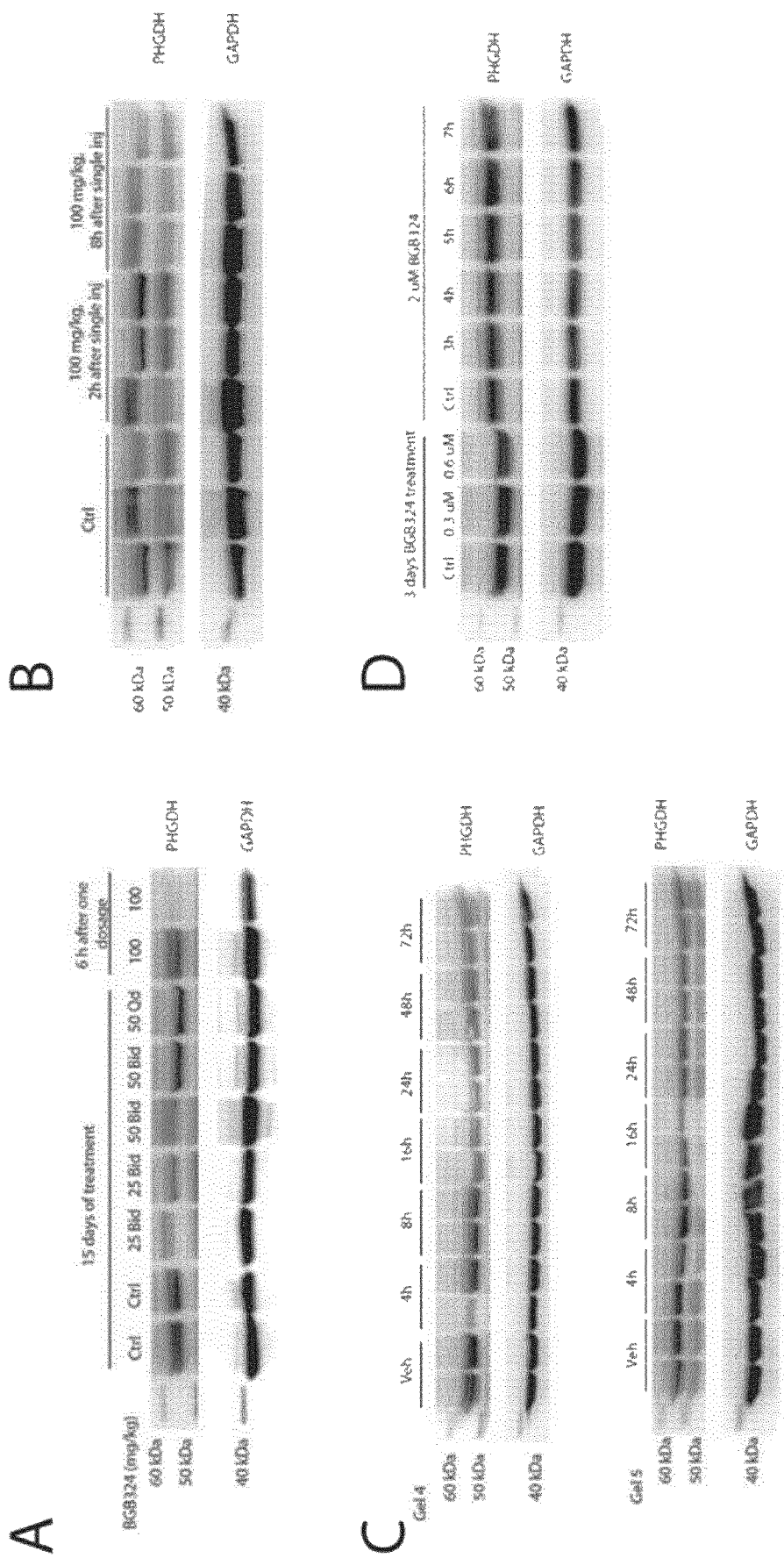
FIG. 20: Western blots showing expression of PHGDH in subcutaneous Mv4-11 xenografts from mice treated with 25 or 50 mg/kg BGB324 for 14 days of 100 mg/kg after 6 hours (A). PHGDH expression is also shown in Mv4-11 xenografts after a single dose of treatment, 100 mg/kg, 2 and 6 hours after treatment (B). Mv4-11 xenografts from mice treated with 50 mg/kg of BGB324 and sacrificed at different time-points after treatment, from 4-72 hours (C). MOLM13 cells treated in vitro with BGB324 for 3 days at 0.3 and 0.6 uM and with 2 uM BGB324 for 3-7 hours (D). GAPDH was used as loading control.

Tumours from study BGB-X01306 (treated with a single high dose of BGB324, 100 mg/kg, tumors harvested at different time points) were examined by western blot, and a reduction of PHGDH observed in three parallel tumours 8 hours after treatment, but not 6 hours after treatment (FIG. 20B). Tumours where the mice had been treated with a single lower dose of BGB324, 50 mg/kg, were also examined (tumour material was harvested at different time points, from 4-72 hours). Here, a stable reduction of PHGDH was observed from 16 hours and onwards, up to 72 hours (see FIG. 20C).

However, when examining MOLM13 cells treated with BGB324 in vitro by western blot, we did not see reduction of PHGDH after three days treatment (0.3 and 0.6 uM) or in a time-course of 3-7 hours after treatment with 2 uM BGB324 (see FIG. 20D). Thus, even though PHGDH was found to be significantly reduced in spleen and bone marrow samples from a systemic MOLM13 model by microarray, PHGDH reduction was not seen in MOLM13 cells treated with BGB324 in vitro by western blot.

Finally, PHGDH was included in the flow cytometric screen of biomarkers in the AML cell line panel after in vitro treatment with BGB324. When examining total protein expression of PHGDH after long-term treatment (24, 48 and 72 hours), a significant reduction of PHGDH was found in Mv4-11 cells treated with 0.3 uM of BGB324 after 24 and 72 hours, but no significant changes in MOLM13 (as expected from the previous western blot data; see FIG. 20D). In Kasumi and OCI-AML5, an increase in PHGDH expression following treatment that was significant was found in Kasumi at 24 hours, and significant in all time points in OCI-AML5 (see FIG. 21).

Example 5

Screening of Selected Biomarkers in in Vivo Samples from a MOLM13 Systemic Xenograft Model Material from an in vivo MOLM13 systemic model was also evaluated by flow cytometry. Expression of the previously evaluated biomarkers was examined in cells isolated from bone marrows and spleens of animals with systemic AML disease (MOLM13, inoculated for 7 days prior to treatment) treated with BGB324 at 50 mg/kg for 4 days. The spleens analysed were from the same study that was analysed by microarray, as mentioned above. The bone marrows were from an identical study that was done at a later time point to get more material for flow analyses.

Cells harvested from spleens, blood and bone marrows of the animals were stained with anti CD33 and CD45 antibodies, to determine if systemic disease was established. CD33/CD45-positive cells were found in spleens (around 10-15%), bone marrows (35-40%) and in the blood (2-6%) of the animals, confirming that the disease was established. There was no significant differences in the percentage of leukemic cells in the BGB324-treated vs. vehicle-treated mice in spleens or bone marrows, but there were a significantly higher percentage of leukemic cells in the blood of BGB324-treated mice (see FIG. 22A).

Cells isolated from spleens and bone marrows were assessed for phosphorylation of Erk, PLCγ1 and Akt, and expression of PHGDH and SLFN11. The samples were also co-stained with CD33, and biomarker expression was only evaluated in CD33-positive cells. A significant reduction of pErk, pPLCγ1, PHGDH and SLFN11 was observed in the bone marrows, and significant reduction of pErk, pPLCγ1 and PHGDH in the spleens (see FIG. 22B). pAkt went down in both tissues after treatment, but due to a large standard deviation in the control group, this change was not significant.

INDUSTRIAL APPLICATION

The invention is industrially applicable through operation of methods in accordance with the invention.

ABBREVIATIONS

Ab Antibody
AML Acute myeloid leukemia
APL Acute promyelocytic leukemia
BID Bis in die (twice a day)
CA Correspondence analysis
CIP Calf intestinal phosphatase
CML Chronic myelogenous leukemia
ER Estrogen receptor
FBS Fetal bovine serum
IB Incubation buffer
ITD Internal tandem duplication
MeOH Methanol
PBMC Peripheral blood mononuclear cells
PBS Phosphate buffered saline
PD Pharmacodynamic
PFA Paraformaldehyde
PHGDH 3-Phosphoglycerate dehydrogenase
PK Pharmacokinetic
PVDF Polyvinylidene fluoride
QD Quaque die (every day, one dose daily)
RTK Receptor tyrosine kinase
SEM Standard error of mean
SLFN11 Schlafen11
TAM Tyro-Axl-Mer

SEQUENCES

PHGDH (human)
Uniprot accession number: O43175

Amino acid sequence:
MAFANLRKVLISDSLDPCCRKILQDGGLQVVEKQNLSKEELIAELQDCEG
LIVRSATKVTADVINAAEKLQVVGRAGTGVDNVDLEAATRKGILVMNTPN
GNSLSAAELTCGMIMCLARQIPQATASMKDGKWERKKFMGTELNGKTLGI
LGLGRIGREVATRMQSFGMKTIGYDPIISPEVSASFGVQQLPLEEIWPLC
DFITVHTPLLPSTTGLLNDNTFAQCKKGVRVVNCARGGIVDEGALLRALQ
SGQCAGAALDVFTEEPPRDRALVDHENVISCPHLGASTKEAQSRCGEEIA
VQFVDMVKGKSLIGVVNAQALTSAFSPHTKPWIGLAEALGTLMRAWAGSP
KGTIQVITQGTSLKNAGNCLSPAVIVGLLKEASKQADVNLVNAKLLVKEA
GLNVTTSHSPAAPGEQGFGECLLAVALAGAPYQAVGLVQGTTPVLQGLNG
AVFRPEVPLRRDLPLLLFRTQTSDPAMLPTMIGLLAEAGVRLLSYQTSLV
SDGETWHVMGISSLLPSLEAWKQHVTEAFQFHF [SEQ ID NO: 1]

mRNA sequence:
CACCTTTCCGCGGGCCGCGGGGATGGCGGCGCAGGGCGTAGGGCCTGGGC
CGGGGTCGGCGGCGCCCCCGGGGCTGGAGGCGGCCCGGCAGAAGCTGGCG
CTGCGGCGGAAGAAGGTGCTGAGCGACTCGGAGATGGAGCTGTACGAGC
TGGCGCAGGCGGCGGGCGGCGCTATCGACCCCGACGTGTTCAAGATCCTG
GTGGACCTGCTGAAGCTGAACGTGGCCCCCCTCGCCGTCTTCCAGATGCT
CAAGTCCATGTGTGCCGGGCAGAGGCTAGCGAGCGAGCCCCAGGACCCTG
CGGCCGTGTCTCTGCCCACGTCGAGCGTGCCCGAGACCCGAGGGAGAAAC
AAAGGCAGCGCTGCCCTCGGGGGAGCATTGGCCCTGGCGGAACAGCAG
CCGCGAAGGATCCAGCCAGAGGATGCCACGCCAGCCCAGCGCTACCAGGC
TGCCCAAGGGGGCGGGCCTGGGAAGAGCCCTACACGGGGCAGCACCTAG
GATGGGGCAGAGACTTGTTGCATCTTTGTCCCCAGCAAAGGCTACATGTT
ACCTCCTTCAATTGATAATAAACCTTTCTGAGATGCAAACTCGAGAATAC
TGCCCAGTTACTCTAGCGCGCCAGGCCGAACCGCAGCTTCTTGGCTTAGG
TACTTCTACTCACAGCGGCCGATTCCGAGGCCAACTCCAGCAATGGCTTT
TGCAAATCTGCGGAAAGTGCTCATCAGTGACAGCCTGGACCCTTGCTGCC
GGAAGATCTTGCAAGAGGGAGGGCTGCAGGTGGTGGAAAAGCAGAACCTT
AGCAAAGAGGAGCTGATAGCGGAGCTGCAGGACTGTGAAGGCCTTATTGT
TCGCTCTGCCACCAAGGTGACCGCTGATGTCATCAACGCAGCTGAGAAAC
TCCAGGTGGTGGGCAGGGCTGGCACAGGTGTGGACAATGTGGATCTGGAG
GCCGCAACAAGGAAGGGCATCTTGGTTATGAACACCCCCAATGGGAACAG
CCTCAGTGCCGCAGAACTCACTTGTGGAATGATCATGTGCCTGGCCAGGC
AGATTCCCCAGGCGACGGCTTCGATGAAGGACGGCAAATGGGAGCGGAAG
AAGTTCATGGGAACAGAGCTGAATGGAAAGACCCTGGGAATTCTTGGCCT
GGGCAGGATTGGGAGAGAGGTAGCTACCCGGATGCAGTCCTTTGGGATGA
AGACTATAGGGTATGACCCCATCATTTCCCCAGAGGTCTCGGCCTCCTTT
GGTGTTCAGCAGCTGCCCCTGGAGGAGATCTGGCCTCTCTGTGATTTCAT
CACTGTGCACACTCCTCTCCTGCCCTCCACGACAGGCTTGCTGAATGACA
ACACCTTTGCCCAGTGCAAGAAGGGGGTGCGTGTGGTGAACTGTGCCCGT
GGAGGGATCGTGGACGAAGGCGCCCTGCTCCGGGCCTGCAGTCTGGCCA
GTGTGCCGGGGCTGCACTGACGTGTTTACGGAAGAGCCGCCACGGGACC
GGGCCTTGGTGGACCATGAGAATGTCATCAGCTGTCCCCACCTGGGTGCC
AGCACCAAGGAGGCTCAGAGCCGCTGTGGGGAGGAAATTGCTGTCAGTT
CGTGGACATGGTGAAGGGGAAATCTCTCACGGGGGTTGTGAATGCCCAGG
CCCTTACCAGTGCCTTCTCTCCACACACCAAGCCTTGGATTGGTCTGGCA
GAAGCTCTGGGGACACTGATGCGAGCCTGGGCTGGGTCCCCAAAGGGAC
CATCCAGGTGATAACACAGGGAACATCCCTGAAGAATGCTGGGAACTGCC
TAAGCCCCGCAGTCATTGTCGGCCTCCTGAAAGAGGCTTCCAAGCAGGCG
GATGTGAACTTGGTGAACGCTAAGCTGCTGGTGAAAGAGGCTGGCCTCAA
TGTCACCACCTCCCACAGCCCTGCTGCACCAGGGGAGCAAGGCTTCGGGG
AATGCCTCCTGGCCGTGGCCCTGGCAGGCGCCCCTTACCAGGCTGTGGGC
TTGGTCCAAGGCACTACACCTGTACTGCAGGGGCTCAATGGAGCTGTCTT
CAGGCCAGAAGTGCCTCTCCGCAGGGACCTGCCCCTGCTCCTATTCCGGA
CTCAGACCTCTGACCCTGCAATGCTGCCTACCATGATTGGCCTCCTGGCA
GAGGCAGGCGTGCGGCTGCTGTCCTACCAGACTTCACTGGTGTCAGATGG
GGAGACCTGGCACGTCATGGGCATCTCCTCCTTGCTGCCCAGCCTGGAAG
CGTGGAAGCAGCATGTGACTGAAGCCTTCCAGTTCCACTTCTAACCTTGG
AGCTCACTGGTCCCTGCCTCTGGGGCTTTTCTGAAGAAACCCACCCACTG
TGATCAATAGGGAGAAAATCCACATTCTTGGGCTGAACGCGGGCCTCT
GACACTGCTTACACTGCACTCTGACCCTGTAGTACAGCAATAACCGTCTA
ATAAAGAGCCTACCCCCAAAAAAAAAA [SEQ ID NO: 2]

Ax1
Uniprot accession number:
P30530

Amino acid sequence:
MAWRCPRMGRVPLAWCLALCGWACAMAPRGTQAEESPFVGNPGNITGARGL
TGTLRCQLQVQGEPPEVHWLRDGQILELADSTQTQVPLGEDEQDDWIVVS
QLRITSLQLSDTGQYQCLVFLGHQTFVSQPGYVLGEGLPYFLEEPEDRTV
AANTPFNLSCQAQGPPEPVDLLWLQDAVPLATAPGHGPQRSLHVPGLNKT
SSFSCEAHNAKGVTTSRTATITVLPQQPRNLHLVSRQPTELEVAWTPGLS
GIYPLTHCTLQAVLSNDGMGIQAGEPDPPEEPLTSQASVPPHQLRLGSLH
PHTPYHIRVACTSSQGPSSWTHWLPVETPEGVPLGPPENISATRNGSQAF
VHWQEPRAPLQGTLLGYRLAYQGQDTPEVLMDIGLRQEVTLELQGDGSVS
NLTVCVAAYTAAGDGPWSLPVPLEAWRPGQAQPVHQLVKEPSTPAFSWPW
VVYVLLGAVVAAACVLILALFLVHRRKKETRYGEVFEPTVERGELVVRYR
VRKSYSRRTTEATLNSLGISEELKEKLRDVMVDRHKVALGKTLGEGEFGA
VMEGQLNQDDSILKVAVKTMKIAICTRSELEDFLSEAVCMKEFDHPNVMR
LIGVCFQGSERESFPAPVVILPFMKHGDLHSFLLYSRLGDQPVYLPTQML
VKFMADIASGMEYLSTKRFIHRDLAARNCMLNENMSVCVADFGLSKKIYN
GDYYRQGRIAKMPVKWIAIESLADRVYTSKSDVWSFGVTMWEIATRGQTP
YPPGVENSEIYDYLRQGNRLKQPADCLDGLYALMSRCWELNPQDRPSFTEL
REDLENTLKALPPAQEPDEILYVNMDEGGGYPEPPGAAGGADPPTQPDPK
DSCSCLTAAEVHPAGRYVLCPSTTPSPAQPADRGSPAAPGQEDGA
[SEQ ID NO: 3]

mRNA sequence:
GCTGGGCAAAGCCGGTGGCAAGGGCTCCCCTGCCGCTGTGCCAGGCAGG
CAGTGCCAAATCCGGGGAGCCTGGAGCTGGGGGAGGGCCGGGGACAGCC
CGGCCCTGCCCCCTCCCCGCTGGGAGCCCAGCAACTTCTGAGGAAAGTT
TGGCACCCATGGCGTGGCGGTGCCCCAGGATGGGCAGGGTCCCGCTGGCC
TGGTGCTTGGCCTGTGCGGCTGGGCGTGCATGGCCCCCAGGGGCACGCA
GGCTGAAGAAAGTCCCTTCGTGGGCAACCCAGGGAATATCACAGGTGCCC
GGGGACTCACGGGCACCCTTCGGTGTCAGCTCCAGGTTCAGGGAGAGCCC
CCCGAGGTACATTGGCTTCGGGATGGACAGATCCTGGAGCTCGCGGACAG
CACCCAGACCCAGGTGCCCCTGGGTGAGGATGAACAGGATGACTGGATAG
TGGTCAGCCAGCTCAGAATCACCTCCCTGCAGCTTTCCGACACGGGACAG
TACCAGTGTTTGGTGTTTCTGGGACATCAGACCTTCGTGTCCCAGCCTGG
CTATGTTGGGCTGGAGGGCTTGCCTTACTTCCTGGAGGAGCCCGAAGACA
GGACTGTGGCCGCCAACACCCCCTTCAACCTGAGCTGCCAAGCTCAGGGA
CCCCAGAGCCCGTGGACCTACTCTGGCTCCAGGATGCTGTCCCCCTGGCC
CACGGCTCCAGGTCACGGCCCCAGCGCAGCCTGCATGTTCCAGGGCTGA
ACAAGACATCCTCTTTCTCCTGCGAAGCCCATAACGCCAAGGGGGTCACC
ACATCCCGCACAGCCACCATCACAGTGCTCCCCCAGCAGCCCCGTAACCT
CCACCTGGTCTCCCGCCAACCCACGGAGCTGGAGGTGGCTTGGACTCCAG
GCCTGAGCGGCATCTACCCCCTGACCCACTGCACCCTGCAGGCTGTGCTG
TCAGACGATGGGATGGGCATCCAGGCGGGAGAACCAGACCCCCCAGAGGA
GCCCCTCACCTCGCAAGCATCCGTGCCCCCCCATCAGCTTCGGCTAGGCA
GCCTCCATCCTCACACCCCTTATCACATCCGCGTGGCATGCACCAGCAGC
CAGGGCCCCTCATCCTGGACCCACTGGCTTCCTGTGGAGACGCCGGAGGG
AGTGCCCCTGGGCCCCCTAAGAACATTAGTGCTACGCGGAATGGGAGCC
AGGCCTTCGTCGATTGGCAAGAGCCCCGGGCGCCCCTGCAGGGTACCCTG
TTAGGGTACCGGCTGGCGTATCAAGGCCAGGACACCCCAGAGGTGCTAAT
GGACATAGGGCTAAGGCAAGAGGTGACCCTGGAGCTGCAGGGGGACGGGT
CTGTGTCCAATCTGACAGTGTGTGTGGCAGCCTACACTGCTGCTGGGGAT
GGACCCTGGAGCCTCCCAGTACCCCTGGAGGCCTGGCGCCCAGTGAAGGA
ACCTTCAACTCCTGCCTTCTCGTGGCCCTGGTGGTATGTACTGCTAGGA
CAGTCGTGGCCGCTGCCTGTGTCCTCATCTTGGCTCTTCTTGTCCAC
CGGCGAAAGAAGGAGACCCGTTATGGAGAAGTGTTTGAACCAACAGTGGA
AAGAGGTGAACTGGTAGTCAGGTACCGCGTGCGCAAGTCCTACAGTCGTC
GGACCACTGAAGCTACCTTGAACAGCCTGGGCATCAGTGAAGAGCTGAAG
GAGAAGCTGCGGGATGTGATGGTGGACCGGCACAAGGTGGCCCTGGGGAA
GACTCTGGGAGAGGGAGAGTTTGGAGCTGTGATGGAAGGCCAGCTCAACC
AGGACGACTCCATCCTCAAGGTGGCTGTGAAGACGATGAAGATTGCCATC
TGCACGAGGTCAGAGCTGGAGGATTTCCTGAGTGAAGCGGTCTGCATGA
GGAATTTGACCATCCCAACGTCATGAGGCTCATCGGTGTCTGTTTCCAGG
GTTCTGAACGAGAGCTTCCCAGCACCTGTGGTCATCTTACCTTTCATG
AAACATGGAGACCTACACAGCTTCCTCCTCTATTCCCGGCTCGGGGACCA
GCCAGTGTACCTGCCCACTCAGATGCTAGTGAAGTTCATGGCAGACATCG
CCAGTGGCATGGAGTATCTGAGTACCAAGAGATTCATACACCGGGACCTG
GCGGCCAGGAACTGCATGCTGAATGAGAACATGTCCGTGTGTGTGGCGGA
CTTCGGGCTCTCCAAGAAGATCTACAATGGGGACTACTACCGCCAGGGAC
GTATCGCCAAGATGCCAGTCAAGTGGATTGCCATTGAGAGTCTAGCTGAC
CGTGTCTACACCAGCAAGAGCGATGTGTGGTCCTTCGGGGTGACAATGTG
GGAGATTGCCACAAGAGGCCAAACCCCATATCCGGGCGTGGAGAACAGCG
AGATTTATGACTATCTGCGCCAGGGAAATCGCCTGAAGCAGCCTGCGGAC
TGTCTGGATGGACTGTATGCCTTGATGTCGCGGTGCTGGGAGCTAAATCC
CCAGGACCGGCCAAGTTTTACAGAGCTGCGGGAAGATTTGGAGAACACA
TGAAGGCCTTGCCTCCTGCCCAGGAGCCTGACGAAATCCTCTATGTCAAC
ATGGATGAGGGTGGAGGTTATCCTGAACCCCCTGGAGCTGCAGGAGGAGC
TGACCCCCAACCCAGCCAGACCCTAAGGATTCCTGTAGCTGCCTCACTG
CGGCTGAGGTCCATCCTGCTGGACGCTATGTCCTCTGCCCTTCCACAACC
CCTAGCCCGCTCAGCCTGCTGATAGGGGCTCCCAGCAGCCCCAGGGCA
GGAGGATGCTGCCTGAGACAACCCTCCACCTGGTACTCCCTCTCAGGATC
CAAGCTAAGCACTGCCACTGGGGAAAACTCCACCTTCCCACTTTTCACC
CCACGCCTTATCCCCACTTGTCAGCCCTGTCTTCCTACCTATCCCACCTCC
ATCCCAGACAGGTCCCTCCCCTTCTCTGTGCAGTAGCATCACCTTGAAAG
CAGTAGCATCACCATCTGTAAAAGGAAGGGGTTGGATTGCAATATCTGAA
GCCCTCCCAGGTGTTAACATTCCAAGACTCTAGAGTCCAAGGTTTAAAGA

SEQUENCES

```
GTCTAGATTCAAAGGTTCTAGGTTTCAAAGATGCTGTGAGTCTTTGGTTC
TAAGGACCTGAAATTCCAAAGTCTCTAATTCTATTAAAGTGCTAAGGTTC
TAAGGCAAAAAAAAAAAAAAAAAAAAA [SEQ ID NO: 4]
```

Akt3
Uniprot accession number:
Q9Y243

Amino acid sequence:
```
MSDVTIVKEGWVQKRGEYIKNWRPRYFLLKIDGSFIGYKEKPQDVDLPY
PLNNFSVAKCQLMKTERPKPNTFIIRCLQWTTVIERTFHVDTPEEREEWT
EAIQAVADRLQRQEEERMNCSPTSQIDNIGEEEMDASTTHHKRKTMNDFD
YLKLLGKGTFGKVILVREKASGKYYAMKILKKEVIIAKDEVAHTLTESRV
LKNTRHPFLTSLKYSFQTKDRLCFVMEYVNGGELFFHLSRERVFSEDRTR
FYGAEIVSALDYLHSGKIVYRDLKLENLMLDKDGHIKITDFGLCKEGITD
AATMKTFCGTPEYLAPEVLEDNDYGRAVDWWGLGVVMYEMMCGRLPFYNQ
DHEKLFELILMEDIKFPRTLSSDAKSLLSGLLIKDPNKRLGGGPDDAKEI
MRHSFFSGVNWQDVYDKKLVPPFKPQVTSETDTRYFDEEFTAQTITITPP
EKYDEDGMDCMDNERRPHFPQFSYSASGRE [SEQ ID NO: 5]
``` mRNA sequence:
```
AGGGGAGTCATCATGAGCGATGTTACCATTGTGAAGGAAGGTTGGGTTCA
GAAGAGGGGAGAATATATAAAAAACTGGAGGCCAAGATACTTCCTTTTGA
AGACAGATGGCTCATTCATAGGATATAAAGAGAAACCTCAAGATGTGGAT
TTACCTTATCCCCTCAACAACTTTTCAGTGGCAAAATGCCAGTTAATGAA
AACAGAACGACCAAAGCCAAACACATTTATAATCAGATGTCTCCAGTGGA
CTACTGTTATAGAGAGAACATTTCATGTAGATACTCCAGAGGAAAGGGAA
GAATGGACAGAAGCTATCCAGGCTGTAGCAGACAGACTGCAGAGGCAAGA
AGAGGAGAGAATGAATTGTAGTCCAACTTCACAAATTGATAATATAGGAG
AGGAAGAGATGGATGCCTACAACCCATCATAAAAGAAAGACAATGAAT
GATTTTGACTATTTGAAACTACTAGGTAAAGGCACTTTTGGGAAAGTTAT
TTTGGTTCGAGAGAAGGCAAGTGGAAAATACTATGCTATGAAGATTCTGA
AGAAAGAAGTCATTATTGCAAAGGATGAAGTGGCACACACTCTAACTGAA
AGCAGAGTATTAAAGAACACTAGACATCCCTTTTTAACATCCTTGAAATA
TTCCTTCCAGACAAAAGACCGTTTGTGTTTGTGATGGAATATGTTAATG
GGGGCGAGCTGTTTTTCCATTTGTCGAGAGAGCGGGTGTTCTCTGAGGAA
CGCACACGTTTCTATGGTGCAGAAATTGTCTCTGCCTTGGACTATCTACA
TTCCGGAAAGATTGTGTACCGTGATCTCAAGTTGGAGAATCTAATGCTGG
ACAAAGATGGCCACATAAAAATTACAGATTTTGGACTTTGCAAAGAAGGG
ATCAACAGATGCAGCCACCATGAAGACATTCTGTGGCACTCCAGAATATCT
GGCACCAGAGGTGTTAGAAGATAATGACTATGGCCGAGCAGTAGACTGGT
GGGGCCTAGGGGTTGTCATGTATGAAATGATGTGTGGGAGGTTACCTTTC
TACAACCAGGACCATGAGAAACTTTTTGAATTAATATTAATGGAAGACAT
TAAATTTCCTCGAACACTCTCTTCAGATGCAAAATCATTGCTTTCAGGGC
TCTTGATAAGGATCCAAATAAACGCCTTGGTGGAGGACCAGATGATGCAA
AAGAAATTATGAGACACAGTTTCTTCTCTGGAGTAAACTGGCAAGATGTA
TATGATAAAAAGCTTGTACCTCCTTTTAAACCTCAAGTAACATCTGAGAC
AGATACTAGATATTTTGATGAAGAATTTACAGCTCAGACTATTACAATAA
CACCACCTGAAAAATATGATGAGGATGGTATGACTGCAGATAATGAGAG
AGGCGGCCGCATTTCCCTCAATTTTCCTACTCTGCAAGTGGACGAGAATA
AGTCTCTTTCATTCTGCTACTTCACTGTCATCTTCAATTTATTACTGAAA
ATGATTCCTGGACATCACCAGTCCTAGCTCTTACACATAGCAGGGCACC
TTCCGACATCCCAGACCAGCCAAGGGTCCTCACCCCTCGCCACCTTTCA
CCTCATGAAAACACACATACACGCAAATACACTCCAGTTTTTGTTTTTGC
ATGAAATTGTATCTCAGTCTAAGGTCTCATGCTGTTGCTACTGTCTT
ACTATTA [SEQ ID NO: 6]
```

Slfn11 (human)
Uniprot accession number:
Q7Z7L1

Amino acid sequence:
```
MEANQCPLVVEPSYPDLVINVGEVTLGEENRKKLQKIQRDQEKERVMRAA
CALLNSGGGVIRMAKKVEHPVEMGLDLEQSLRELIQSSDLQAFFETKQQG
RCFYIFVKSWSSGPFPEDRSVKPRLCSLSSSLYRRSETSVRSMDSREAFC
FLKTKRKPKILEEGPPHKIHKGVYQELPNSDPADPNSDPADLIFQKDYLE
YGEILPFPESQLVEFKQFSTKHFQEYVKRTIPEYVPAFANTGGGYLFIGV
DDKSREVLGCAKENVDPDSLRRKIEQAIYKLPCVHFCQPQRPITFTLKIV
NVLKRGELYGYACMIRVNPFCCAVFSEAPNSWIVEDKYVCSLTTEKWVGM
MTDTDPDLLQLSEDFECQLSLSSGPPLSRPVYSKKGLEHKKELQQLLFSV
PPGYLRYTPESLWRDLISEHRGLEELINKQMQPFFRGILIFSRSWAVDLN
LQEKPGVICDALLIAQNSTPILYTILREQDAEGQDYCTRTAFTLKQKLVN
MGGYTGKVCVRAKVLCLSPESSAEALEAAVSPMDYPASYSLAGTQHMEAL
LQSLVIVLLGFRSLLSDQLGCEVLNLLTAQQYEIFSRSLRKNRELFVHGL
PGSGKTIMAMKIMEKIRNVFHCEAHRILYVCENQPLRNFISDRNICRAET
RKTFLRENFEHIQHIVIDEAQNFRTEDGDWYGKAKSITRRAKGGPGILWV
FLDYFQTSHLDCSGLPPLSDQYPREELTRIVRNADPIAKYLQKEMQVIRS
NPSFNIPTGCLEVFPEAEWSQGVQGTLRIKKYLTVEQIMTCVADTCRRFF
DRGYSPKDVAVLVSTAKEVEHYKELLKAMRKKRVVQLSDACDMLGDHIV
LDSVRRFSGLERSIVFGIHPRTADPAILPNVLICLASRAKQHLYIFPWGG
H [SEQ ID NO: 7]
``` mRNA sequence:
```
GTGCAGTGGCCACGATCTTGGTTCACCACAATCTCGTCTCGAAGGCTCAGG
TGATTCTCTCACCTCAGCCGCCTGAGTAGCTGGGACCACAGTTTCAGCTG
TGAGTTCAACATGGAGGCAAATCAGTGCCCCCTGGTTGTGGAACCATCTT
ACCCAGACCTGGTCATCAATGTAGGAGAAGTGACTCTTGGAGAAGAAAAC
AGAAAAAAGCTGCAGAAAATTCAGAGAGACCAAGAGAAGGAGAGTTAT
GCGGGCTGCATGTGCTTTATTAAACTCAGGAGGAGGAGTGATTCGAATGG
CCAAGAAGGTTGAGCATCCCGTGGAGATGGGACTGGATTTAGAACAGTCT
TTGAGAGAGCTTATTCAGTCTTCAGATCTGCAGGCTTTCTTTGAGACCAA
GCAACAAGGAAGGTGTTTTTACATTTTGTTAAATCTTGGAGCAGTGGCC
CTTTCCCTGAAGATCGCTCTTTCAAGCCCCCGCTTTGCAGCCTCAGTTCTT
CATTATACCTGTAGATCTGAGACCTCTGTGCGTTCCATGGACTCAAGAGA
GGCATTCTGTTTCCTGAAGACCAAAAGGAAGCCAAAAATCTTGGAAGAAG
GACCTTTTCACAAAATTCACAAGGGTGTATACCAAGAGCTCCCTAACTCG
GATCCTGCTGACCCAAACTCGGATCCTGCTGACCTAATTTTCCAAAAGA
CTATCTTGAATATGGTGAAATCCTGCCTTTTCCTGAGTCTCAGTTAGTAG
AGTTTAAACAGTTCTCTACAAAACACTTCCAAGAATATGTAAAAAGGACA
ATTCCAGAATACGTCCCTGCATTTGCAAACACTGGAGGAGGCTATCTTTT
TATTGGAGTGGATGATAAGAGTAGGGAAGTCTCTGGGATGTGCAAAAGAA
AATGTGACCCTGACTCTTTGAGAAGGAAAATAGAACAAGCCATATACAAA
CTACCTTGTGTTCATTTTTGCCAACCCCAACGCCCGATAACCTTCACACT
CAAAATTGTGGATGTGTTAAAAAGGGGAGACTCTATGGCTATGCTTGCAT
GATCAGAGTAAATCCCTTCTGCTGTGCAGTGTTCTCAGAAGCTCCCAATT
CATGGATAGTTGGAGGACAAGTACGTCTGCAGCCTGACAACCGAGAAATGT
GTAGGCATGATGACAGACACAGATCAGATCTTCTACAGTTGTCTGAAGA
TTTTGAATGTCAGCTGAGTCTATCTAGTGGGCCTCCCCTTAGCAGACCAG
TGTACTCCAAGAAAGGCCTGGAACATAAAAAGGAACTCCAGCAACTTTTA
TTTTCAGTCCCACCAGGATATTTGCGATATACTCCAGAGTCACTCTGGAG
GGACCTGATCTCAGAGCACAGAGGACTAGAGGAGTTAATAAATAAGCAAA
TGCAACCTTTCTTTCGGGGAATTTTGATCTTCTCTAGAAGTTGGGCTGTG
GACCTGAACTTGCAGGAGAAGCCAGGAGTCATCTGTGATGCTCTGCTGAT
AGCACAGAACAGCACCCCCATTCTCTACACCATTCTCAGGGAGCAGGATG
CAGAGGGCAGGACTACTGCACTCGCACTGCCTTTACTTTGAAGCAGAAG
CTAGTGAACATGGGGGCTACACCGGGAAGGTGTGTGTCAGGGCCAAGGT
CCTCTGCCTGAGTCCTGAGAGCAGCGCAGAGGCCTTGGAGGCTGCAGTGT
CTCCGATGGATTACCCTGCGTCCTATAGCCTTGCAGGCACCCAGCACATG
GAACCCTGCTGCAGTCCCTCGTGATTGTCTTACTCGGCTTCAGGTCTCTC
TTGAGTGACCAGCTCGGCTGTGAGGTTTTAAATCTGCTCACAGCCCAGCA
GTATGAGATATTCTCCAGAAGCCTCCGCAAGAACAGAGAGTTGTTTGTCC
ACGGCTTACCTGGCTCAGGGAAGACCATCATGGCCATGAAGATCATGGAG
AAGATCAGGAATGTGTTTCACTGTGAGGCACACAGAATTCTCTACGTTTG
TGAAAACCAGCCTCTGAGGAACTTTATCAGTGATAGAAATATCTGCCGAG
CAGAGACCCGGAAAACTTTCCTAAGAGAAAACTTTGAACACATTCAACAC
ATCGTCATTGACGAAGCTCAGAATTTCCGTACTGAAGATGGGGACTGGTA
TGGGAAGGCAAAAAGCATCACTCGGAGACGCAAAGGGTGGCCCAGGAATTC
TCTGGATCTTTCTGGATTACTTTCAGACCAGCCACTTGGATTGCAGTGGC
CTCCCTCCTCTCTCAGACCAATATCCAAGAGAAGAGCTCACCAGAATAGT
TCGCAATGCAGATCCAATAGCCAAGTACTTACAAAAGAAATGCAGGTTA
TTAGAAGTAATCCTTCATTTAACATCCCCACTGGGTGCCTCGAGGTATTT
CCTGAAGCCGAATGGTCCCAGGGTGTTCAGGGAACCTTACGAATTAAGAA
ATACTTGACTGTGGAGCAAATAATGACCTGTGTGGCAGACACGTGCAGGC
GCTTCTTTGATAGGGGCTATTCTCCAAAGGATGTTGCTGTGCTTGTCAGC
ACCGCAAAAGAAGTGGAGCACTATAAGTATGAGCTCTTGAAAGCAATGAG
GAAGAAAAGGGTGGTGCAGCTCAGTGATGCATGTGATATGTTGGGTGATC
ACATTGTGTTGGACAGTGTTCGGCGATTCTCAGGCCTGGAAAGGAGCATA
GTGTTTGGGATCCATCCAAGGACAGCTGACCCAGCTATCTTACCCAATGT
TCTGATCTGTCTGGCTTCCAGGGCAAAACAACACCTGTATATTTTTCCGT
GGGGTGGCCATTAGGAAGAACTCCAAATCAAAATGTATGTAAATGTCTA
TGGGTGACAGTCTGCTGATGGTAGAAACCTTTCTTTTTAGTTCACAAGTC
AGAGATTTGGACGGAGCTGACACAAAGAGTTTGGAGCTCCCCCATTTCTG
GCTCTCCTTTCAGGGGTTCCTTCCCCAAACCTTTTCAGCAGCGGTGGCTG
CCCCCCATTCTGACCCCTGACTCTTCCAGCCAGAAAGATGGTGGTTTTCT
AAAAGGAACTTTAGCTGTCCTGCACAATGCCGATCTGTCTGTTGCATTTTG
GGTAAAAGCCATAAAAATAAGAAACTCAGCCTGTGGCCTTTCTTTCTTCC
AAGGCTGGGCTTCTTTTTTTAAGTGACTTCATGCAGTTTGTTGCTTTTAA
AAATTTGTCCAAGATCGTTTTTCTGCAGAAGCATGGTCTGTTAGGAGCTTA
CTGGCCGTAGCAGAAGCAATTGTTTTCCTGAATTCTTGACATTTATCTTTG
CTGTATTCATTTAGGGCTTGGGAGAGTCCGAAGATAATTCAGTCACTGTC
AGATTAATAATTCTGTCAGGACAAAGAATACCGTTATGATTATTTAATCC
TTTAAAATTGTGGTCTCCAGAGCTTGTTCTCAGAATGGCCCAGACCAAGC
CTTAATTGTGATAGTGAATATTAATGGTCACTTTAAGGAGAAATTTAGG
CCAAGATGAAATGAACATAAACCTGTTTGCCCTGGCTTTCAGTGGAAGAT
```

| SEQUENCES |
|---|
| GATATTAGAGACCAAAATCTGGTTCTGAAGGTGTGTATCAGCCCTAAGGT<br>GAACCAGACTTGGGAAAGATTGTCTTTAAAAATCAATGAGTTTATGTTTT<br>AACTTCTCAGCTTAGTTCTATGCATTGCTCTATAACACACCTAGTTAAGT<br>TTTATGTTATTCTTGAACTGTGATTTTTTTCTATTTACTTTCATGGTTT<br>GGTGGGCCATTGTTATGGACTGAATGTTTGTGTCCCACCCTTCACCCCCA<br>AATTCCCGTGTTGAAGCCCCAACCTGCACTGTGGAGCTGGGGCTGCTAAG<br>GAAGTAATTAAGGTTACATGAAGTCATGGTGGGGCTCTGATCTGCTAAGG<br>TTGGTGTCCTTATAGGGAGAGACCCCAGAGAGCTTGTTCCCTCCCTCCCT<br>GTGCATGCAAACAAGAGGGCATGGGAGCACACAGAGAGATGGCAGCCACC<br>TACAAGCCAAGAGGAGAAGCCTCACAATCAAACTCTCGCTGCTGGCGAGA<br>GTCTTGGACTCTGTCTTGGACTTCCAGCCTCCAGACTGTGAGAAACAAAT<br>TTCTGTTGTTTCAGCTTCTCAGTCTCTGGTGTTTTGTTATTGCAGCCTGA<br>GAACACAGCTGTACGATTATTTGTCAAACAGAAAACACTGATACTTAACA<br>ATGCTAATGCAATTATTTATTTGCTTTTCAGTCTCTACAAAACGTTCTAA<br>AACACTAATCTAAATATTAACAGTAAAATATTTGCATAATAATGGAAAC<br>TAAGAAATCATATGACCAATATTTCACTTATTGGTAATCTTACTCTACTG<br>ATTTCCCCCAGACTGTGATTTTTGAACTTCTTGCCTTTCTCCTGTCTT<br>TCTGTGTTTATTCATGGAATTCCAGTTATCTGGGCTTGAAATTGCAGGCT<br>CTCCTAACTTAAGCAAAATCTGACAGATCAGCAAAATGAGATAAATGTTT<br>CTTTTTCTTTCTGACTGCCATTAAATCAGATACAACTCAGCATTAAAAAG<br>CTATCTTTGTAAATGTTGTTACTAATAAATTAGTCTTATAAGATCCCTGG<br>ACTTTGGAGTTGTTGCA [SEQ ID NO: 8] |
| ERK 1 (human)<br>Uniprot accession number:<br>P27361<br><br>Amino acid sequence:<br>MAAAAAQGGGGGEPRRTEGVGPGVPGEVEMVKGQPFDVGPRYTQLQYIGE<br>GAYGMVSSAYDHVRKTRVAIKKISPFEHQTYCQRTLREIQILLRFRHENV<br>IGIRDILRASTLEAMRDVYIVQDLMETDLYKLLKSQQLSNDHICYFLYQI<br>LRGLKYIHSANVLHRDLKPSNLLINTTCDLKICDFGLARIADPEHDHTGF<br>LTEYVATRWYRAPEIMLNSKGYTKSIDIWSVGCILAEMLSNRPIFPGKHY<br>LDQLNHILGILGSPSQEDLNCIINMKARNYLQSLPSKTKVAWAKLFPKSD<br>SKALDLLDRMLTFNPNKRITVEEALAHPYLEQYYDPTDEPVAEEPFTFAM<br>ELDDLPKERLKELIFQETARFQPGVLEAP [SEQ ID NO: 9]<br><br>mRNA sequence:<br>CGTTCCTCGGCGCCGCCGGGGCCCCAGAGGGCAGCGGCAGCAACAGCAGC<br>AGCAGCAGCAGCGGGAGTGGAGATGGCGGCGGCGGCGGCTCAGGGGGGCG<br>GGGGCGGGGAGCCCCGTAGAACCGAGGGGGTCGGCCCGGGGGTTCCCGGG<br>GAGGTGGAGATGGTGAAGGGGCAGCCGTTCGACGTGGGCCCGCGCTACAC<br>GCAGTTGCAGTACATCGGCGAGGGCGCGTACGGCATGGTCAGCTCGGCCT<br>ATGACCACGTGCGCAAGACTCGCGTGGCCATCAAGAAGATCAGCCCCTTC<br>GAACATCAGACCTACTGCCAGCGCACGCTCCGGGAGATCCAGATCCTGCT<br>GCGCTTCCGCCATGAGAATGTCATCGGCATCCGAGACATTCTGCGGGCGT<br>CCACCCTGGAAGCCATGAGAGATGTCTACATTGTGCAGGACCTGATGGAG<br>ACTGACCTGTACAAGTTGCTGAAAAGCCAGCAGCTGAGCAATGACCATAT<br>CTGCTACTTCCTCTACCAGATCCTGCGGGGCCTCAAGTACATCCACTCCG<br>CCAACGTGCTCCACCGAGATCTAAAGCCCTCCAACCTGCTCAGCAACACC<br>ACCTGCGACCTTAAGATTTGTGATTTCGGCCTGGCCCGGATTGCCGATCC<br>TGAGCATGACCACACCGGCTTCCTGACGGAGTATGTGGCTACGCGCTGGT<br>ACCGGGCCCCAGAGATCATGCTGAACTCCAAGGGCTATACCAAGTCCATC<br>GACATCTGGTCTGTGGGCTGCATTCTGGCTGAGATGCTCTCTAACCGGCC<br>CATCTTCCCTGGCAAGCACTACCTGGATCAGCTCAACCACATTCTGGGCA<br>TCCTGGGCTCCCCATCCCAGGAGGACCTGAATTGTATCATCAACATGAAG<br>GCCCGAAACTACCTACAGTCTCTGCCCTCCAAGACCAAGGTGGCTTGGGC<br>CAAGCTTTTCCCCAAGTCAGACTCCAAAGCCCTTGACCTGCTGGACCGGA<br>TGTTAACCTTTAACCCCAATAAACGGATCACAGTGGAGGAAGCGCTGGCT<br>CACCCCTACCTGGAGCAGTACTATGACCCGACGGATGAGCCAGTGGCCGA<br>GGAGCCCTTCACCTTCGCCATGGAGCTGGATGACCTACCTAAGGAGCGGC<br>TGAAGGAGCTCATCTTCCAGGAGACAGCACGCTTCCAGCCCGGAGTGCTG<br>GAGGCCCCCAGCCCAGACAGACATCTCTGCACCCTGGGGCCTGGACCTG<br>CCTCCTGCCTGCCCCTCTCCCGCCAGACTGTTAGAAAATGGACACTGTGC<br>CCAGCCCGGACCTTGGCAGCCCAGGCCGGGGTGGAGCATGGGCCTGGCCA<br>CCTCTCTCCTTTGCTGAGGCCTCCAGCTTCAGGCAGGCCAAGGCCTTCTC<br>CTCCCCACCCGCCCTCCCCACGGGGCCTCGGGAGCTCAGGTGGCCCCAGT<br>TCAATCTCCCGCTGCTGCTGCTGCTGCGCCCTTACCTTCCCCAGCGTCCC<br>AGTCTCTGGCAGTTCTGGAATGGAAGGGTTCTGGCTGCCCAACCTGCTG<br>AAGGGCAGAGGTGGAGGGTGGGGGGCGCTGAGTAGGGACTCAGGGCCATG<br>CCTGCCCCCTCATCTCATTCAAACCCACCCTAGTTTCCCTGAAGGAAC<br>ATTCCTTAGTCTCAAGGGCTAGCATCCCTGGACAGGCAGGCCGGGCCGAA<br>TCCCCTCCCTGTCAAAGCTGTCACTTCGCGTGCCCTCGCTGCTTCTGTGT<br>GTGGTGAGCAGAAGTGGAGCTGGGGGGCGTGGAGAGCCCGGCGCCCTGC<br>CACCTCCCTGACCCGTCTAATATATAAATATAGAGATGTGTCTATGGCTG<br>AAAAAAAAAAAAAAAA [SEQ ID NO: 10] |
| PLCγ1<br>Uniprot accession number:<br>P19174<br><br>Amino acid sequence:<br>MAGAASPCANGCGPGAPSDAEVLHLCRSLEVGTVMTLFYSKKSQRPERKT<br>FQVKLETRQITWSRGADKIEGAIDIREIKEIRPGKTSRDFDRYQEDPAFR<br>PDQSHCFVILYGMEFRLKTLSLQATSEDEVNMWIKGLTWLMEDTLQAPTP<br>LQIERWLRKQFYSVDRNREDRISAKDLKNMLSQVNYRVPNMRFLRERLTD<br>LEQRSGDITYGQFAQLYRSLMYSAQKTMDLPFLEASTLRAGERPELCRVS<br>LPEFQQFLLDYQGELWAVDRLQVQEFMLSFLRDPLREIEEPYFFLDEFVT<br>FLFSKENSVWNSQLDAVCPDTMNNPLSHYWISSSHNTYLTGDQFSSESSL<br>EAYARCLRMGCRCIELDCWDGPDGMPVIYHGHTLTTKIKFSDVLHTIKEH<br>AFVASEYPVILSIEDHCSIAQQRNMAQYFKKVLGDTLLTKPVEISADGLP<br>SPNQLKRKILIKHKKLAEGSAYEEVPTSMMYSENDISNSIKNGILYLEDP<br>VNHEVVYPHYFVLTSSKIYYSEETSSDQGNEDEEEPKEVSSSTELHSNEK<br>WFHGKLGAGRDGRHIAERLLTEYCIETGAPDGSFLVRESETFVGDYTLSF<br>WRNGKVQHCRIHSRQDAGTPKFFLTDNLVFDSLYDLITHYQQVPLRCNEF<br>EMRLSEPVPQTNAHESKEVVYHASLTRAQAEHMLRVPRDGAFLVRKRNE<br>PNSYAISFRAEGKIKHCRVQQEGQTVMLGNSEFDSLVDLISYYEKHPLYR<br>KMKLRYPINEEALEKIGTAEPDYGALYEGRNPGFYVEANPMPTFKCAVKA<br>LFDYKAQREDELTFIKSAIIQNVEKQEGGWWRGDYGGKKQLWFPSNYVEE<br>MVNPVALEPEREHLDENSPLGDLLRGVLDVPACQIAIRPEGKNNRLFVFS<br>ISMASVAHWSLDVAADSQEELQDVWKKIREVAQTADARLTEGKIMERRKK<br>IALELSELVVYCRPVPFDEEKIGTERACYRDMSSFPETKAEKYVNKAKGK<br>KFLQYNRLQLSRIYPKGQRLDSSNYDPLPMWICGSQLVALNFQTPDKPMQ<br>MNQALFMTGRHCGYVLQPSTMRDEAFDPFDKSSLRGLEPCAISIEVLGAR<br>HLPKNGRGIVCPFVEIEVAGAEYDSTKQKTEFVVDNGLNPVWPAKPFHFQ<br>ISNPEFAFLRFVVYEEDMFSDQNFLAQATFPVKGLKTGYRAVPLKNNYSE<br>DLELASLLIKIDIFPAKENGDLSPFSGTSLRERGSDASGQLFHGRAREGS<br>FESRYQQPFEDFRISQEHLADHFDSRERRAPRRTRVNGDNRL<br>[SEQ ID NO: 11]<br><br>mRNA sequence:<br>GGGGTGCCGCCGCCGCCGTTGCGCTTGCTCCCGGGCGGTCCTGGCCTGTG<br>CCGCCGCGCCCCAGCGTCGGAGCCATGGCGGGCGCCGCGTCCCCTTGC<br>GCCAACGGCTGCGGGCCCGGCGCGCCCTCGGACGCCGAGGTGCTGCACCT<br>CTGCCGCAGCCTCGAGGTGGGCACCGTCATGACTTTGTTCTACTCCAAGA<br>AGTCGCAGCGACCCGAGCGGAAGACCTTCCAGGTCAAGCTGGAGACGCGC<br>CAGATCACGTGGAGCCGGGGCGCCGACAAGATCGAGGGGGCCATTGACAT<br>TCGTGAAATTAAGGAGATCCGCCCAGGGAAGACCTCACGGGACTTTGATC<br>GCTATCAAGAGGACCCAGCTTTCCGGCCAGACCAGTCACATTGCTTTGTC<br>ATTCTCTATGGAATGGAATTTCGCCTGAAAACGCTGAGCCTGCAAGCCAC<br>ATCTGAGGATGAAGTGAACATGTGGATCAAGGGCTTAACTTGGCTGATGG<br>AGGATACATTGCAGGCACCCACACCCCTGCAGATTGAGAGGTGGCTCCGG<br>AAGCAGTTTTACTCAGTGGATCGGAACCGTGAGGATCGTATATCAGCCAA<br>GGACCTGAAGAACATGCTGTCCCAGGTCAACTACCGGGTCCCAACATGC<br>GCTTCCTCCGAGAGCGGCTGACGGACCTGGAGCAGCGCAGCGGGGACATC<br>ACCTACGGGCAGTTTGCTCAGCTGTACCGCAGCCTCATGTACAGCGCCCA<br>GAAGACGATGGACCTCCCCTTCTTGGAAGCCAGTACTCTGAGGGCTGGG<br>AGCGGCCGGAGCTTTGCCGAGTGTCCCTTCCTGAGTTCCAGCAGTTCCTT<br>CTTGACTACCAGGGGGAGCTGTGGGCTGTTGATCGCCTCCAGGTGCAGGA<br>GTTCATGCTCAGCTTCCTCCGAGACCCCTTACGGAGAGATCGAGGAGCCAT<br>ACTTCTTCCTGGATGAGTTTGTCACCTTCCTGTTCTCCAAAGAGAACAGT<br>GTGTGGAACTCGCAGCTGGATGCAGTATGCCCGGACACCATGAACAACCC<br>TCTTTCCCACTACTGGATCTCCTCCTCGCACAACACGTACCTGACCGGGG<br>ACCAGTTCTCCAGTGAGTCCTCCTTGGAAGCCTATGCTCGCTGCCTGCGG<br>ATGGGCTGTCGCTGCATTGAGTTGGACTGCTGGGACGGCCCGGATGGGAT<br>GCCAGTTATTTACCATGGGCACACCCTTACCACCAAGATCAAGTTCTCAG<br>ATGTCCTGCACACCATCAAGGAGCATGCCTTTGTGGCCTCAGAGTACCCA<br>GTCATCCTGTCCATTGAGGACCACTGCAGCATTGCCCAGCAGAGAAACAT<br>GGCCCAATACTTCAAGAAGGTGCTGGGGGACACACTTCTCACCAAGCCCG<br>TGGAGATCTCTGCCGACGGGCTCCCCTCACCCAACCAGCTTAAGAGGAAG<br>ATCCTCATCAAGCACAAGAAGCTGGCTGAGGGCAGTGCCTACGAGGAGGT<br>GCCTACATCCATGATGTACTCTGAGAACGACATCAGCAACTCTATCAAGA<br>ATGGCATCCTGTACCTGGAGGACCCCGTGAACCACGAAGTTGTATCCCAC<br>TACTTTGTTCTGACCAGCAGCAAGATCTACTACTCTGAGGAGACCAGCAG<br>TGACCAGGGCAACGAGGATGAGGAGGAGCCCAAGGAGGTCAGCAGCAGCA<br>CAGAGCTGCACTCCAATGAGAAGTGGTTCCATGGGAAGCTAGGGGCAGGG<br>CGTGACGGGCGTCACATCGCTGAGCGCCTGCTTACTGATACTGCATCGAG<br>ACCGGAGCCCCTGACGGCTCCTTCCTCGTGCGAGAGAGTGAGACCTTCGT<br>GGGCGACTACACGCTCTCTTTCTGGCGGAACGGGAAAGTCCAGCACTGCC<br>GTATCCACTCCCGGCAAGATGCTGGGACCCCAAGTTCTTCTTGACAGAC<br>AACCTCGTCTTTGACTCCCTCTATGACCTCATCACGCACTACCAGCAGGT<br>GCCCCTGCGCTGTAATGAGTTTGAGATGCGACTTTCAGAGCCTGTCCCAC<br>AGACCAACGCCCACGAGAGCAAAGAGTGGTACCACGCGAGCCTGACCAGA<br>GCACAGGCTGAGCACATGCTAATGCGCGTCCCTCGTGATGGGGCCTTCCT |

SEQUENCES

```
GGTGCGGAAGCGGAATGAACCCAACTCATATGCCATCTCTTTCCGGGCTG
AGGGCAAGATCAAGCATTGCCGTGTCCAGCAAGAGGGCCAGACAGTGATG
CTAGGGAACTCGGAGTTCAGCCTTGTTGACCTCATCAGCTACTATGA
GAAACACCCGCTATACCGCAAGATGAAGCTGCGCTATCCCATCAACGAGG
AGGCACTGGAGAAGATTGGCACAGCTGAGCCTGACTACGGGGCCCTGTAT
GAGGGACGCAACCCTGGCTTCTATGTAGAGGCAAACCCTATGCCAACTTT
CAAGTGTGCAGTCAAAGCCCTCTTTGACTACAAGGCCCAGAGGGAGGACG
AGCTGACCTTCATCAAGAGCGCCATCATCCAGAATGTGGAGAAGCAAGAG
GGAGGCTGGTGGCGAGGGGACTACGGAGGGAAGAAGCAGCTGTGGTTCCC
ATCAAACTACGTGGAAGAGATGGTCAACCCCGTGGCCCTGGAGCGGAGA
GGGAGCACTTGGACGAGAACAGCCCCCTAGGGGACTTGCTGCGGGGGGTC
TTGGATGTGCCGGCTTGTCAGATTGCCATCCGTCCTGAGGGCAAGAACAA
CCGGCTCTTCGTCTTCTCCATCAGCATGGCGTCGGTGGCCCACTGGTCCC
TGGATGTTGCTGCCGACTCACAGGAGGAGCTGCAGGACTGGGTGAAAAAG
ATCCGTGAAGTGGCCCAGACAGCAGACGCCAGGCTCACTGAAGGGAAGAT
AATGGAACGGAGGAAGAAGATTGCCCTGGAGCTCTCTGAACTTGTCGTCT
ACTGCCGGCCTGTTCCCTTTGATGAAGAGAAGATTGGCACAGAACGTGCT
TGCTACCGGGACATGTCATCCTTCCCGGAAACCAAGGCTGAGAAATACGT
GAACAAGGCCAAAGGCAAGAAGTTCCTTCAGTACAATCGACTGCAGCTCT
CCCGCATCTACCCCAAGGGCCAGCGACTGGATTCCTCCAACTACGATCCT
TTGCCCATGTGGATCTGTGGCAGTCAGCTTGTGGCCCTCAACTTCCAGAC
CCCTGACAAGCCTATGCAGATGAACCAGGCCCTCTTCATGACGGGCAGGC
ACTGTGGCTACGTGCTGCAGCCAAGCACCATGCGGGATGAGGCCTTCGAC
CCCTTTGACAAGAGCAGCCTCCGCGGGCTGGAGCCATGTGCCATCTCTAT
TGAGGTGCTGGGGGCCCGACATCTGCCAAAGAATGGCCGAGGCATTGTGT
GTCCTTTTGTGGAGATTGAGGTGGCTGGAGCTGAGTATGACAGCACCAAG
CAGAAGACAGAGTTTGTGGTGGACAATGGACTCAACCCTGTATGGCCAGC
CAAGCCCTTCCACTTCCAGATCAGTAACCCTGAATTTGCCTTTCTGCGCT
TCGTGGTGTATGAGGAAGACATGTTTAGTGACCAGAATTTCCTGGCTCAG
GCTACTTTCCCAGTAAAAGGCCTGAAGACAGGATACAGAGCAGTGCCTTT
GAAGAACAACTACAGTGAGGACCTGGAGTTGGCCTCCCTGCTGATCAAGA
TTGACATTTTCCCTGCCAAGGAGAATGGTGACCTCAGTCCCTTCAGTGGT
ACGTCCCTGCGGGAGCGGGCTCAGATGCCTCAGGCCAGCTGTTTCATGG
CCGAGCCCGGGAAGGCTCCTTTGAATCCCGCTACCAGCAGCCGTTTGAGG
ACTTCCGCATCTCCCAGGAGCATCTGCAGACCATTTTGACAGTCGAGAAC
GAAGGGCCCCAAGAAGGACTCGGGTCAATGGAGACAACCGCCTCTAGTTG
TACCCCAGCCTCGTTGGAGAGCAGCAGGTGCTGTGCGCCTTGTAGAATGC
CGCGAACTGGGTTCTTTGGAAGCAGCCCCCTGTGGCGGCCTTCCGGGTCT
CGCAGCCTGAAGCCTGGATTCCAGCAGTGAATGCTAGACAGAAACCAAGC
CATTAATGAGATGTTATTACTGTTTTGGGCCTCCATGCCCCAGCTCTGGA
TGAAGGCAAAACTGTACTGTGTTTCGCATTAAGCACACACATCTGGCCC
TGACTTCTGGAGATGGATCCTTCCATCTTGTGGGGCCAGGACCATGGCCG
AAGCCCCTTGGAGAGAGGCTGCCTCAGCCAGTGGCACAGGAGACTCCA
AGGAGCTACTGACATTCCTAAGAGTGGAGGAGGAGGAGGAGCCTTGCTGG
GCCAGGGAAACAAAGTTTACATTGTCCTGTAGCTTTAAAACCACAGCTGG
GCAGGG [SEQ ID NO: 12]
```

The invention claimed is:

1. A method of treating acute myelocytic leukemia (AML) in a human subject in need thereof, comprising:
   (a) identifying a human subject with AML, comprising:
      (i) detecting a level of expression of 3-phosphoglycerate dehydrogenase (PHGDH) in the subject by contacting a sample from the subject with a reagent that specifically binds PHGDH protein or PHGDH mRNA;
      (ii) diagnosing the subject with AML when the level of PHGDH is increased relative to a control sample; and
   (b) administering an effective amount of an Axl inhibitor to the subject with AML;
   wherein the sample from the subject is a blood sample, a serum sample, a plasma sample, a bone marrow biopsy, or a spleen biopsy; and
   wherein the sample from the subject and the control sample are the same sample type.

2. The method of claim 1, wherein the method comprises detecting a level of expression or activity of PHGDH and one or more biomarkers selected from Axl, Akt, Erk, PLCγ, and SLFN11, in the subject or in a sample from the subject.

3. The method of claim 2, wherein the method comprises detecting a level of expression or activity of:
   (a) PHGDH, PLCγ1, and SLFN11; or
   (b) Axl, Akt, Erk, PLCγ1, PHGDH, and SLFN11;
   in the subject or in a sample from the subject.

4. The method of claim 1, further comprising periodically assessing PHGDH activity or expression in the subject.

5. The method of claim 1, wherein the method comprises administering an effective amount of 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine (BGB324/R428).

6. A method of treating acute myelocytic leukemia (AML) in a human subject in need thereof, comprising administering an effective amount of an Axl inhibitor to the subject, wherein the subject was previously determined to have AML by:
   (a) contacting a sample from the subject with a reagent that specifically binds 3-phosphoglycerate dehydrogenase (PHGDH) protein or mRNA; and
   (b) detecting an increased level of expression of PHGDH in the sample relative to a control sample;
   wherein the sample from the subject is a blood sample, a serum sample, a plasma sample, a bone marrow biopsy, or a spleen biopsy; and
   wherein the sample from the subject and the control sample are the same sample type.

7. The method of claim 6, wherein a sample from the subject has been determined to have an altered level of expression or activity of PHGDH and one or more biomarkers selected from Axl, Akt, Erk, PLCγ, and SLFN11 relative to a control sample.

8. The method of claim 6, wherein a sample from the subject has been determined to have an altered level of expression or activity of:
   (i) PHGDH, PLCγ1, and SLFN11; or
   (ii) Axl, Akt, Erk, PLCγ1, PHGDH, and SLFN11;
   relative to a control sample.

9. The method of claim 6, further comprising periodically assessing PHGDH activity or expression in the subject.

10. The method of claim 6, wherein the method comprises administering an effective amount of 1-(6,7-dihydro-5H-benzo[6,7]cyclohepta[1,2-c]pyridazin-3-yl)-N3-((7-(S)-pyrrolidin-1-yl)-6,7,8,9-tetrahydro-5H-benzo[7]annulene-2-yl)-1H-1,2,4-triazole-3,5-diamine (BGB324/R428).

* * * * *